US009611510B2

(12) United States Patent
He et al.

(10) Patent No.: US 9,611,510 B2
(45) Date of Patent: Apr. 4, 2017

(54) COMPOSITION AND METHODS RELATED TO MODIFICATION OF 5-METHYLCYTOSINE (5-MC)

(75) Inventors: Chuan He, Chicago, IL (US); Liang Zhang, Shanghai (CN); Chunxiao Song, Palo Alto, CA (US); Miao Yu, Chicago, IL (US)

(73) Assignee: The University of Chicago, Chicago, IL (US)

( * ) Notice: Subject to any disclaimer, the term of this patent is extended or adjusted under 35 U.S.C. 154(b) by 316 days.

(21) Appl. No.: 14/110,007

(22) PCT Filed: Apr. 6, 2012

(86) PCT No.: PCT/US2012/032489
§ 371 (c)(1),
(2), (4) Date: Feb. 26, 2014

(87) PCT Pub. No.: WO2012/138973
PCT Pub. Date: Oct. 11, 2012

(65) Prior Publication Data
US 2014/0322707 A1  Oct. 30, 2014

Related U.S. Application Data

(60) Provisional application No. 61/472,435, filed on Apr. 6, 2011, provisional application No. 61/512,334, filed on Jul. 27, 2011.

(51) Int. Cl.
C12Q 1/68 (2006.01)
C12P 19/34 (2006.01)
C07H 21/02 (2006.01)
G06F 19/00 (2011.01)

(52) U.S. Cl.
CPC ......... *C12Q 1/6869* (2013.01); *C12Q 1/6827* (2013.01)

(58) Field of Classification Search
None
See application file for complete search history.

(56) References Cited

U.S. PATENT DOCUMENTS

| | | | |
|---|---|---|---|
| 5,547,839 A | 8/1996 | Dower et al. | 435/6.11 |
| 6,210,896 B1 | 4/2001 | Chan | 435/6.19 |
| 6,255,083 B1 | 7/2001 | Williams | 435/91.1 |
| 6,555,311 B1 | 4/2003 | Locarnini et al. | 435/5 |
| 6,787,308 B2 | 9/2004 | Balasubramanian | 506/9 |
| 7,056,661 B2 | 6/2006 | Korlach et al. | 435/6.1 |

(Continued)

FOREIGN PATENT DOCUMENTS

| | | |
|---|---|---|
| WO | WO/91/06678 | 5/1991 |
| WO | WO/96/27025 | 9/1996 |

(Continued)

OTHER PUBLICATIONS

Ito et al. Science. 2011. 333: 1300-1303.*

(Continued)

*Primary Examiner* — Joseph G Dauner
(74) *Attorney, Agent, or Firm* — Norton Rose Fulbright US LLP

(57) ABSTRACT

The present invention relates to methods and compositions for detecting, evaluating, and/or mapping 5-methyl-modified and/or 5-hydroxylmethyl-modified cytosine bases within a nucleic acid molecule.

10 Claims, 31 Drawing Sheets

(56) References Cited

U.S. PATENT DOCUMENTS

| | | | |
|---|---|---|---|
| 7,399,614 B2 | 7/2008 | Zon | 435/91.1 |
| 7,459,274 B2 | 12/2008 | Lakey et al. | 435/6.12 |
| 7,611,869 B2 | 11/2009 | Fan | 435/91.2 |
| 2002/0102577 A1 | 8/2002 | Raillard et al. | 435/6.15 |
| 2003/0096253 A1 | 5/2003 | Nelson et al. | 435/5 |
| 2003/0190647 A1 | 10/2003 | Odera | 435/6.13 |
| 2003/0215862 A1 | 11/2003 | Parce et al. | 435/6.11 |
| 2004/0048300 A1 | 3/2004 | Sood et al. | 435/6.18 |
| 2004/0152119 A1 | 8/2004 | Sood et al. | 435/6.12 |
| 2004/0224319 A1 | 11/2004 | Sood et al. | 435/6.1 |
| 2005/0053937 A1 | 3/2005 | Berlin | 435/6.12 |
| 2005/0208538 A1 | 9/2005 | Kurn et al. | 435/6.12 |
| 2005/0214812 A1 | 9/2005 | Li et al. | 435/6.1 |
| 2006/0024676 A1 | 2/2006 | Uhlmann et al. | 435/6.12 |
| 2006/0063264 A1 | 3/2006 | Turner et al. | 436/8 |
| 2008/0207460 A1 | 8/2008 | Gormley | 506/3 |
| 2009/0012282 A1 | 1/2009 | Zon | 536/26.6 |
| 2009/0024331 A1 | 1/2009 | Tomaney et al. | 702/19 |
| 2009/0269771 A1 | 10/2009 | Schroeder | 435/6.12 |
| 2010/0041057 A1 | 2/2010 | Dong | 435/6.12 |
| 2010/0121582 A1 | 5/2010 | Pan et al. | 702/20 |
| 2010/0190175 A1 | 7/2010 | Gerard et al. | 435/6.1 |
| 2011/0104787 A1 | 5/2011 | Church et al. | 435/227 |
| 2011/0201524 A1 | 8/2011 | Kester | 21/9 |
| 2011/0236894 A1 | 9/2011 | Rao et al. | 435/6.11 |
| 2011/0237444 A1 | 9/2011 | Clancy et al. | 506/7 |
| 2013/0244237 A1 | 9/2013 | Vaisvila et al. | 435/6.11 |
| 2014/0004511 A1 | 1/2014 | Korlach | 435/6.11 |
| 2014/0127677 A1 | 5/2014 | Correa, Jr. et al. | 435/6.1 |
| 2014/0127678 A1 | 5/2014 | Guan et al. | 435/6.1 |
| 2014/0127683 A1 | 5/2014 | Zheng et al. | 435/6.11 |

FOREIGN PATENT DOCUMENTS

| | | | | |
|---|---|---|---|---|
| WO | WO/99/05315 | 2/1999 | | |
| WO | WO/2006/005064 | 1/2006 | | |
| WO | WO/2010/003153 | 1/2010 | | |
| WO | WO 2010037001 A2 * | 4/2010 | | C12N 9/0071 |
| WO | WO/2010/068289 | 6/2010 | | |
| WO | WO 2011/025819 | 3/2011 | | |

OTHER PUBLICATIONS

He et al. Science. 2011. 333: 1303-1307.*
GenBank ACY38291.1 (Nov. 3, 2009).*
Beck and Rakyan, *Trends Genet.*, 24:231-237, 2008.
Beck, *Nat. Biotechnol.*, 28:1026-1028, 2010.
Berman et al., *Nat. Genet.*, 44:40-46, 2012.
Bernstein et al., *Cell*, 128:669-681, 2007.
Bird, *Genes Dev.*, 16:6-21, 2002.
Bird, *J. Mol. Biol.*, 409:47-53, 2011.
Bock et al., *Nat. Biotechnol.*, 28:1106-1114, 2010.
Bock, *Epigenomics*, 1:99-110, 2009.
Boysen et al., *J. Chromatogr. B Analyt. Technol. Biomed. Life Sci.*, 878:375, 2010.
Chavez et al., *Genome Res.*, 20:1441-1450, 2010.
Chen and Riggs, *J. Biol. Chem.*, 286:18347-18353, 2011.
Clark et al., *Nucleic Acids Res.* 22:2990-2997, 1994.
Cokus et al., *Nature*, 452:215-219, 2008.
Cortellino et al., *Cell*, 146:67-79, 2011.
Dai and He, *Org. Lett.*, 13:3446-3449, 2011.
Dawlaty et al., *Cell. Stem Cell*, 9:166-175, 2011.
De Carvalho et al., *Trends Cell Biol.*, 20:609-617, 2010.
Deaton and Bird, *Genes Dev.*, 25:1010-1022, 2011.
Donnelly et al., *Protein Expr. Purif.*, 47(2):446-454, 2006.
Down et al., *Nat. Biotechnol.*, 26:779-785, 2008.
Esteller and Aberrant, *Annu. Rev. Pharmacol. Toxicol.*, 45:629-656, 2005.
Esteller, *Nat. Rev. Genet.*, 8:286-298, 2007.
Evans, *Austral. J. Chem.*, 60(6): 384-395, 2007.
Feinberg and Tycko, *Nat. Rev. Cancer*, 4:143-153, 2004.

Feinberg and Vogelstein, *Nature*, 301(5895):89-92, 1983.
Ficz et al., *Nature*, 473:398-402, 2011.
Frauer et al., *PloS One*, 6:e21306, 2011.
Frommer et al.: *Proc. Natl. Acad. Sci. USA*, 89:1827-1831, 1992.
Geier and Modrich, *J. Biol. Chem.*, 254:1408-1413, 1979.
Globisch et al., *PloS One*, 5:e15367, 2010.
Goll and Bestor, *Annu. Rev. Biochem.*, 74:481-514, 2005.
Gu et al., *Nature*, 477:606-610, 2011.
Guo et al., *Cell*, 145:423-434, 2011.
Harris et al., *Nat. Biotechnol.*, 28:1097-1105, 2010.
Hashimoto et al., *Nucleic Acids Res.* 40(11):4841-4849, 2012.
Hashimoto et al., *Nucleic Acids Res.* 40(17):8276-84, 2012.
Hashimoto et al., *Nucleic Acids Res.* 40(20):10203-10214, 2012.
Hawkins et al., *Cell. Stem Cell*, 6:479-491, 2010.
He et al., *Science*, 333:1303-1307, 2011.
Hein et al., *Pharmaceut. Res.*, 25(10):2216-2230, 2008.
Hon et al., *Genome Res.*, 22:246-258, 2012.
Hsu et al., *Bioinformatics*, 22:1036-1046, 2006.
Huang et al., *Nucleic Acids Res.*, 10:1579, 1982.
Huang et al., *PLoS One* 5, e8888, 2010.
Inoue and Zhang, *Science*, 334:194, 2011.
Iqbal et al.: *Proc. Natl. Acad. Sci. USA*, 108:3642-3647, 2011.
Ito et al., *Nature*, 466:1129-1133, 2010.
Ito et al., *Science*, 333:1300-1303, 2011.
Jacinto et al., *Biotechniques*, 44:35, 37, 39 passim, 2008.
Jaenisch and Bird, *Nat. Genet.*, 33(Suppl):245-254, 2003.
Jin et al., *Nucleic Acids Res.*, 38:e125, 2010.
Jones and Baylin, *Nat. Rev. Genet.*, 3:415-428, 2002.
Josse and Kornberg, *Biol. Chem.*, 237:1968-1976, 1962.
Kent et al., *Genome Res.*, 12:996-1006, 2002.
Ko et al., *Nature*, 468:839-843, 2010.
Koh et al., *Cell. Stem Cell*, 8:200-213, 2011.
Kolb et al., *Angew. Chem. Int. Ed.*, 40:2004-2021, 2001.
Kriaucionis and Heintz, *Science*, 324:929-930, 2009.
Langmead et al., *Genome Biol.*, 10:R25, 2009.
Law and Jacobsen, *Nat. Rev. Genet.*, 11:204-220, 2010.
Li et al., *Bioinformatics*, 25:2078-2079, 2009.
Lister et al., *Cell*, 133:523-536, 2008.
Lister et al., *Nature*, 462:315-322, 2009.
Lister et al., *Nature*, 471:68-73, 2011.
Lorsbach et al., *Leukemia*, 17: 637-641, 2003.
Matti and Drohat, *J. Biol. Chem.*, 286:35334-35338, 2011.
Margulies et al., *Nature*, 437:376-380, 2005.
Marinus and Morris, *J. Bacteriol.*, 114:1143-1150, 1973.
May and Hallman, *J. Bacteriol.*, 123:768-770, 1975.
Meissner et al., *Nature*, 454:766-770, 2008.
Meissner, *Nat. Biotechnol.*, 28:1079-1088, 2010.
Meyer et al., *Chem. Bio. Chem.*, 4:610-614, 2003.
Mishina and He, *J. Am. Chem. Soc.*, 125:8730-8731, 2003.
Moses and Moorhouse, *Chem. Soc. Rev.*, (36):1249-1262, 2007.
Munzel, et al., *Angew Chem. Int. Ed. Engl.*, 49:5375-5377, 2010.
Myers et al., *PLoS Biol.*, 9:e1001046., 2011.
Okazaki, et al., *DNA Res.* 19:167-180, 2003.
Ono et al., *Cancer Res.*, 62:4075-4080, 2002.
Pastor et al., *Nature*, 473:394-397, 2011.
Pelizzola and Ecker, *FEBS Ltrs.*, 585:1994-2000, 2011.
Pfaffeneder et al., *Angew Chem. Int. Ed Engl.*, 50:7008-7012, 2011.
Quenneville et al., *Mol. Cell*, 44:361-372, 2011.
Robertson et al., *Nat. Protoc.*, 7:340-350, 2012.
Robertson et al., *Nucleic Acids Res.*, 39:e55, 2011.
Schuebel et al., *PLoS Genet.*, 3:1709-1723, 2007.
Search Report and Written Opinion in PCT/US2012/032489 mailed Sep. 4, 2012.
Siegfried and Cedar, *Curr. Biol.*, 7:305-307, 1997.
Siepel et al., *Genome Res.*, 15:1034-1050, 2005.
Song et al., *Nat. Methods*, 9:75-77, 2012.
Song, et al., *Nature Biotechnol.* 29(1):68-72, 2011.
Stadler et al., *Nature*, 480:490-495, 2011.
Stroud et al., *Genome Biol.*, 12:R54, 2011.
Szulwach et al., *Nat. Neurosci.*, 14:1607-1616, 2011.
Szulwach et al., *PLoS Genet.*, 7:e1002154, 2011.
Szwagierczak et al., *Nucleic Acids Res.*, 38:e181, 2010.
Tahiliani, et al., *Science.* 324:930-5, 2009.

(56) References Cited

OTHER PUBLICATIONS

Tanabe et al., *J. Am. Chem. Soc.*, 129:8034-8040, 2007.
Tornoe et al., *J. Organic Chem.*, 67(9):3057-3064, 2002.
Valinluck et al., *Nucleic Acids Res.*, 32:4100-4108, 2004.
Weber et al., *Nature Genetics*, 37:853-862, 2005.
Weisenberger et al., In *Comprehensive DNA Methylation Analysis on the Illumina® Infinium® Assay Platform*, Pub. No. 270-2008-003, Illumina, 2008.
Wigler et al., *Cell*, 24:33-40, 1981.
Williams et al., *Anal. Biochem.*, 114:73, 1981.
Williams et al., *Nature*, 473:343-348, 2011.
Wossidlo et al., *Nat. Commun.*, 2:241, 2011.
Wu and Zhang, *Genes Dev.*, 25:2436-2452, 2011.
Wu et al., *Genes Dev.*, 25:679-684, 2011.
Xu et al., *Mol. Cell*, 42:451-464, 2011.
Yildirim et al., *Cell*, 147:1498-1510, 2011.
Zeschnigk et al., *Hum. Mol. Genet.*, 6:387-395, 1997.
Zhang et al., *Genome Biol.*, 9: R137, 2008.
Zhang et al., *Nature Chem. Biol.*, 8:328-330, 2012.
Abbotts, et al., J Biol Chem. 263:15094-103, 1988.
Ahle, et al., Nucl Acids Res. 33(10):3176-84, 2005.
Ananiev, et al., BMC Mol Biol. 9:68, 2008.
Avvakumov, et al., Nature. 455(7214):822-25, 2008.
Banerjee, et al., Nature. 434(7033):612-8, 2005.
Bareyt, et al., Angew Chem Int Ed Engl. 47(1):181-4, 2008.
Berman, et al., EMBO J. 26:3494-3505, 2007.
Blainey, et al., PNAS. 103(15):5752-57, 2006.
Braun & Muller, Statistical Sci. 13(2):142-62, 1998.
Brewer, et al., Nucl Acids Res. 18:5574, 1990.
Brunner, et al., Genome Res. 19:1044-56, 2009.
Clark, et al., BMC Biology. 11:4, 2013.
Colasanti, et al., Nucl Acids Res. 19(2):391-4, 1991.
Cordonnier, et al., Mol Cell Biol, 19(3):2206-11, 1999.
Eid, et al., Science. 323:133-8, 2009.
Everts, et al., C&EN. 87:36:65-8, 2009.
Fellers, et al., Plant Genome. 1(2):146-52, 2008.
Finkel, et al., Nature. 408(6809):239-47, 2000.
Flusberg, et al., Nat Meth. 7(6):461-7, 2010.
Friedberg, et al., Nat Rev Mol Cell Biol. 6(12):943-53, 2005.
Fromme, et al., Adv Protein Chem, 69:1-41, 2004.
Galas, et al., Nucl Acids Res. 5(9):3157-70, 1978.
Hafner, et al., Cell. 141(1):129-41, 2010.
Hamm, et al., J Am Chem Soc. 129(25):7724-5, 2007.
Hanes, et al., J Biol Chem. 281(47):36241-8, 2006.
Hashimoto, et al., Nature. 455(7214):826-9, 2008.
Hayatsu, et al., Mutation Res. 659(1-2):77-82, 2008.
Hendrich, et al., Mol Cell Biol. 18(11):6538-47, 1998.
Herbert, et al., Ann Rev Biochem. 77:149-76, 2008.
Holmquist, et al., Mutat Res. 510(1-2):1-7, 2002.
Horowitz, et al., PNAS. 81(18):5667-71, 1984.
Hsu, et al., Nature. 431(7005):217-21, 2004.
Huang, et al., Cancer Res. 57:1030-4, 1997.
Ingolia, et al., Science. 324(5924):218-23, 2009.
International Search Report and Written Opinion in International Application No. PCT/US2013/037829 dated Sep. 24, 2013.
Jones, et al., Nat Genet. 21(2):163-7, 1999.
Jorgensen, et al., Nucl Acids Res. 34(13):e96, 2006.
Kannouche, et al., Cell Cycle. 3(8):1011-3, 2004.
Kannouche, et al., Mol Cell. 14(4):491-500, 2004.
Kilgore, et al., Methods. 41:320-32, 2007.
Klungland, et al., DNA Repair (Amst). 6(4):481-8, 2007.
Krueger, et al., Chem & Biol. 16(3):242-8, 2009.
Krueger, et al., Curr Opin Chem Biol. 11(6):588-94, 2007.
Laird, et al., Nat Rev Cancer. 3(4):253-66, 2003.
Lehmann, et al., DNA Repair (Amst):6(7):891-99, 2007.
Lehmann, et al., Exp Cell Res. 312(14):2673-76, 2006.
Lehmann, et al., Mutat Res. 509(1-2):23-34, 2002.
Levene, et al., Science. 299(5607):682-86, 2003.
Lindahl, et al., Nature. 362(6422):709-15, 1993.
Lister, et al., Genome Res. 19:959-66, 2009.
Loakes, et al., Chem Commun. 31:4619-31, 2009.
Ludlum, et al., J Biol Chem. 243(10):2750-3, 1968.
Masutani, et al., Nature. 399(6737):700-4, 1999.
Matray, et al., Nature. 399:704-8, 1999.
McCullough, et al., Ann Rev Biochem. 68:255-85, 1999.
Merino, et al., J Am Chem Soc. 127:4223-31, 2005.
Morgan, et al., J Biol Chem. 279:4223-31, 2005.
Morozova, et al., Genomics. 92:255-64, 2008.
Narayan, et al., Mol Cell Biol. 7(4):1572-75, 2008.
Ohki, et al., EMBO J 18(23):6653-61, 2000.
Ohmori, et al., Mol Cell. 8(1):7-8, 2001.
Okamoto, et al., Nucleic Acids. 26(10-12):1601-4, 2007.
Petrov, et al., Nucl Acids Res. 8(18):4221-34, 1980.
Radicella, et al., PNAS. 94:8010-5, 1997.
Rollins, et al., Genome Res. 16:157-63, 2006.
Sadri, et al., Nucl Acids Res. 24(24):5058-9, 1996.
Seo, et al., J Am Chem Soc. 131:3246-52, 2009.
Smith, et al., PNAS. 89:4744-48, 1992.
Smolina, et al., J Mol Biol. 326:1113-25, 2003.
Tanaka, et al., J Am Chem Soc. 129(17):5612-20, 2007.
Tijerina, et al., Nature Protocols. 2:2608-23, 2007.
Tost, et al., Nature Protocols. 2(9):2265-75, 2007.
Vidal, et al., Nucl Acids Res. 29(6):1285-92, 2001.
Viguera, et al., EMBO J. 20(1):2587-95, 2001.
Vlassov, et al., Bioessays. 29(7):654-67, 2007.
Yebra, et al., Biochemistry. 34(45):14752-7, 1995.
Zheng, et al., Nucl Acids Res. 38(1):327-38, 2010.

* cited by examiner

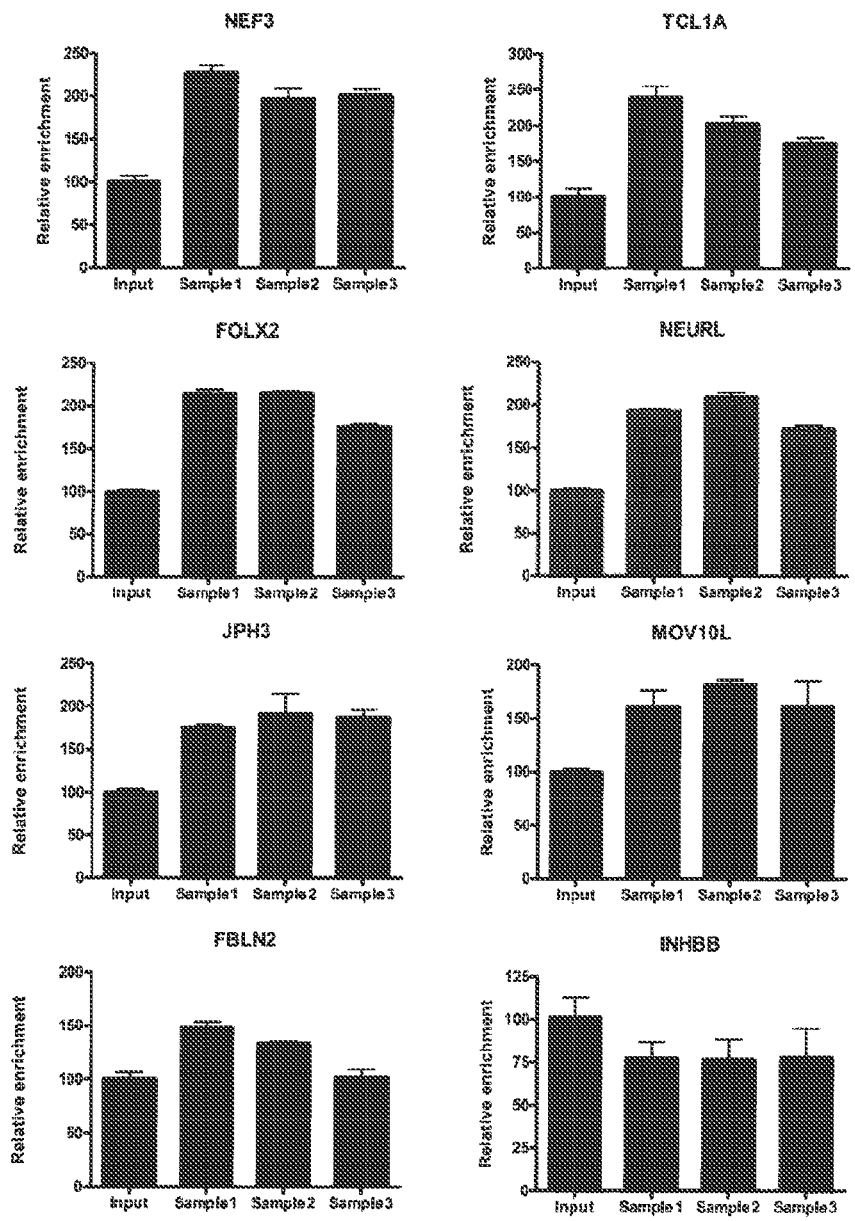
FIG. 6A (continued-1)

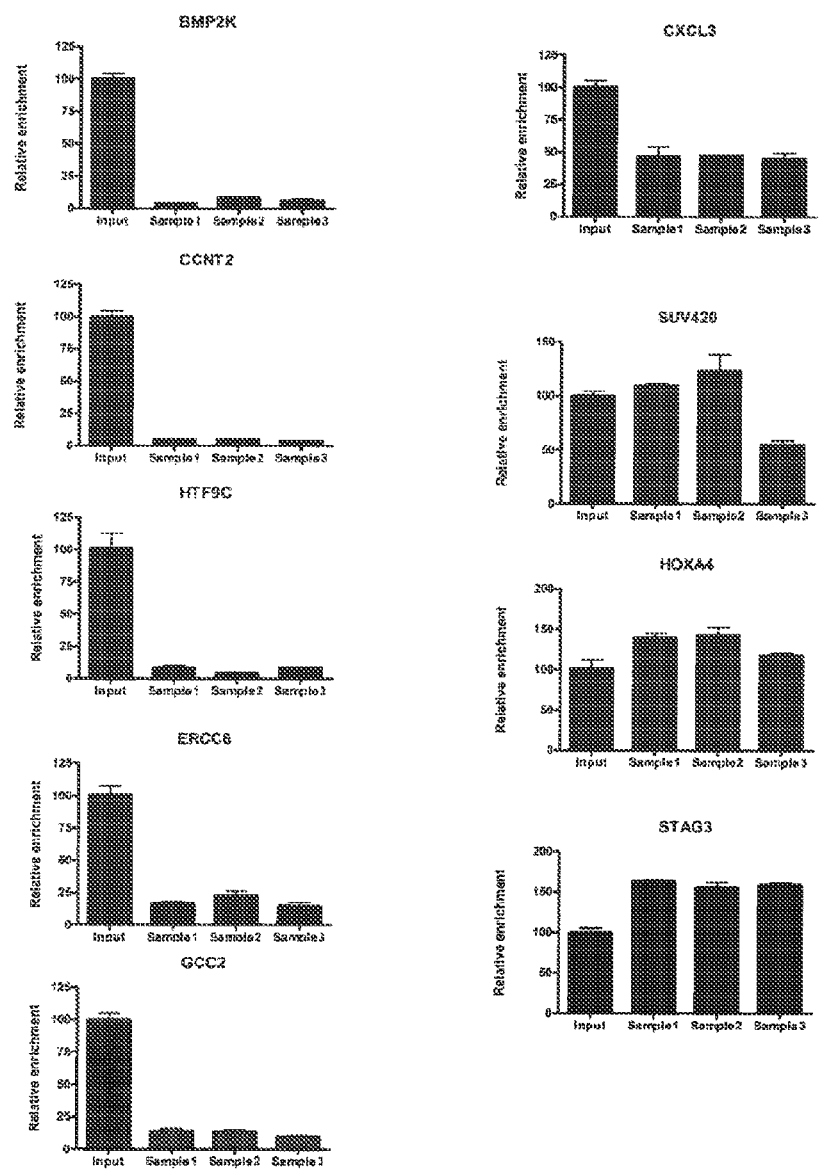
FIG. 6A (continued-2)

SEQUENCE LISTING

<160> NUMBER OF SEQ ID NOS: 26

<210> SEQ ID NO 1
<211> LENGTH: 2039
<212> TYPE: PRT
<213> ORGANISM: Mus musculus

<400> SEQUENCE: 1

```
Met Ser Arg Ser Arg Pro Ala Lys Pro Ser Lys Ser Val Lys Thr Lys
1               5                   10                  15

Leu Gln Lys Lys Lys Asp Ile Gln Met Lys Thr Lys Thr Ser Lys Gln
            20                  25                  30

Ala Val Arg His Gly Ala Ser Ala Lys Ala Val Asn Pro Gly Lys Pro
        35                  40                  45

Lys Gln Leu Ile Lys Arg Arg Asp Gly Lys Lys Glu Thr Glu Asp Lys
    50                  55                  60

Thr Pro Thr Pro Ala Pro Ser Phe Leu Thr Arg Ala Gly Ala Ala Arg
65                  70                  75                  80

Met Asn Arg Asp Arg Asn Gln Val Leu Phe Gln Asn Pro Asp Ser Leu
                85                  90                  95

Thr Cys Asn Gly Phe Thr Met Ala Leu Arg Arg Thr Ser Leu Ser Trp
            100                 105                 110

Arg Leu Ser Gln Arg Pro Val Val Thr Pro Lys Pro Lys Lys Val Pro
        115                 120                 125

Pro Ser Lys Lys Gln Cys Thr His Asn Ile Gln Asp Glu Pro Gly Val
    130                 135                 140

Lys His Ser Glu Asn Asp Ser Val Pro Ser Gln His Ala Thr Val Ser
145                 150                 155                 160

Pro Gly Thr Glu Asn Gly Glu Gln Asn Arg Cys Leu Val Glu Gly Glu
                165                 170                 175

Ser Gln Glu Ile Thr Gln Ser Cys Pro Val Phe Glu Gly Arg Ile Glu
            180                 185                 190

Asp Thr Gln Ser Cys Ile Ser Ala Ser Gly Asn Leu Glu Ala Glu Ile
        195                 200                 205

Ser Trp Pro Leu Glu Gly Thr His Cys Glu Glu Leu Leu Ser His Gln
    210                 215                 220

Thr Ser Asp Asn Glu Cys Thr Ser Pro Gln Glu Cys Ala Pro Leu Pro
225                 230                 235                 240

Gln Arg Ser Thr Ser Glu Val Thr Ser Gln Lys Asn Thr Ser Asn Gln
                245                 250                 255

Leu Ala Asp Leu Ser Ser Gln Val Glu Ser Ile Lys Leu Ser Asp Pro
            260                 265                 270

Ser Pro Asn Pro Thr Gly Ser Asp His Asn Gly Phe Pro Asp Ser Ser
        275                 280                 285

Phe Arg Ile Val Pro Glu Leu Asp Leu Lys Thr Cys Met Pro Leu Asp
    290                 295                 300

Glu Ser Val Tyr Pro Thr Ala Leu Ile Arg Phe Ile Leu Ala Gly Ser
305                 310                 315                 320

Gln Pro Asp Val Phe Asp Thr Lys Pro Gln Glu Lys Thr Leu Ile Thr
                325                 330                 335

Thr Pro Glu Gln Val Gly Ser His Pro Asn Gln Val Leu Asp Ala Thr
            340                 345                 350

Ser Val Leu Gly Gln Ala Phe Ser Thr Leu Pro Leu Gln Trp Gly Phe
        355                 360                 365
```

-continued

```
Ser Gly Ala Asn Leu Val Gln Val Glu Ala Leu Gly Lys Gly Ser Asp
    370                 375                 380

Ser Pro Glu Asp Leu Gly Ala Ile Thr Met Leu Asn Gln Gln Glu Thr
385                 390                 395                 400

Val Ala Met Asp Met Asp Arg Asn Ala Thr Pro Asp Leu Pro Ile Phe
                405                 410                 415

Leu Pro Lys Pro Pro Asn Thr Val Ala Thr Tyr Ser Ser Pro Leu Leu
            420                 425                 430

Gly Pro Glu Pro His Ser Ser Thr Ser Cys Gly Leu Glu Val Gln Gly
        435                 440                 445

Ala Thr Pro Ile Leu Thr Leu Asp Ser Gly His Thr Pro Gln Leu Pro
    450                 455                 460

Pro Asn Pro Glu Ser Ser Val Pro Leu Val Ile Ala Ala Asn Gly
465                 470                 475                 480

Thr Arg Ala Glu Lys Gln Phe Gly Thr Ser Leu Phe Pro Ala Val Pro
                485                 490                 495

Gln Gly Phe Thr Val Ala Ala Glu Asn Glu Val Gln His Ala Pro Leu
            500                 505                 510

Asp Leu Thr Gln Gly Ser Gln Ala Ala Pro Ser Lys Leu Glu Gly Glu
        515                 520                 525

Ile Ser Arg Val Ser Ile Thr Gly Ser Ala Asp Val Lys Ala Thr Ala
    530                 535                 540

Met Ser Met Pro Val Thr Gln Ala Ser Thr Ser Ser Pro Pro Cys Asn
545                 550                 555                 560

Ser Thr Pro Pro Met Val Glu Arg Arg Lys Arg Lys Ala Cys Gly Val
                565                 570                 575

Cys Glu Pro Cys Gln Gln Lys Ala Asn Cys Gly Glu Cys Thr Tyr Cys
            580                 585                 590

Lys Asn Arg Lys Asn Ser His Gln Ile Cys Lys Lys Arg Lys Cys Glu
        595                 600                 605

Val Leu Lys Lys Lys Pro Glu Ala Thr Ser Gln Ala Gln Val Thr Lys
    610                 615                 620

Glu Asn Lys Arg Pro Gln Arg Glu Lys Lys Pro Lys Val Leu Lys Thr
625                 630                 635                 640

Asp Phe Asn Asn Lys Pro Val Asn Gly Pro Lys Ser Glu Ser Met Asp
                645                 650                 655

Cys Ser Arg Arg Gly His Gly Glu Glu Gln Arg Leu Asp Leu Ile
            660                 665                 670

Thr His Pro Leu Glu Asn Val Arg Lys Asn Ala Gly Gly Met Thr Gly
        675                 680                 685

Ile Glu Val Glu Lys Trp Ala Pro Asn Lys Lys Ser His Leu Ala Glu
    690                 695                 700

Gly Gln Val Lys Gly Ser Cys Asp Ala Asn Leu Thr Gly Val Glu Asn
705                 710                 715                 720

Pro Gln Pro Ser Glu Asp Lys Gln Gln Thr Asn Pro Ser Pro Thr
                725                 730                 735

Phe Ala Gln Thr Ile Arg Asn Gly Met Lys Asn Val His Cys Leu Pro
            740                 745                 750

Thr Asp Thr His Leu Pro Leu Asn Lys Leu Asn His Glu Glu Phe Ser
        755                 760                 765

Lys Ala Leu Gly Asn Asn Ser Ser Lys Leu Leu Thr Asp Pro Ser Asn
    770                 775                 780

Cys Lys Asp Ala Met Ser Val Thr Thr Ser Gly Gly Glu Cys Asp His
```

-continued

```
            785                 790                 795                 800
Leu Lys Gly Pro Arg Asn Thr Leu Leu Phe Gln Lys Pro Gly Leu Asn
                    805                 810                 815

Cys Arg Ser Gly Ala Glu Pro Thr Ile Phe Asn Asn His Pro Asn Thr
                    820                 825                 830

His Ser Ala Gly Ser Arg Pro His Pro Pro Glu Lys Val Pro Asn Lys
                    835                 840                 845

Glu Pro Lys Asp Gly Ser Pro Val Gln Pro Ser Leu Leu Ser Leu Met
            850                 855                 860

Lys Asp Arg Arg Leu Thr Leu Glu Gln Val Val Ala Ile Glu Ala Leu
865                 870                 875                 880

Thr Gln Leu Ser Glu Ala Pro Ser Glu Ser Ser Pro Ser Lys Pro
                    885                 890                 895

Glu Lys Asp Glu Glu Ala His Gln Lys Thr Ala Ser Leu Leu Asn Ser
                    900                 905                 910

Cys Lys Ala Ile Leu His Ser Val Arg Lys Asp Leu Gln Asp Pro Asn
                    915                 920                 925

Val Gln Gly Lys Gly Leu His His Asp Thr Val Phe Asn Gly Gln
            930                 935                 940

Asn Arg Thr Phe Lys Ser Pro Asp Ser Phe Ala Thr Asn Gln Ala Leu
945                 950                 955                 960

Ile Lys Ser Gln Gly Tyr Pro Ser Ser Pro Thr Ala Glu Lys Lys Gly
                    965                 970                 975

Ala Ala Gly Gly Arg Ala Pro Phe Asp Gly Phe Glu Asn Ser His Pro
                    980                 985                 990

Leu Pro Ile Glu Ser His Asn Leu  Glu Asn Cys Ser Gln  Val Leu Ser
            995                 1000                1005

Cys Asp Gln Asn Leu Ser Ser  His Asp Pro Ser Cys  Gln Asp Ala
        1010                1015                1020

Pro Tyr Ser Gln Ile Glu Glu  Asp Val Ala Ala Gln  Leu Thr Gln
        1025                1030                1035

Leu Ala Ser Thr Ile Asn His  Ile Asn Ala Glu Val  Arg Asn Ala
        1040                1045                1050

Glu Ser Thr Pro Glu Ser Leu  Val Ala Lys Asn Thr  Lys Gln Lys
        1055                1060                1065

His Ser Gln Glu Lys Arg Met  Val His Gln Lys Pro  Pro Ser Ser
        1070                1075                1080

Thr Gln Thr Lys Pro Ser Val  Pro Ser Ala Lys Pro  Lys Lys Ala
        1085                1090                1095

Gln Lys Lys Ala Arg Ala Thr  Pro His Ala Asn Lys  Arg Lys Lys
        1100                1105                1110

Lys Pro Pro Ala Arg Ser Ser  Gln Glu Asn Asp Gln  Lys Lys Gln
        1115                1120                1125

Glu Gln Leu Ala Ile Glu Tyr  Ser Lys Met His Asp  Ile Trp Met
        1130                1135                1140

Ser Ser Lys Phe Gln Arg Phe  Gly Gln Ser Ser Pro  Arg Ser Phe
        1145                1150                1155

Pro Val Leu Leu Arg Asn Ile  Pro Val Phe Asn Gln  Ile Leu Lys
        1160                1165                1170

Pro Val Thr Gln Ser Lys Thr  Pro Ser Gln His Asn  Glu Leu Phe
        1175                1180                1185

Pro Pro Ile Asn Gln Ile Lys  Phe Thr Arg Asn Pro  Glu Leu Ala
        1190                1195                1200
```

```
Lys Glu Lys Val Lys Val Glu Pro Ser Asp Ser Leu Pro Thr Cys
1205                1210                1215

Gln Phe Lys Thr Glu Ser Gly Gly Gln Thr Phe Ala Glu Pro Ala
1220                1225                1230

Asp Asn Ser Gln Gly Gln Pro Met Val Ser Val Asn Gln Glu Ala
1235                1240                1245

His Pro Leu Pro Gln Ser Pro Pro Ser Asn Gln Cys Ala Asn Ile
1250                1255                1260

Met Ala Gly Ala Ala Gln Thr Gln Phe His Leu Gly Ala Gln Glu
1265                1270                1275

Asn Leu Val His Gln Ile Pro Pro Pro Thr Leu Pro Gly Thr Ser
1280                1285                1290

Pro Asp Thr Leu Leu Pro Asp Pro Ala Ser Ile Leu Arg Lys Gly
1295                1300                1305

Lys Val Leu His Phe Asp Gly Ile Thr Val Val Thr Glu Lys Arg
1310                1315                1320

Glu Ala Gln Thr Ser Ser Asn Gly Pro Leu Gly Pro Thr Thr Asp
1325                1330                1335

Ser Ala Gln Ser Glu Phe Lys Glu Ser Ile Met Asp Leu Leu Ser
1340                1345                1350

Lys Pro Ala Lys Asn Leu Ile Ala Gly Leu Lys Glu Gln Glu Ala
1355                1360                1365

Ala Pro Cys Asp Cys Asp Gly Gly Thr Gln Lys Glu Lys Gly Pro
1370                1375                1380

Tyr Tyr Thr His Leu Gly Ala Gly Pro Ser Val Ala Ala Val Arg
1385                1390                1395

Glu Leu Met Glu Thr Arg Phe Gly Gln Lys Gly Lys Ala Ile Arg
1400                1405                1410

Ile Glu Lys Ile Val Phe Thr Gly Lys Glu Gly Lys Ser Ser Gln
1415                1420                1425

Gly Cys Pro Val Ala Lys Trp Val Ile Arg Arg Ser Gly Pro Glu
1430                1435                1440

Glu Lys Leu Ile Cys Leu Val Arg Glu Arg Val Asp His His Cys
1445                1450                1455

Ser Thr Ala Val Ile Val Val Leu Ile Leu Leu Trp Glu Gly Ile
1460                1465                1470

Pro Arg Leu Met Ala Asp Arg Leu Tyr Lys Glu Leu Thr Glu Asn
1475                1480                1485

Leu Arg Ser Tyr Ser Gly His Pro Thr Asp Arg Arg Cys Thr Leu
1490                1495                1500

Asn Lys Lys Arg Thr Cys Thr Cys Gln Gly Ile Asp Pro Lys Thr
1505                1510                1515

Cys Gly Ala Ser Phe Ser Gly Cys Ser Trp Ser Met Tyr Phe
1520                1525                1530

Asn Gly Cys Lys Phe Gly Arg Ser Glu Asn Pro Arg Lys Phe Arg
1535                1540                1545

Leu Ala Pro Asn Tyr Pro Leu His Asn Tyr Tyr Lys Arg Ile Thr
1550                1555                1560

Gly Met Ser Ser Glu Gly Ser Asp Val Lys Thr Gly Trp Ile Ile
1565                1570                1575

Pro Asp Arg Lys Thr Leu Ile Ser Arg Glu Glu Lys Gln Leu Glu
1580                1585                1590
```

Lys Asn Leu Gln Glu Leu Ala Thr Val Leu Ala Pro Leu Tyr Lys
1595                1600                1605

Gln Met Ala Pro Val Ala Tyr Gln Asn Gln Val Glu Tyr Glu Glu
1610                1615                1620

Val Ala Gly Asp Cys Arg Leu Gly Asn Glu Glu Gly Arg Pro Phe
1625                1630                1635

Ser Gly Val Thr Cys Cys Met Asp Phe Cys Ala His Ser His Lys
1640                1645                1650

Asp Ile His Asn Met His Asn Gly Ser Thr Val Cys Thr Leu
1655                1660                1665

Ile Arg Ala Asp Gly Arg Asp Thr Asn Cys Pro Glu Asp Glu Gln
1670                1675                1680

Leu His Val Leu Pro Leu Tyr Arg Leu Ala Asp Thr Asp Glu Phe
1685                1690                1695

Gly Ser Val Glu Gly Met Lys Ala Lys Ile Lys Ser Gly Ala Ile
1700                1705                1710

Gln Val Asn Gly Pro Thr Arg Lys Arg Arg Leu Arg Phe Thr Glu
1715                1720                1725

Pro Val Pro Arg Cys Gly Lys Arg Ala Lys Met Lys Gln Asn His
1730                1735                1740

Asn Lys Ser Gly Ser His Asn Thr Lys Ser Phe Ser Ser Ala Ser
1745                1750                1755

Ser Thr Ser His Leu Val Lys Asp Glu Ser Thr Asp Phe Cys Pro
1760                1765                1770

Leu Gln Ala Ser Ser Ala Glu Thr Ser Thr Cys Thr Tyr Ser Lys
1775                1780                1785

Thr Ala Ser Gly Gly Phe Ala Glu Thr Ser Ser Ile Leu His Cys
1790                1795                1800

Thr Met Pro Ser Gly Ala His Ser Gly Ala Asn Ala Ala Ala Gly
1805                1810                1815

Glu Cys Thr Gly Thr Val Gln Pro Ala Glu Val Ala Ala His Pro
1820                1825                1830

His Gln Ser Leu Pro Thr Ala Asp Ser Pro Val His Ala Glu Pro
1835                1840                1845

Leu Thr Ser Pro Ser Glu Gln Leu Thr Ser Asn Gln Ser Asn Gln
1850                1855                1860

Gln Leu Pro Leu Leu Ser Asn Ser Gln Lys Leu Ala Ser Cys Gln
1865                1870                1875

Val Glu Asp Glu Arg His Pro Glu Ala Asp Glu Pro Gln His Pro
1880                1885                1890

Glu Asp Asp Asn Leu Pro Gln Leu Asp Glu Phe Trp Ser Asp Ser
1895                1900                1905

Glu Glu Ile Tyr Ala Asp Pro Ser Phe Gly Gly Val Ala Ile Ala
1910                1915                1920

Pro Ile His Gly Ser Val Leu Ile Glu Cys Ala Arg Lys Glu Leu
1925                1930                1935

His Ala Thr Thr Ser Leu Arg Ser Pro Lys Arg Gly Val Pro Phe
1940                1945                1950

Arg Val Ser Leu Val Phe Tyr Gln His Lys Ser Leu Asn Lys Pro
1955                1960                1965

Asn His Gly Phe Asp Ile Asn Lys Ile Lys Cys Lys Cys Lys Lys
1970                1975                1980

Val Thr Lys Lys Lys Pro Ala Asp Arg Glu Cys Pro Asp Val Ser

```
                    1985                1990                1995
Pro  Glu  Ala  Asn  Leu  Ser  His  Gln  Ile  Pro  Ser  Arg  Val  Ala  Ser
               2000                2005                2010

Thr  Leu  Thr  Arg  Asp  Asn  Val  Val  Thr  Val  Ser  Pro  Tyr  Ser  Leu
               2015                2020                2025

Thr  His  Val  Ala  Gly  Pro  Tyr  Asn  Arg  Trp  Val
               2030                2035

<210> SEQ ID NO 2
<211> LENGTH: 375
<212> TYPE: PRT
<213> ORGANISM: Artificial Sequence
<220> FEATURE:
<223> OTHER INFORMATION: Synthetic peptide

<400> SEQUENCE: 2

Ser  His  His  His  His  His  Ser  Ser  Gly  Val  Asp  Leu  Gly  Thr  Glu
1                   5                   10                  15

Asn  Leu  Tyr  Phe  Gln  Ser  Asn  Ala  Met  Lys  Ile  Ala  Ile  Asn  Met
               20                  25                  30

Gly  Asn  Asn  Val  Ile  Asn  Phe  Lys  Thr  Val  Pro  Ser  Ser  Glu  Thr  Ile
               35                  40                  45

Tyr  Leu  Phe  Lys  Val  Ile  Ser  Glu  Met  Gly  Leu  Asn  Val  Asp  Ile  Ile
     50                  55                  60

Ser  Leu  Lys  Asn  Gly  Val  Tyr  Thr  Lys  Ser  Phe  Asp  Glu  Val  Asp  Val
65                  70                  75                  80

Asn  Asp  Tyr  Asp  Arg  Leu  Ile  Val  Val  Asn  Ser  Ser  Ile  Asn  Phe  Phe
                    85                  90                  95

Gly  Gly  Lys  Pro  Asn  Leu  Ala  Ile  Leu  Ser  Ala  Gln  Lys  Phe  Met  Ala
               100                 105                 110

Lys  Tyr  Lys  Ser  Lys  Ile  Tyr  Tyr  Leu  Phe  Thr  Asp  Ile  Arg  Leu  Pro
               115                 120                 125

Phe  Ser  Gln  Ser  Trp  Pro  Asn  Val  Lys  Asn  Arg  Pro  Trp  Ala  Tyr  Leu
     130                 135                 140

Tyr  Thr  Glu  Glu  Glu  Leu  Leu  Ile  Lys  Ser  Pro  Ile  Lys  Val  Ile  Ser
145                 150                 155                 160

Gln  Gly  Ile  Asn  Leu  Asp  Ile  Ala  Lys  Ala  Ala  His  Lys  Lys  Val  Asp
                    165                 170                 175

Asn  Val  Ile  Glu  Phe  Glu  Tyr  Phe  Pro  Ile  Glu  Gln  Tyr  Lys  Ile  His
               180                 185                 190

Met  Asn  Asp  Phe  Gln  Leu  Ser  Lys  Pro  Thr  Lys  Thr  Leu  Asp  Val
               195                 200                 205

Ile  Tyr  Gly  Gly  Ser  Phe  Arg  Ser  Gly  Gln  Arg  Glu  Ser  Lys  Met  Val
     210                 215                 220

Glu  Phe  Leu  Phe  Asp  Thr  Gly  Leu  Asn  Ile  Glu  Phe  Phe  Gly  Asn  Ala
225                 230                 235                 240

Arg  Glu  Lys  Gln  Phe  Lys  Asn  Pro  Lys  Tyr  Pro  Trp  Thr  Lys  Ala  Pro
                    245                 250                 255

Val  Phe  Thr  Gly  Lys  Ile  Pro  Met  Asn  Met  Val  Ser  Glu  Lys  Asn  Ser
               260                 265                 270

Gln  Ala  Ile  Ala  Ala  Leu  Ile  Gly  Asp  Lys  Asn  Tyr  Asn  Asp  Asn
               275                 280                 285

Phe  Ile  Thr  Leu  Arg  Val  Trp  Glu  Thr  Met  Ala  Ser  Asp  Ala  Val  Met
     290                 295                 300

Leu  Ile  Asp  Glu  Glu  Phe  Asp  Thr  Lys  His  Arg  Ile  Ile  Asn  Asp  Ala
```

```
                305                 310                 315                 320
Arg Phe Tyr Val Asn Asn Arg Ala Glu Leu Ile Asp Arg Val Asn Glu
                325                 330                 335

Leu Lys His Ser Asp Val Leu Arg Lys Glu Met Leu Ser Ile Gln His
            340                 345                 350

Asp Ile Leu Asn Lys Thr Arg Ala Lys Lys Ala Glu Trp Gln Asp Ala
        355                 360                 365

Phe Lys Lys Ala Ile Asp Leu
    370                 375

<210> SEQ ID NO 3
<211> LENGTH: 76
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (29)..(49)
<223> OTHER INFORMATION: N = 5hmC

<400> SEQUENCE: 3
cctcaccatc tcaaccaata ttatattang ngtatatngn gtatttngng ttataatatt    60
gagggagaag tggtga                                                   76

<210> SEQ ID NO 4
<211> LENGTH: 15
<212> TYPE: DNA
<213> ORGANISM: Artificial Sequence
<220> FEATURE:
<223> OTHER INFORMATION: Synthetic primer

<400> SEQUENCE: 4
atttgcataa caatg                                                    15

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
atagtgccac ctggtggcca                                               20

<210> SEQ ID NO 6
<211> LENGTH: 10
<212> TYPE: DNA
<213> ORGANISM: Artificial Sequence
<220> FEATURE:
<223> OTHER INFORMATION: Synthetic primer

<400> SEQUENCE: 6
ggccattaac                                                          10

<210> SEQ ID NO 7
<211> LENGTH: 76
<212> TYPE: DNA
<213> ORGANISM: Artificial Sequence
<220> FEATURE:
<223> OTHER INFORMATION: Synthetic primer

<400> SEQUENCE: 7
cctcaccatc tcaaccaata ttatattatg tgtatatcgc gtattttgtg ttataatatt    60
```

-continued

```
gagggagaag tggtga                                              76

<210> SEQ ID NO 8
<211> LENGTH: 76
<212> TYPE: DNA
<213> ORGANISM: Artificial Sequence
<220> FEATURE:
<223> OTHER INFORMATION: Synthetic primer

<400> SEQUENCE: 8
cctcaccatc tcaaccaata ttatattacg cgtatatcgc gtatttcgcg ttataatatt    60
gagggagaag tggtga                                              76

<210> SEQ ID NO 9
<211> LENGTH: 30
<212> TYPE: DNA
<213> ORGANISM: Artificial Sequence
<220> FEATURE:
<223> OTHER INFORMATION: Synthetic primer

<400> SEQUENCE: 9 ccctttatt attttaatta atattatatt                                30

<210> SEQ ID NO 10
<211> LENGTH: 19
<212> TYPE: DNA
<213> ORGANISM: Artificial Sequence
<220> FEATURE:
<223> OTHER INFORMATION: Synthetic primer

<400> SEQUENCE: 10
tcaccacttc tccctcaat                                           19

<210> SEQ ID NO 11
<211> LENGTH: 77
<212> TYPE: DNA
<213> ORGANISM: Artificial Sequence
<220> FEATURE:
<223> OTHER INFORMATION: Synthetic primer

<400> SEQUENCE: 11
cctcaccatc tcaaccaata ttatattatg tgtatattmc gatatttgt gttataatat    60 tgagggagaa gtggtga                                             77

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
cctcaccatc tcaaccaata                                          20

<210> SEQ ID NO 13
<211> LENGTH: 30
<212> TYPE: DNA
<213> ORGANISM: Artificial Sequence
<220> FEATURE:
<223> OTHER INFORMATION: Synthetic primer

<400> SEQUENCE: 13 ccctttatt attttaatta atattatatt                                30
```

<210> SEQ ID NO 14
<211> LENGTH: 80
<212> TYPE: DNA
<213> ORGANISM: Artificial Sequence
<220> FEATURE:
<223> OTHER INFORMATION: Synthetic primer

<400> SEQUENCE: 14
ctccgacatt atcactacca tcaaccaccc atcctacctg gactacattc ttattcagta    60
ttcaccactt ctccctcaat                                                80

<210> SEQ ID NO 15
<211> LENGTH: 55
<212> TYPE: DNA
<213> ORGANISM: Artificial Sequence
<220> FEATURE:
<223> OTHER INFORMATION: Synthetic primer

<400> SEQUENCE: 15
ccatctcatc cctgcgtgtc tccgactcag aatttggtgg tgagtaatgg tttta          55

<210> SEQ ID NO 16
<211> LENGTH: 48
<212> TYPE: DNA
<213> ORGANISM: Artificial Sequence
<220> FEATURE:
<223> OTHER INFORMATION: Synthetic primer

<400> SEQUENCE: 16
cctctctatg ggcagtcggt gataacctac cccaacacct atttaaat                  48

<210> SEQ ID NO 17
<211> LENGTH: 58
<212> TYPE: DNA
<213> ORGANISM: Artificial Sequence
<220> FEATURE:
<223> OTHER INFORMATION: Synthetic primer

<400> SEQUENCE: 17
ccatctcatc cctgcgtgtc tccgactcag tagaagtaaa ggaagtaaag gaagtatg       58

<210> SEQ ID NO 18
<211> LENGTH: 48
<212> TYPE: DNA
<213> ORGANISM: Artificial Sequence
<220> FEATURE:
<223> OTHER INFORMATION: Synthetic primer

<400> SEQUENCE: 18
cctctctatg ggcagtcggt gataaaccta aataataaca aacacacc                  48

<210> SEQ ID NO 19
<211> LENGTH: 56
<212> TYPE: DNA
<213> ORGANISM: Artificial Sequence
<220> FEATURE:
<223> OTHER INFORMATION: Synthetic primer

<400> SEQUENCE: 19
ccatctcatc cctgcgtgtc tccgactcag gaagttgtat aaaattttg gatgtg          56

<210> SEQ ID NO 20
<211> LENGTH: 48
<212> TYPE: DNA
<213> ORGANISM: Artificial Sequence

```
<220> FEATURE:
<223> OTHER INFORMATION: Synthetic primer

<400> SEQUENCE: 20
cctctctatg ggcagtcggt gatcctctcc tatctccctt aactactc                48

<210> SEQ ID NO 21
<211> LENGTH: 28
<212> TYPE: DNA
<213> ORGANISM: Artificial Sequence
<220> FEATURE:
<223> OTHER INFORMATION: Synthetic primer

<400> SEQUENCE: 21 tttgatttttt gtgtttagta gttttgtg                                     28

<210> SEQ ID NO 22
<211> LENGTH: 25
<212> TYPE: DNA
<213> ORGANISM: Artificial Sequence
<220> FEATURE:
<223> OTHER INFORMATION: Synthetic primer

<400> SEQUENCE: 22
cctcctcaat tttaaaatct attcc                                         25

<210> SEQ ID NO 23
<211> LENGTH: 25
<212> TYPE: DNA
<213> ORGANISM: Artificial Sequence
<220> FEATURE:
<223> OTHER INFORMATION: Synthetic primer

<400> SEQUENCE: 23
tttaggaatt gataggtagt tgtag                                         25

<210> SEQ ID NO 24
<211> LENGTH: 27
<212> TYPE: DNA
<213> ORGANISM: Artificial Sequence
<220> FEATURE:
<223> OTHER INFORMATION: Synthetic primer

<400> SEQUENCE: 24
aaacacaaac aatcttacaa aaaaaaa                                       27

<210> SEQ ID NO 25
<211> LENGTH: 26
<212> TYPE: DNA
<213> ORGANISM: Artificial Sequence
<220> FEATURE:
<223> OTHER INFORMATION: Synthetic primer

<400> SEQUENCE: 25
tttgggttat gtaagttgat tttatg                                        26

<210> SEQ ID NO 26
<211> LENGTH: 25
<212> TYPE: DNA
<213> ORGANISM: Artificial Sequence
<220> FEATURE:
<223> OTHER INFORMATION: Synthetic primer

<400> SEQUENCE: 26
caccctactt actaaaattt acacc                                         25
```

COMPOSITION AND METHODS RELATED TO MODIFICATION OF 5-METHYLCYTOSINE (5-MC)

The present application is a national phase application under 35 U.S.C. §371 of International Application No. PCT/US2012/032489 filed Apr. 6, 2012, which claims priority to U.S. provisional patent application 61/472,435 filed on Apr. 6, 2011, and U.S. provisional patent application 61/512,334 filed on Jul. 27, 2011, each of which are hereby incorporated by reference in its entirety. This application is related to U.S. Provisional application Ser. No. 61/321,198 filed Apr. 6, 2010 and PCT application PCT/US2011/031370 filed Apr. 6, 2011, each of which is incorporated herein by reference in its entirety.

The present invention relates generally to the field of molecular biology. More particularly, it concerns methods and compositions for modifying 5-methylcytosine (5mC) and/or 5-hydroxymethylcytosine (5hmC) and subsequently detecting, evaluating, sequencing, and/or mapping 5-methyl-modified as well as 5-hydroxymethyl-modified cytosine bases within a nucleic acid molecule.

BACKGROUND OF THE INVENTION 5-methylcytosine (5mC) is a vital epigenetic marker that affects a broad range of biological functions in mammals, including gene expression, maintenance of genome integrity, parental imprinting, X-chromosome inactivation, and regulation of development, aging and cancer (Deaton and Bird, 2011; De Carvalho et al., 2010; Bird, 2002; Jaenisch and Bird, 2003; Goll and Bestor, 2005). Moreover, abnormal methylation of specific gene promoter regions can lead to diseases such as various cancer (Berman et al., 2012; Jones and Baylin, 2002; Esteller, 2007; Feinberg and Tycko, 2004). 5-methylcytosine (5mC) is catalyzed and maintained by a family of DNA methyltransferases (DNMTs) in eukaryotes (Law and Jacobesen, 2010), and constitutes ~3-6% of the total cytosines in human genomic DNA (Esteller and Aberrant, 2005).

To date, numerous methods have been developed to profile and analyze the global DNA methylation (methylome) in eukaryotes cells (Bock, 2009; Feinberg and Vogelstein, 1983; Beck and Rakyan, 2008). Current technologies for detecting DNA methylation are generally of two types. In the first type, DNA fragments containing 5mC are enriched using affinity-based capture, including the use of 5-methycytosine-binding proteins (MBD-Seq) and antibody-based approaches (e.g. methylated DNA immunoprecipitation, MeDIP-seq). In the other type, denatured DNA is treated with sodium bisulfite, such that non-modified cytosine is converted to uracil, while methylated cytosine is left intact, allowing for base-resolution detection of cytosine methylation. In recent years, the study of 5mC has been facilitated by the development of whole genome bisulfite sequencing methods that can resolve the genomic location of methylcytosine at single-base resolution (Cokus et al., 2008; Lister et al., 2008; Lister et al., 2009).

However, the recent discovery that 5mC can be iteratively oxidized to 5-hydroxymethyl (5hmC), 5-formyl (5fC), and 5-carboxylcytosine (5caC) (He et al., 2011; Ito et al., 2011) requires reevaluation of the specificity of various approaches for each type of modified cytosine. Indeed, sodium bisulfite treatment, the previously held "gold standard" for DNA methylation analyses, cannot distinguish 5mC from 5hmC (Huang et al., 2010; Jin et al., 2010), but does allow for deamination of 5caC. Thus, methods relying on sodium bisulfite treatment, such as whole genome bisulfite sequencing (MethylC-Seq), reduced representation bisulfite sequencing (RRBS), and array-based approaches, generate maps of both 5mC and 5hmC, rather than 5mC specifically. As a result, further technology development is needed in order to allow proper interpretation of the signals produced by such methods.

All of these approaches have additional limitations: the bisulfite conversion-based methods (e.g. reduced representation bisulfite sequencing, RRBS) are typically associated with high costs and cannot distinguish between 5mC and recently discovered 5-hydroxylmethycytosine (5hmC) (Meissner et al., 2008; Harris et al., 2010); array-based approaches (e.g. Illumina's Infinium assay) provide low genome coverage (~0.1%) (Weisenberger et al., 2008; Beck, 2010). Moreover, affinity-based methods, such as MBD and MeDIP, can be specific for 5mC but cannot supply information on hypomethylated CpG and non-CpG methylation regions (Jacinto et al., 2008; Bock et al., 2010).

Therefore, alternative methods and compositions for detecting and evaluating 5mC in the genome of eukaryotic organisms are desirable.

In 2009, the presence of an oxidized 5mC, 5-hydroxymethylcytosine (5hmC), has been discovered in embryonic and neuronal stem cells, certain adult brain cells, and some cancer cells. 5hmC was discovered as another relatively abundant form of cytosine modification in embryonic stem cells (ESCs) and Purkinje neurons (Kriaucionis and Heintz, 2009; Tahiliani et al., 2009). It has been widely accepted that 5hmC is another player of epidenetic regulation and potential disease marker.

The TET proteins, which are responsible for conversion of 5mC to 5hmC, have been shown to function in ESC regulation, myelopoiesis and zygote development (Dawlaty et al., 2011; Gu et al., 2011; Iqbal et al., 2011; Ito et al., 2010; Ko et al., 2010; Koh et al., 2011; Wossidlo et al., 2011). 5hmC was found to be widespread in many tissues and cell types, although with diverse levels of abundance (Globisch et al., 2010; Munzel et al., 2010; Song et al., 2011; Szwagierczak et al., 2010). Proteins that can recognize 5hmC-containing DNA have also been investigated (Frauer et al., 2011; Yildirim et al., 2011). In addition, 5hmC can be further oxidized to 5-formylcytosine (5fC) and 5-carboxylcytosine (5caC) by TET proteins (He et al., 2011; Ito et al., 2011; Pfaffeneder et al., 2011), and demethylation pathways through these modified cytosines have been shown (Cortellino et al., 2011; Guo et al., 2011; He et al., 2011; Maiti and Drohat, 2011; Zhang et al., 2012). Together, these studies provide an emerging paradigm in which 5mC oxidation plays important roles in sculpting a cell's epigenetic landscape and developmental potential through the regulation of dynamic DNA methylation states.

Strategies to selectively label and/or enrich 5hmC in genomic DNA have been developed to investigate the distribution and function of 5hmC in the genome (Pastor et al., 2011; Robertson et al., 2012; Robertson et al., 2011; Song et al., 2011), which also include 5hmC immunoprecipitation (hMeDIP) by employing antibodies (Ficz et al., 2011; Stroud et al., 2011; Williams et al., 2011; Wu et al., 2011; Xu et al., 2011). While 5hmC is more highly enriched in gene bodies than transcription starting sites in mouse cerebellum (Song et al., 2011; Szulwach et al., 2011b), all genome-wide maps of 5hmC in human and mouse embryonic stem cells indicate that 5hmC tends to exist in gene bodies, promoters, and enhancers (Ficz et al., 2011; Pastor et al., 2011; Stroud et al., 2011; Szulwach et al., 2011a; Williams et al., 2011; Wu et al., 2011; Xu et al., 2011). However, in all cases, the resolution of these maps was restricted by the size of the immunoprecipitated or chemically captured DNA, which varied from several hundred to over a thousand bases.

Since current bisulfite sequencing methods cannot distinguish between 5mC and 5hmC (Huang et al., 2010; Jin et al., 2010), the genome-wide bisulfite sequencing maps generated in recent years may not accurately capture the true abundance of 5mC at each base in the genome. A more detailed understanding of the function of 5hmC as well as 5mC has, therefore, been hampered by the lack of a single-base resolution sequencing technology capable of detecting the relative abundance of 5hmC per cytosine.

Therefore, there is also a need for methods and compositions for detecting and evaluating 5hmC in a nucleic acid molecule as well as in the genome of eukaryotic organisms.

SUMMARY OF THE INVENTION

The inability to easily and efficiently detect or measure 5-methylcytosine (5mC) and/or 5-hydroxylmethylcytosine (5hmC) presents challenges to studying and understanding the significance and function of endogenous 5mC and/or 5hmC in genomic DNA. Most current approaches for global methylome profiling have drawbacks of either high costs and time-consuming or being ineffective for less densely populated 5mC sites. Therefore, a robust, low cost, sequence unbiased approach for straightforward global methylome profiling with complete genome coverage is highly desirable to facilitate interpretation of multiple DNA methylation in a locus specific and genome-wide manner and to profile mehtylomes in future disease diagnostics. In addition, to elucidate the distinct biological roles of 5hmC and 5mC, respectively, it is desirable to develop efficient analytical technologies to distinguish 5hmC from 5mC. Solutions that provide additional methods and techniques for detection or mapping of the methylation state of nucleic acids opens the door to additional diagnostic and therapeutic applications. Accordingly, methods and compositions are provided and described.

Certain embodiments are directed to detection of 5mC by modifying 5mC by oxidizing 5mC to 5hmC. The approach includes one, two, three, or four of the following steps. (1) Labeling 5hmC in a nucleic acid with a first glucose, a first modified glucose as described herein, or blocking 5hmC from further modification or allowing differential detection of 5hmC labeled in at least two different 5hmC labeling reactions. (2) Oxidizing 5mC to 5hmC. In one example, oxidation of 5mC to 5hmC can be accomplished by contacting the modified nucleic acid of step 1 with a methylcytosine dioxygenases (e.g., TET1, TET2 and TET3) or an enzyme having similar activity. (3) Labeling 5hmC generated by step 2 with a second labeled or modified glucose that can be differentiated from that used for labeling of 5hmC present prior to the oxidation step in the same nucleic acid. (4) Enriching and/or detecting 5hmC generated in step 2, e.g., by affinity chromatography, for detection, sequencing and diagnostic applications. The approach described herein also involves combining step (2) and step (3) into one step, i.e., the oxidization of 5mC to 5hmC and the modification of generated 5hmC occur in one step.

Certain embodiments are directed to methods for detecting 5mC in a nucleic acid comprising converting 5mC to a modified 5mC, such as 5-hydroxymethylcytosine and detecting 5-hydroxymethylcytosine. In certain aspects, the 5-methylcytosine is converted to 5-hydroxymethylcytosine using enzymatic modification by a methylcytosine dioxygenase or the catalytic domain of a methylcytosine dioxygenase. In a further aspect, a methylcytosine dioxygenase is TET1, TET2, or TET3, or a homologue thereof. In particular embodiments, a methylcytosine dioxygenase comprises amino acids 1367-2039 of SEQ ID NO: 1.

A polypeptide is considered as a homologue to another polypeptide when two polypeptides have at least 75% sequence identity. Preferably, the sequence identity level is 80% or 85%, more preferred 90% or 95%, and yet more preferred 98% or 99%. Similarly, a polynucleotide is considered as a homologue to another polynucleotide when two polynucleotides have at least 75% sequence identity. Preferably, the sequence identity level is 80% or 85%, more preferred 90% or 95%, and yet more preferred 98% or 99%.

In certain aspects the methods further comprise modifying 5-hydroxymethylcytosine with a detectable label or a detectable functional group. The detectable label can be a fluorescent, radioactive, enzymatic, electrochemical, or colorimetric label. In certain aspects the 5-hydroxymethylcytosine is modified with a glucose or a modified glucose molecule. In a further aspect the glucose or modified glucose is coupled to a detectable label.

Certain embodiments are directed to methods for detecting 5mC in a nucleic acid molecule comprising incubating the nucleic acid molecule with a methylcytosine dioxygenase, a β-glucosyltransferase and a glucose or modified glucose molecule. In certain aspects, the modified glucose molecule is uridine diphospho6-$N_3$-glucose molecule. In further aspects, the 5-hydroxymethylcytosine is converted to 6-$N_3$-β-glucosyl-5-hydroxymethyl-cytosine ($N_3$-5gmC).

In certain embodiments, the methods further comprise modifying $N_3$-5gmC with a detectable label or a detectable functional group. The detectable label can be a fluorescent, radioactive, enzymatic, electrochemical, or colorimetric label. The $N_3$-5gmC may be coupled to a detectable label using an enzymatic method. In additional aspects, the $N_3$-5gmC is coupled to a detectable label by using a chemical method. In particular aspects, the chemical method is click chemistry. In further aspects, the detectable label is biotin. In additional aspects, the $N_3$-5gmC is coupled to a biotin on its azide group.

Certain embodiments are directed to methods wherein the hydroxyl group of the 5-hydroxymethylcytosine is converted to an aldehyde group or carboxyl group.

In certain aspects the hydroxyl group is modified using an enzymatic or chemical method.

The methods can further comprise modifying 5hmC in the nucleic acid composition prior to converting 5mC to a 5hmC. In certain embodiments, the 5hmC is modified with a glucose or a modified glucose, comprising incubating the nucleic acid molecule with a β-glucosyltransferase and a glucose or modified glucose molecule. In certain aspects, the glucose molecule is a uridine diphosphoglucose molecule. In further aspects, the modified glucose molecule is a modified uridine diphosphoglucose molecule.

In certain aspects the methods further comprise modifying 5hmC with a first detectable label or a first detectable functional group. In certain aspects a converted or modified 5-methylcytosine is labeled with a second detectable label. The method can also include a step of detecting differential labeling of the nucleic acid with the first and second label. The label or detectable label can be a fluorescent, radioactive, enzymatic, electrochemical, or colorimetric label. In certain aspects the hydroxyl group of a modified 5mC is further converted to a functional group selected from an aldehyde or carboxyl group, which may in turn be coupled to a label or detectable label. The functional group, e.g., hydroxyl group, of modified 5mC can be further modified using an enzymatic method, such as modification by alcohol dehydrogenase. The functional group, e.g., hydroxyl group, of modified 5mC can be further modified using a chemical method, such as modification by pyridinium chlorochromate (PCC). In certain aspects 5hmC, endogenous and/or modified, is glucosylated. The glucosylated 5hmC (5gmC) can comprise a first, second, and or third label, or more. In certain aspects the label is fluorescent, radioactive, enzymatic, electrochemical, or colorimetric.

In certain aspects the nucleic acid molecule is DNA, genomic DNA, or RNA. In particular embodiments, the nucleic acid molecule is isolated, such as away from non-nucleic acid cellular material and/or away from other nucleic acid molecules.

Methods may involve any of the following steps described herein. In some embodiments, methods involve incubating the nucleic acid molecule with an agent that modifies 5mC in a target nucleic acid molecule. In other embodiments, methods may involve mixing the nucleic acids with a modifying agent and/or a label or other detectable moiety under conditions to promote modification of the 5mC in a target nucleic acid. Labels or detectable moieties can be either directly or indirectly measured, detected, or quantified. It is specifically contemplated that reactions involving any enzymes may be restricted or limited by time, enzyme concentration, substrate concentration, and/or template concentration. For example, there may be a partial restriction enzyme digest or partial modification of nucleic acid molecules. Reaction conditions may be adjusted so that the reaction is carried out under conditions that result in about, at least about, or at most about 20, 30, 40, 50, 60, 70, 80, 90, 95, 96, 97, 98, 99, 100% of 5mC being modified, or any range derivable therein.

In some embodiments, methods may also involve one or more of the following regarding nucleic acids prior to and/or concurrent with 5mC modification of nucleic acids: obtaining nucleic acid molecules; obtaining nucleic acid molecules from a biological sample; obtaining a biological sample containing nucleic acids from a subject; isolating nucleic acid molecules; purifying nucleic acid molecules; obtaining an array or microarray containing nucleic acids to be modified; denaturing nucleic acid molecules; shearing or cutting nucleic acid; denaturing nucleic acid molecules; hybridizing nucleic acid molecules; incubating the nucleic acid molecule with an enzyme that does not modify 5mC; incubating the nucleic acid molecule with a restriction enzyme; attaching one or more chemical groups or compounds to the nucleic acid or 5mC or modified 5mC; conjugating one or more chemical groups or compounds to the nucleic acid or 5mC or modified 5mC; incubating nucleic acid molecules with an enzyme that modifies the nucleic acid molecules or 5mC or modified 5mC by adding or removing one or more elements, chemical groups, or compounds.

Methods may further involve one or more of the following steps that is concurrent with and/or subsequent to modification of nucleic acids: isolating nucleic acids with modified 5mC; isolating modified nucleic acids based on the modification to 5mC; purifying modified 5mC nucleic acids based on the modification, label, or moiety coupled to 5mC (coupling can be either covalent or non-covalent coupling); reacting the modified 5mC in the modified nucleic acid molecule with a detectable or functional moiety, such as a linker; conjugating or attaching a detectable or functional moiety to the modified 5mC nucleotide; exposing to, incubating with, or mixing with the modified nucleic acid an enzyme that will use the modified nucleic acid as a substrate independent of the modification to 5mC; exposing to, incubating with, or mixing with the modified nucleic acid an enzyme that will use the modified nucleic acid as a substrate unless the modification to the 5mC modifies, alters, prevents, or hinders it; exposing to, incubating with, or mixing with the modified nucleic acid an enzyme that will use the modified nucleic acid as a substrate unless the modification sterically prevents or inhibits the enzyme; enriching for nucleic acids containing modified nucleic acids; identifying 5mC in the nucleic acids using the modified 5mC molecule, identifying 5mC in the nucleic acid by comparing glycosylated nucleic acids with unmodified nucleic acids; mapping the 5mC in the nucleic acid molecule; subjecting the modified nucleic acid to chromatography; subjecting the modified nucleic acid to a primer extension assay and comparing the results to a control nucleic acid; subjecting the modified nucleic acid to a hybridization assay and comparing the results to a control nucleic acid; and/or sequencing the glycosylated nucleic acid and comparing the results to a control nucleic acid.

Methods may also involve the following steps: modifying or converting a 5mC to 5-hydroxymethylcytosine (5hmC); modifying 5hmC using β-glucosyltransferase (βGT); incubating β-glucosyltransferase with UDP-glucose molecules and a nucleic acid substrate under conditions to promote glycosylation of the nucleic acid with the glucose molecule (which may or may not be modified) and result in a nucleic acid that is glycosylated at one or more 5-hydroxymethylcytosines.

It is contemplated that some embodiments will involve steps that are done in vitro, such as by a person or a person controlling or using machinery to perform one or more steps.

Methods and compositions may involve a purified nucleic acid, modification reagent or enzyme, label, chemical modification moiety, modified UDP-Glc, and/or enzyme, such as β-glucosyltransferase. Such protocols are known to those of skill in the art.

In certain embodiments, purification may result in a molecule that is about or at least about 70, 75, 80, 85, 90, 95, 96, 97, 98, 99, 99.1, 99.2, 99.3, 99.4, 99.5, 99.6, 99.7 99.8, 99.9% or more pure, or any range derivable therein, relative to any contaminating components (w/w or w/v).

In other methods, there may be steps including, but not limited to, obtaining information (qualitative and/or quantitative) about one or more 5mCs and/or 5hmCs in a nucleic acid sample; ordering an assay to determine, identify, and/or map 5mCs and/or 5hmCs in a nucleic acid sample; reporting information (qualitative and/or quantitative) about one or more 5mCs and/or 5hmCs in a nucleic acid sample; comparing that information to information about 5mCs and/or 5hmCs in a control or comparative sample. Unless otherwise stated, the terms "determine," "analyze," "assay," and "evaluate" in the context of a sample refer to transformation of that sample to gather qualitative and/or quantitative data about the sample. Moreover, the term "map" means to identify the location within a nucleic acid sequence of the particular nucleotide.

In some embodiments, nucleic acid molecules may be DNA, RNA, or a combination of both. Nucleic acids may be recombinant, genomic, or synthesized. In additional embodiments, methods involve nucleic acid molecules that are isolated and/or purified. The nucleic acid may be isolated from a cell or biological sample in some embodiments. Certain embodiments involve isolating nucleic acids from a eukaryotic, mammalian, or human cell. In some cases, they are isolated from non-nucleic acids. In some embodiments, the nucleic acid molecule is eukaryotic; in some cases, the nucleic acid is mammalian, which may be human. This means the nucleic acid molecule is isolated from a human cell and/or has a sequence that identifies it as human. In particular embodiments, it is contemplated that the nucleic acid molecule is not a prokaryotic nucleic acid, such as a bacterial nucleic acid molecule. In additional embodiments, isolated nucleic acid molecules are on an array. In particular cases, the array is a microarray. In some cases, a nucleic acid is isolated by any technique known to those of skill in the art, including, but not limited to, using a gel, column, matrix or filter to isolate the nucleic acids. In some embodiments, the gel is a polyacrylamide or agarose gel.

Methods and compositions may also include a modified 5mC. In some embodiments, the modified 5mC comprises a modification moiety. In some embodiments, more than one modification moiety is included. The term "modification moiety" refers to a chemical compound or element that is added to a 5mC. A modified 5mC refers to a 5mC molecule having (i) a modification moiety or (ii) a chemical compound or element that is substituted for or covalently coupled to a 5mC, such that the resulting modified compound has a different chemical formula than unmodified 5mC. It is specifically contemplated that a modified 5mC does not include a 5mC that is radioactive by substitution of a molecule or compound in a 5mC with the same molecule or compound, for example, a molecule or compound that is merely radioactive. In certain embodiments a 5hmC molecule is specifically excluded or included as a modified 5mC.

In certain embodiments, modified 5mC or a modification moiety may comprise one or more detectable moieties. A detectable moiety refers to a chemical compound or element that is capable of being detected. In particular embodiments, a modified 5mC is not a version of 5mC that is radioactive, and in specific embodiments, a modified 5mC does not have a radioactive carbon molecule. In certain embodiments, a detectable moiety is fluorescent, radioactive, enzymatic, electrochemical, or colorimetric. In some embodiments, the detectable moiety is a fluorophore or quantum dot.

In some embodiments, a modification moiety may be a linker that allows one or more functional or detectable moieties or isolation tags to be attached to the modified 5mC containing molecules. In some embodiments the linker is an azide linker or a thiol linker. In further embodiments, the modification moiety may be an isolation tag, which means the tag can be used to isolate a molecule that is attached to the tag. In certain embodiments, the isolation tag is biotin or a histidine tag. In some cases, the tag is modified, such as with a detectable moiety. It is contemplated that the linker allows for other chemical compounds or substances to be attached to the modified nucleic acid at 5mC. In other embodiments, a functional moiety is attached to the target molecule after 5mC has be modified. In certain embodiments one or more functional and/or detectable moieties and/or isolation tags are attached to each 5mC nucleotides.

In further embodiments, a functional moiety comprises a molecule or compound that inhibits or blocks an enzyme from using the 5mC in the nucleic acid molecule as a substrate. In some embodiments, the inhibition is sufficiently complete to prevent detection of an enzymatic reaction involving the 5mC. It is contemplated that the molecule or compound that blocks an enzyme may be doing this by sterically blocking access of the enzyme. Such sterical blocking moieties are specifically contemplated as modification moieties. In specific embodiments, the sterical blocking moieties contain 1, 2, or 3 ringed structures, including but not limited to aromatic ring structures. In certain embodiments the blocking moiety is polyethylene glycol. In other embodiments, it is a nucleic acid, amino acid, carbohydrate, or fatty acid (including mono-, di-, or tri-versions).

Methods and compositions may also involve one or more enzymes. In some embodiments, the enzyme is a restriction enzyme or a polymerase. In certain cases, embodiments involve a restriction enzyme. The restriction enzyme may be methylation-insensitive. In other embodiments, the enzyme is polymerase. In certain embodiments, nucleic acids are contacted with a restriction enzyme prior to, concurrent with, or subsequent to modification of 5mC. The modified nucleic acid may be contacted with a polymerase before or after the nucleic acid has been exposed to a restriction enzyme.

Methods and compositions involve detecting, characterizing, and/or distinguishing between methylcytosine after modifying the 5mC. Methods may involve identifying 5mC in the nucleic acids by comparing modified nucleic acids with unmodified nucleic acids or to nucleic acids whose modification state is already known. Detection of the modification can involve a wide variety of recombinant nucleic acid techniques. In some embodiments, a modified nucleic acid molecule is incubated with polymerase, at least one primer, and one or more nucleotides under conditions to allow polymerization of the modified nucleic acid. In additional embodiments, methods may involve sequencing a modified nucleic acid molecule. In other embodiments, a modified nucleic acid is used in a primer extension assay.

Methods and compositions may involve a control nucleic acid. The control may be used to evaluate whether modification or other enzymatic or chemical reactions are occurring. Alternatively, the control may be used to compare modification states. The control may be a negative control or it may be a positive control. It may be a control that was not incubated with one or more reagents in the modification reaction. Alternatively, a control nucleic acid may be a reference nucleic acid, which means its modification state (based on qualitative and/or quantitative information related to modification at 5mCs, or the absence thereof) is used for comparing to a nucleic acid being evaluated. In some embodiments, multiple nucleic acids from different sources provide the basis for a control nucleic acid. Moreover, in some cases, the control nucleic acid is from a normal sample with respect to a particular attribute, such as a disease or condition, or other phenotype. In some embodiments, the control sample is from a different patient population, a different cell type or organ type, a different disease state, a different phase or severity of a disease state, a different prognosis, a different developmental stage, etc.

Certain embodiments involve identifying 5mC in genomic DNA comprising: (a) isolating the genomic DNA; (b) processing the genomic DNA into pieces; (c) incubating genomic DNA pieces with a modification agent and a modification moiety under the conditions to modify 5hmC with the modification moiety; (d) incubating the genomic DNA pieces from (c) with a methylcytosine dioxygenase, a modification agent and a modification moiety under the conditions that modifying the 5mC in the genomic DNA by converting 5mC to 5hmC and transferring the modification moiety to 5hmC; (e) identifying 5mC in the genomic DNA by detecting 5hmC using the introduced modification. In certain aspects, the modification agent is a β-glucosyltransferase and the modification moiety is a glucose or a modified glucose molecule. In particular embodiments, the modified glucose molecule in step (d) is uridine diphospho6-$N_3$-glucose. In additional embodiments, the 5mC is converted to 6-$N_3$-β-glucosyl-5-hydroxymethyl-cytosine ($N_3$-5gmC) in step (d). Certain embodiments also involve attaching a chemical label to the azide group of $N_3$-5gmC. In certain aspects, the chemical label is biotin.

Certain embodiments involve methods for mapping 5mC in a nucleic acid molecule comprising (a) incubating the nucleic acid molecule with a modification agent and a modification moiety to modify 5hmC in the nucleic acid molecule with the modification moiety; (b) incubating the nucleic acid molecule from (a) with a methylcytosine dioxygenase, a modification agent, and a modification moiety under the conditions that modifying the 5mC in the nucleic acid molecule by converting 5mC to 5hmC and transferring the modification moiety to 5hmC; and (c) mapping the 5mC in the nucleic acid molecule. In certain aspects, the modification agent is a β-glucosyltransferase and the modification moiety is a glucose or a modified glucose molecule.

As discussed above, the 5mC in the nucleic acid may be mapped by a number of ways, including being mapped by sequencing the modified nucleic acid and comparing the results to a control nucleic acid or by subjecting the modified nucleic acid to a primer extension assay and comparing the results to a control nucleic acid. In some embodiments, 5mCs in the nucleic acid are mapped by subjecting the modified nucleic acid to a hybridization assay and comparing the results to a control nucleic acid.

Certain embodiments are directed to a method comprising converting 5-methylcytosine to a 5-hydroxymethylcytosine, modifying 5-hydroxymethylcytosine with a detectable label or a detectable functional group, and detecting 5-hydroxymethylcytosine in a nucleic acid. In certain aspects, the detectable label is fluorescent, radioactive, enzymatic, electrochemical, or colorimetric lable. In certain embodiments, the 5-hydroxymethylcytosine is modified with a glucose or a modified glucose molecule. In particular embodiments, the glucose or modified glucose is coupled to a detectable label. In certain embodiments, the hydroxyl group of 5-hydroxymethylcytosine is converted to an aldehyde group or carboxyl group. In certain aspects, the hydroxyl group is modified using an enzymatic method or a chemical method.

Embodiments also concern kits, which may be in a suitable container, that can be used to achieve the described methods. In certain embodiments, kits are provided for converting 5mC to 5hmC, modifying 5hmC of nucleic acid and/or subject such modified nucleic acid for further analysis, such as mapping 5mC or sequencing the nucleic acid molecule.

In certain aspect, the contents of a kit can include a methylcytosine dioxygenase, or its homologue and a 5-hydroxymethylcytosine modifying agent. In further aspects, the methylcytosine dioxygenase is TET1, TET2, or TET3. In other embodiments the kit includes the catalytic domain of TET1, TET2, or TET3. In certain aspects, the 5hmC modifying agent, which refers to an agent that is capable of modifying 5hmC, is β-glucosyltransferase.

In additional embodiments, a kit also contains a 5hmC modification, such as uridine diphophoglucose or a modified uridine diphophoglucose molecule. In particular embodiments, the modified uridine diphosphoglucose molecule can be uridine diphospho6-$N_3$-glucose molecule. In additional embodiments, a kit may also contain biotin.

Certain embodiments are directed to kits comprising a vector comprising a promoter operably linked to a nucleic acid segment encoding a methylcytosine dioxygenase or a portion and a 5-hydroxymethylcytosine modifying agent. In certain aspects, the nucleic segment encodes TET1, TET2, or TET3, or their catalytic domain. In certain aspects, the 5hmC modifying agent is β-glucosyltransferase. In additional aspects, a kit also contains a 5hmC modification, such as uridine diphophoglucose or a modified uridine diphophoglucose molecule. In particular embodiments, the modified uridine diphosphoglucose molecule can be uridine diphospho6-$N_3$-glucose molecule. In additional embodiments, a kit may also contain biotin.

In some embodiments, there are kits comprising one or more modification agents (enzymatic or chemical) and one or more modification moieties. The molecules may have or involve different types of modifications. In further embodiments, a kit may include one or more buffers, such as buffers for nucleic acids or for reactions involving nucleic acids. Other enzymes may be included in kits in addition to or instead of β-glucosyltransferase. In some embodiments, an enzyme is a polymerase. Kits may also include nucleotides for use with the polymerase. In some cases, a restriction enzyme is included in addition to or instead of a polymerase.

Certain embodiments are directed to identification of 5hmC by oxidizing 5mC to 5-carboxylcytosine (5caC). The approach includes one, two, three, four or five of the following steps: (1) Labeling 5hmC in a nucleic acid with a glucose, a modified glucose or other modifying agents as described herein, or blocking 5hmC from further modification, or protecting 5hmC from being oxidized to 5caC; (2) Oxidizing 5mC to 5caC. In one example, oxidation of 5mC to 5caC can be accomplished by contacting the modified nucleic acid of step 1 with a methylcytosine dioxygenase (e.g., TET1, TET2 and TET3) or the catalytic domains of a methylcytosine dioxygenase or an enzyme having similar activity; (3) Treating the nucleic acid from step (2) with bisulfite under conditions that will allow sequencing of the nucleic acid; (4) amplifying the bisulfide-treated nucleic acid and/or, (5) Sequencing the amplified nucleic acid in step (4).

Certain embodiments are directed to methods for identifying 5hmC in a nucleic acid molecule comprising incubating a nucleic acid comprising both 5caC and 5hmC with bisulfite and sequencing the nucleic acid after the incubation with bisulfite.

The methods can further comprise converting 5mC to 5caC prior to incubating the nucleic acid with bisulfite. In certain aspects, the 5mC is converted to 5caC using enzymatic modification by methylcytosine dioxygenase. In a further aspect methylcytosine dioxygenase is TET1, TET2, or TET3. In a further aspect, the 5mC is converted to 5caC by using the C-terminal catalytic domain of a methylcytosine dioxygenase. In a further aspect, 5mC is converted to 5caC by homologues of TET1, TET2, TET3, or enzymes having similar activity to methylcytosine dioxygenase. In certain aspects, the 5mC can be converted to 5caC by using other enzymatic or chemical oxidation methods.

The methods can further comprise modifying 5hmC in the nucleic acid composition prior to converting 5mC to 5caC. In certain aspects, 5hmC is modified to protect it from being oxidized to 5caC. In certain aspects, 5hmC is modified with a glucose or an modified glucose other modification resistant to further oxidation. In a further aspect, 5hmC is modified by incubating the nucleic acid molecule with β-glucosyltransferase and a glucose or a modified glucose molecule. In some embodiments, glucose molecule is a uridine diphosphoglucose molecule. The modified glucose molecule is a modified uridine diphosphoglucose molecule.

In certain aspects the nucleic acid molecule is DNA, genomic DNA, or RNA. In particular embodiments, the nucleic acid molecule is isolated from a cell prior to modification of 5hmC.

The methods can further comprise amplifying the bisufite treated nucleic acid molecules prior to sequencing. In certain aspects, the bisulfide treated nucleic acid molecules are amplified by PCR.

Certain embodiments are directed to methods for distinguishing 5hmC from 5mC in a nucleic acid molecule comprising treating the nucleic acid under conditions to convert 5mC to 5caC and sequencing the nucleic acid after the treatment using bisulfite. In certain aspects, the 5mC is converted to 5caC using enzymatic modification by methylcytosine dioxygenase. In a further aspect, methylcytosine dioxygenase is TET1, TET2, or TET3. In a further aspect, the 5mC is converted to 5caC by using the C-terminal catalytic domain of a methylcytosine dioxygenase. In a further aspect, 5mC is converted to 5caC by homologues of TET1, TET2, TET3, or enzymes having similar activity to methylcytosine dioxygenase. In certain aspects, the 5mC can be converted to 5caC by using other enzymatic or chemical oxidation methods.

The methods can further comprise treating the nucleic acid molecule under conditions that modify 5hmC prior to converting 5mC to 5caC. In certain aspects, 5hmC is modified to protect it from being oxidized to 5caC. In certain aspects, 5hmC is modified with a glucose or a modified glucose or other modifications resistant to further oxidation. In a further aspect, 5hmC is modified by incubating the nucleic acid molecule with β-glucosyltransferase and a glucose or a modified glucose molecule. In some embodiments, glucose molecule is a uridine diphosphoglucose molecule. The modified glucose molecule is a modified uridine diphosphoglucose molecule.

In certain aspects the nucleic acid molecule is DNA, genomic DNA, or RNA. In particular embodiments, the nucleic acid molecule is isolated from a cell prior to modification of 5hmC. In other aspects the nucleic acid is contained within a cell, and the nucleic acid is treated with a particular agent by incubating the cell with the agent.

The methods can further comprise amplifying the bisufite treated nucleic acid molecules prior to sequencing. In certain aspects, the bisulfide treated nucleic acid molecules are amplified by PCR.

Certain embodiments are directed to methods for sequencing a nucleic molecule comprising one, two, three, four or five of the following steps: (1) Incubating the nucleic acid molecule with β-glucosyltransferase and a glucose or modified glucose molecue under conditions to modify 5hmC with the gluclose or modified glucose; (2) Incubating the nucleic acid molecule from step (1) with a methylcytosine dioxygenase under conditions to convert 5mC to 5caC; (3) Treating the nucleic acid from step (2) with bisulite under conditions that will allow the sequencing of the nucleic acid; (4) Amplifying the bisulfite-treated nucleic acid; and/or (5) Sequencing the amplified nucleic acid from step (4).

In certain embodiments, kits are provided for converting 5mC to 5caC, modifying 5hmC of nucleic acid and/or subjecting such modified nucleic acid for further analysis, such as amplifying the nucleic acid, or sequencing the nucleic acid.

In certain aspects, the contents of a kit can include a methylcytosine dioxygenase or its homologue. In further aspects, the methylcytosine diosygenase is TET1, TET2, or TET3 or a combination thereof. In other embodiments the kit includes a homolog of TET1, TET2, or TET3.

In certain aspects, the kit further comprises a 5hmC modifying agent, which refers to an agent that is capable of modifying 5hmC. In some embodiments, the 5hmC agent is β-glucosyltransferase. In additional embodiments, a kit also contains a 5hmC modification, such as uridine diphophoglucose molecule or a modified uridine diphophoglucose molecule.

In some aspects, the kit further comprises bisulfite, such as bisulfite that can be used for bisulfite treatment to enable sequencing of nucleic acids. In further aspects, the kit also comprises a polymerase. The contents of kits may also comprise a composition comprising nucleotides for use with the polymerase.

Certain embodiments are directed to kits comprising a vector comprising a promoter operably linked to a nucleic acid segment encoding a mehylcytosine dioxygenase or a portion. In certain aspects, the nucleic acid segment encodes TET1, TET2, or TET3. In certain aspects, the kit further comprises a 5hmC modifying agent. The 5hmC modifying agent is β-glucosyltransferase and the kit may also include a uridine diphosphoglucose molecule or a modified uridine diphosphoglucose molecule. In some aspects, the kit further comprises bisulfite. In further aspects, the kit also comprises a polymerase. The contents of kits may also comprise a composition comprising nucleotides for use with the polymerase.

Methods may involve any of the following steps described herein. In some embodiments, methods involve incubating the nucleic acid molecule with an agent that modifies 5hmC in a target nucleic acid molecule. In other embodiments, methods may involve mixing the nucleic acids with a modifying agent and/or a label or a detectable moiety under conditions to promote modification of the 5hmC in a target nucleic acid. It is contemplated that any modification that prevents 5hmC from being oxidized to 5caC may be implemented in the methods disclosed herein. It is specifically contemplated that reactions involving any enzymes may be restricted or limited by time, enzyme concentration, substrate concentration, and/or template concentration. For example, there may be a partial modification of nucleic acid molecules. Reaction conditions may be adjusted so that the reaction is carried out under conditions that result in about, at least about, or at most about 20, 30, 40, 50, 60, 70, 80, 90, 95, 96, 97, 98, 99, 100% of 5hmC being modified, or any range derivable therein.

Methods may also involve the following steps: modifying 5hmC using β-glucosyltransferase (βGT); incubating β-glucosyltransferase with UDP-glucose molecules and a nucleic acid substrate under conditions to promote glycosylation of the nucleic acid with the glucose molecule (which may or may not be modified) and result in a nucleic acid that is glycosylated at one or more 5hmCs In some embodiments, methods may also involve one or more of the following regarding nucleic acids prior to and/or concurrent with 5hmC modification of nucleic acids: obtaining nucleic acid molecules; obtaining nucleic acid molecules from a biological sample; obtaining a biological sample containing nucleic acids from a subject; isolating nucleic acid molecules; purifying nucleic acid molecules; obtaining an array or microarray containing nucleic acids to be modified; denaturing nucleic acid molecules; shearing or cutting nucleic acid; denaturing nucleic acid molecules; hybridizing nucleic acid molecules; incubating the nucleic acid molecule with an enzyme that does not modify 5hmC; incubating the nucleic acid molecule with a restriction enzyme; attaching one or more chemical groups or compounds to the nucleic acid or 5hmC or modified 5hmC; conjugating one or more chemical groups or compounds to the nucleic acid or 5hmC or modified 5hmC; incubating nucleic acid molecules with an enzyme that modifies the nucleic acid molecules or modified 5hmC by adding or removing one or more elements, chemical groups, or compounds.

Methods may further involve one or more of the following steps that is concurrent with and/or subsequent to modification of nucleic acids: isolating nucleic acids with modified 5hmC; isolating modified nucleic acids based on the modification to 5hmC; purifying modified 5hmC nucleic acids based on the modification, label, or moiety coupled to 5hmC (coupling can be either covalent or non-covalent coupling); reacting the modified 5hmC in the modified nucleic acid molecule with a detectable or functional moiety, such as a linker; conjugating or attaching a detectable or functional moiety to the modified 5hmC nucleotide; exposing to, incubating with, or mixing with the modified nucleic acid an enzyme that will use the modified nucleic acid as a substrate independent of the modification to 5hmC; exposing to, incubating with, or mixing with the modified nucleic acid an enzyme that will use the modified nucleic acid as a substrate unless the modification to the 5hmC modifies, alters, prevents, or hinders it; exposing to, incubating with, or mixing with the modified nucleic acid an enzyme that will use the modified nucleic acid as a substrate unless the modification sterically prevents or inhibits the enzyme; enriching for nucleic acids containing modified nucleic acids; identifying 5hmC in the nucleic acids using the modified 5hmC molecule, identifying 5hmC in the nucleic acid by comparing glycosylated nucleic acids with unmodified nucleic acids; mapping the 5hmC in the nucleic acid molecule; subjecting the modified nucleic acid to chromatography; subjecting the modified nucleic acid to a primer extension assay and comparing the results to a control nucleic acid; subjecting the modified nucleic acid to a hybridization assay and comparing the results to a control nucleic acid; and/or sequencing the glycosylated nucleic acid and comparing the results to a control nucleic acid.

In some embodiments, methods involve converting/oxidizing 5mC to 5caC in a target nucleic acid. The modification of 5hmC in the target nucleic acid described herein may be performed prior to the conversion of 5mC to 5caC. Methods may further involve one or more of the following steps that are subsequent to the conversion of 5mC to 5caC: treating the nucleic acid with bisulfite; amplifying the bisulfite treated nucleic acid; and sequencing the bisulfite treated nucleic acid.

In some embodiments, methods may also involve one or more of the following steps regarding nucleic acids prior to and/or concurrent with the oxidization of 5mC to 5caC of nucleic acids: obtaining nucleic acid molecules; obtaining nucleic acid molecules from a biological sample; obtaining a biological sample containing nucleic acids from a subject; isolating nucleic acid molecules; purifying nucleic acid molecules; obtaining an array or microarray containing nucleic acids to be oxidized; denaturing nucleic acid molecules; shearing or cutting nucleic acid; denaturing nucleic acid molecules; hybridizing nucleic acid molecules; incubating the nucleic acid molecule with an enzyme that does not converting 5mC to 5caC; incubating the nucleic acid molecule with a restriction enzyme; attaching one or more chemical groups or compounds to the nucleic acid or modified 5hmC; conjugating one or more chemical groups or compounds to the nucleic acid or modified 5hmC; incubating nucleic acid molecules with an enzyme that modifies the nucleic acid molecules or modified 5hmC by adding or removing one or more elements, chemical groups, or compounds.

It is contemplated that some embodiments will involve steps that are done in vitro, such as by a person or a person controlling or using machinery to perform one or more steps.

Methods and compositions may involve a purified nucleic acid, modification reagent or enzyme, label, chemical modification moiety, UDP-Glc, modified UDP-Glc, and/or enzyme, such as β-glucosyltransferase. Such protocols are known to those of skill in the art.

In certain embodiments, purification may result in a molecule that is about or at least about 70, 75, 80, 85, 90, 95, 96, 97, 98, 99, 99.1, 99.2, 99.3, 99.4, 99.5, 99.6, 99.7 99.8, 99.9% or more pure, or any range derivable therein, relative to any contaminating components (w/w or w/v).

In other methods, there may be steps including, but not limited to, obtaining information (qualitative and/or quantitative) about one or more 5mCs and/or 5hmCs in a nucleic acid sample; ordering an assay to determine, identify, and/or map 5mCs and/or 5hmCs in a nucleic acid sample; reporting information (qualitative and/or quantitative) about one or more 5mCs and/or 5hmCs in a nucleic acid sample; comparing that information to information about 5mCs and/or 5hmCs in a control or comparative sample. Unless otherwise stated, the terms "determine," "analyze," "assay," and "evaluate" in the context of a sample refer to transformation of that sample to gather qualitative and/or quantitative data about the sample. Moreover, the term "map" means to identify the location within a nucleic acid sequence of the particular nucleotide.

In some embodiments, nucleic acid molecules may be DNA, RNA, or a combination of both. Nucleic acids may be recombinant, genomic, or synthesized. In additional embodiments, methods involve nucleic acid molecules that are isolated and/or purified. The nucleic acid may be isolated from a cell or biological sample in some embodiments. Certain embodiments involve isolating nucleic acids from a eukaryotic, mammalian, or human cell. In some cases, they are isolated from non-nucleic acids. In some embodiments, the nucleic acid molecule is eukaryotic; in some cases, the nucleic acid is mammalian, which may be human. This means the nucleic acid molecule is isolated from a human cell and/or has a sequence that identifies it as human. In particular embodiments, it is contemplated that the nucleic acid molecule is not a prokaryotic nucleic acid, such as a bacterial nucleic acid molecule. In additional embodiments, isolated nucleic acid molecules are on an array. In particular cases, the array is a microarray. In some cases, a nucleic acid is isolated by any technique known to those of skill in the art, including, but not limited to, using a gel, column, matrix or filter to isolate the nucleic acids. In some embodiments, the gel is a polyacrylamide or agarose gel.

Methods and compositions may also include a modified 5hmC. In some embodiments, the modified 5hmC comprises a modification moiety. In some embodiments, more than one modification moiety is included. The term "modification moiety" refers to a chemical compound or element that is added to a 5hmC. A modified 5hmC refers to a 5hmC molecule having (i) a modification moiety or (ii) a chemical compound or element that is substituted for or covalently coupled to a 5hmC, such that the resulting modified 5hmC has a different chemical formula than unmodified 5hmC. In some embodiments, the modified 5hmC protects the 5hmC from oxidation. In certain embodiments, the modified 5hmC prevents the 5hmC from being a substrate of methylcytosine dioxygenase, such as TET1, 2, or 3. It is specifically contemplated that a modified 5hmC does not include a 5hmC that is radioactive by substitution of a molecule or compound in a 5hmC with the same molecule or compound, for example, a molecule or compound that is merely radioactive. In certain embodiments a 5mC molecule is specifically excluded or included as a modified 5hmC.

In certain embodiments, modified 5hmC or a modification moiety may comprise one or more detectable moieties. A detectable moiety refers to a chemical compound or element that is capable of being detected. In particular embodiments, a modified 5hmC is not a version of 5hmC that is radioactive, and in specific embodiments, a modified 5hmC does not have a radioactive carbon molecule. In certain embodiments, a detectable moiety is fluorescent, radioactive, enzymatic, electrochemical, or colorimetric. In some embodiments, the detectable moiety is a fluorophore or quantum dot. It is specifically contemplated that in some embodiments the 5hmC does not comprise a modification moiety that is fluorescent, radioactive, or colorimetric.

In some embodiments, a modification moiety may be a linker that allows one or more functional or detectable moieties or isolation tags to be attached to the modified 5hmC containing molecules. In some embodiments the linker is an azide linker or a thiol linker. In further embodiments, the modification moiety may be an isolation tag, which means the tag can be used to isolate a molecule that is attached to the tag. In certain embodiments, the isolation tag is biotin or a histidine tag. In some cases, the tag is modified, such as with a detectable moiety. It is contemplated that the linker allows for other chemical compounds or substances to be attached to the modified nucleic acid at 5hmC. In other embodiments, a functional moiety is attached to the target molecule after 5hmC has be modified. In certain embodiments one or more functional and/or detectable moieties and/or isolation tags are attached to each 5hmC nucleotides.

In further embodiments, a functional moiety comprises a molecule or compound that inhibits or blocks an enzyme from using the 5hmC in the nucleic acid molecule as a substrate. In some embodiments, the inhibition is sufficiently complete to prevent detection of an enzymatic reaction involving the 5hmC such as oxidation by a methylcytosine dioxygenase. It is contemplated that the molecule or compound that blocks an enzyme may be doing this by sterically blocking access of the enzyme. Such sterical blocking moieties are specifically contemplated as modification moieties. In specific embodiments, the sterical blocking moieties contain 1, 2, or 3 ringed structures, including but not limited to aromatic ring structures. In certain embodiments the blocking moiety is polyethylene glycol. In other embodiments, it is a nucleic acid, amino acid, carbohydrate, or fatty acid (including mono-, di-, or tri-versions).

Methods and compositions may also involve one or more enzymes. In some embodiments, the enzyme is a restriction enzyme or a polymerase. In certain cases, embodiments involve a restriction enzyme. The restriction enzyme may be methylation-insensitive. In other embodiments, the enzyme is polymerase. In certain embodiments, nucleic acids are contacted with a restriction enzyme prior to, concurrent with, or subsequent to modification of 5mC. The modified nucleic acid may be contacted with a polymerase before or after the nucleic acid has been exposed to a restriction enzyme.

Methods and compositions involve detecting, characterizing, and/or distinguishing between methylcytosine and 5hmC after protecting the 5hmC from oxidation. Methods may involve identifying 5hmC in the nucleic acids by comparing modified nucleic acids with unmodified nucleic acids or to nucleic acids whose modification state is already known. Detection of the modification can involve a wide variety of recombinant nucleic acid techniques. In some embodiments, a modified nucleic acid molecule is incubated with polymerase, at least one primer, and one or more nucleotides under conditions to allow polymerization of the modified nucleic acid. In additional embodiments, methods may involve sequencing a modified nucleic acid molecule. In other embodiments, a modified nucleic acid is used in a primer extension assay.

In certain embodiments, methods also involve distinguishing cytosine from methylcytosine. In some embodiments, methods include performing traditional bisulfate sequencing, without protecting 5hmC so as to distinguish cytosine from methylcytosine. The results from traditional bisulfate sequencing (performed without the hmC labeling or protection prior to exposure to a methyldioxygenase) may be compared to the results of methods discussed herein that distinguish 5hmC from 5mC.

Methods and compositions may involve a control nucleic acid. The control may be used to evaluate whether modification or other enzymatic or chemical reactions are occurring. Alternatively, the control may be used to compare modification states. The control may be a negative control or it may be a positive control. It may be a control that was not incubated with one or more reagents in the modification reaction. Alternatively, a control nucleic acid may be a reference nucleic acid, which means its modification state (based on qualitative and/or quantitative information related to modification at 5hmCs, or the absence thereof) is used for comparing to a nucleic acid being evaluated. In some embodiments, multiple nucleic acids from different sources provide the basis for a control nucleic acid. Moreover, in some cases, the control nucleic acid is from a normal sample with respect to a particular attribute, such as a disease or condition, or other phenotype. In some embodiments, the control sample is from a different patient population, a different cell type or organ type, a different disease state, a different phase or severity of a disease state, a different prognosis, a different developmental stage, etc.

Particular embodiments involve identifying 5hmC in genomic DNA comprising: (a) isolating the genomic DNA; (b) shearing or cutting the genomic DNA into pieces; (c) mixing the genomic DNA pieces with modification agent and a modification moiety under conditions to promote modification of the 5hmC in the genomic DNA; and, (d) identifying 5hmC in the genomic DNA using the introduced modification.

Embodiments may involve methods for mapping 5hmC in a nucleic acid molecule comprising incubating the nucleic acid molecule with modification agent and a modification moiety to modify 5hmC in the nucleic acid molecule with the modification moiety; and mapping the 5hmC in the nucleic acid molecule. As discussed above, the 5hmC in the nucleic acid may be mapped by a number of ways, including being mapped by sequencing the modified nucleic acid and comparing the results to a control nucleic acid or by subjecting the modified nucleic acid to a primer extension assay and comparing the results to a control nucleic acid. In some embodiments, 5hmCs in the nucleic acid are mapped by subjecting the modified nucleic acid to a hybridization assay and comparing the results to a control nucleic acid.

Embodiments also concern kits, which may be in a suitable container, that can be used to achieve the described methods. In some embodiments, there are kits comprising one or more modification agents (enzymatic or chemical) and one or more modification moieties. The molecules may have or involve different types of modifications. In further embodiments, a kit may include one or more buffers, such as buffers for nucleic acids or for reactions involving nucleic acids. Other enzymes may be included in kits in addition to or instead of β-glucosyltransferase. In some embodiments, an enzyme is a polymerase. Kits may also include nucleotides for use with the polymerase. In some cases, a restriction enzyme is included in addition to or instead of a polymerase.

Other embodiments also concern an array or microarray containing nucleic acid molecules that have been modified at the nucleotides that were 5hmC and/or 5mC.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 7A-7B 5-methylcytosine (5mC) oxidation and selective labeling in genomic DNA. (a) 5-methylcytosine in duplex DNA can be oxidized to 5hmC by methylcytosine dioxygenases such as TET1, TET2 and TET3. The newly added hydroxyl group is then glucosylated by β-GT to form β-6-azide-glucosyl-5-hydroxymethylcytosine ($N_3$-ghmC) by using UDP-6-N3-Glu as a co-factor. (b) The azide group can be labeled with a biotin moiety using click chemistry for subsequent detection, affinity purification and sequencing.

FIG. 10A shows genome-wide correlation between TAmC-Seq and 5hmC-Seq (10 kb bins, reads per million). FIG. 10B shows genome-wide correlation between TAmC-Seq and MeDIP-Seq (10 kb bins, reads per million). FIG. 10C shows average 5mC read densities derived from TAmC-Seq and MeDIP-Seq within regions enriched for 5hmC. 5hmC enriched regions were divided in 10 equal portions as well as 10 portions of the same size upstream, within, and downstream of the 5hmC enriched region. Shown are the average 5mC read densities for all 5hmC enriched regions.

FIG. 11B demonstrates the newly developed oxidation-coupled bisulfite sequencing, which can selectively provide single-base resolution sequencing of 5hmC (5caU is 5-carboxyluracile).

Figures 1A, 1B:
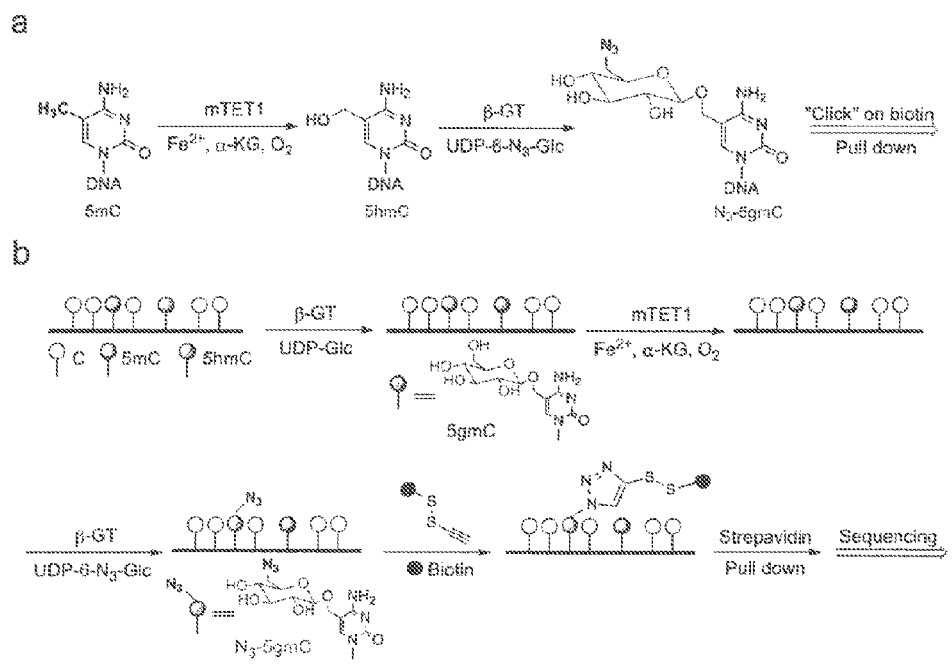
FIGS. 1A-1B. Schematic diagram of the selective labeling of 5mC in DNA. (a) 5mC can be converted to 5hmC via mTET1-mediated oxidation, and then labeled with a modified glucose moiety (6-$N_3$-Glucose) by β-GT-mediated glucosylation to generate 6-$N_3$-β-glucosyl-5-hydroxymethyl-cytosine ($N_3$-5gmC), which could be further labeled using click chemistry. (b) The endogenous 5hmC in genomic DNA can be protected by glycosylation with regular glucose. Using an one-pot mTET1/β-GT protocol, 5mC is converted into $N_3$-5gmC in the presence of both mTET1 and β-GT. The biotin moiety can then be installed for subsequent detection, affinity purification, and sequencing.

FIGS. 27A-27F 5hmCG is Biased towards Low CpG Regions. Shown are heatmaps of percent 5hmCG (±250 bp from TSS or DHS) as a function of CpG density for (A) Promoters in H1 ES cells, (B) promoters in mouse ES cells, (D) DHS sites lacking H3K4me1 and H3K27ac, E) DHS sites with a poised enhancer chromatin signature, and (F) DHS sites with an active enhancer chromatin signature. (C) The GC content relative to the CpG content for the 5hmC-enriched versus the 5hmC not enriched promoters.

FIGS. 28A-28H (A) Heatmap of total methylation±250 bp from TSSs, as a function of CpG density. (B) Heatmap of percent 5hmCG±250 bp from distal p300 binding sites, as a function of CpG density. (C) Heatmap as in (B), but for the subset of binding sites with DNase I hypersensitivity. (D) Heatmap of total methylation ±250 bp from DNase I hypersensitive sites lacking H3K4me1 and H3K27ac, as a function of CpG density. (E) Heatmap of total methylation ±250 bp from DNase I hypersensitive sites having H3K4me1 but not H3K27ac, as a function of CpG density. (F) Heatmap of total methylation ±250 bp from DNase I hypersensitive sites having both H3K4me1 and H3K27ac, as a function of CpG density. (G) The distribution of CpG content for 5hmC-enriched (red) and 5hmC-unenriched (green) bivalent promoters (left) and H3K4me3-only promoters (right). (H) The density of 5hmC at promoters classified as having low (LCP), intermediate (ICP), and high (HCP) CpG content, normalized by the number of CpG dinucleotides in these promoters.

DETAILED DESCRIPTION OF THE INVENTION

Certain embodiments are directed to methods and compositions for modifying 5mC, detecting 5mC, and/or evaluating 5mC in nucleic acids. In certain aspects, 5mC is modified (the chemical structure of 5mC is changed to include new functional group or chemical moiety) enzymatically and/or chemically. In a further aspect 5mC is coupled to a modification moiety, which includes detectable groups. Using the methods described herein a large variety of detectable groups (biotin, fluorescent tag, radioactive groups, etc.) can be coupled to 5mC via modification.

Additional embodiments are directed to methods and compositions for modifying 5hmC, detecting 5hmC, and/or evaluating 5hmC in nucleic acids. In certain aspects, 5hmC is modified (the chemical structure of 5mC is changed to include new functional group or chemical moiety) enzymatically and/or chemically to protect 5hmC from being oxidized. Some embodiments are directed to an oxidation-coupled bisulfite sequencing of a nucleic acid to identify 5hmC therein, comprising one or more of the steps of modifying 5hmC and converting 5mC to 5caC. Using the methods described herein, the specific sites of 5hmC in a nucleic acid molecule or in a genome are determined at single-base resolution for research, clinical or other applications in an economic and efficient way.

I. Conversion of 5mC to 5caC

DNA epigenetic modifications such as 5-methylcytosine (5mC) play key roles in biological functions and various diseases. Currently, most common technique for studying cytosine methylation is the bisulfite treatment-based sequencing. This technique has major drawbacks in not being able to differentiate 5mC and 5hmC (5-hydroxymethylcytosine), and harsh conditions are required. Readily available and robust technologies for clinical diagnostic of 5hmC are very limited. The inventors present a method for identifying 5hmC or distinguishing 5hmC from 5mC in a nucleic acid and specific site detection of 5hmC for clinical or other applications in an economic and highly efficient way. The approach includes one or more of the following steps:

1. Labeling endogenous or pre-existing 5hmC in a nucleic acid with a glucose, or a modified glucose as described herein, or blocking 5hmC from further modification or oxidization, then performing step 2.

2. Oxidizing 5mC to 5caC. Oxidation of 5mC to 5caC can be accomplished by contacting the modified nucleic acid of step 1 with a methylcytosine dioxygenases (e.g., TET1, TET2 and TET3) or an enzyme having similar activity or the catalytic domain of a methylcytosine dioxygenase; or chemical modification.

3. Treating the nucleic acid from step 2 with bisulfite under conditions that will allow sequencing of the nucleic acid.

4. Amplifying the bisulfite-treated nucleic acid.

5. Sequencing the amplified nucleic acid.

In some embodiments, it is contemplated that TET1, TET2, or TET3 are human or mouse proteins. Human TET1 has accession number NM_030625.2; human TET2 has accession number NM_001127208.2, alternatively, NM_017628.4; and human TET3 has accession number NM_144993.1. Mouse TET1 has accessioni number NM_027384.1; mouse TET2 has aceesion number NM_001040400.2; and mouse TET3 has accession number NM_183138.2.

5-methylcytosine (5mC) in DNA has an important function in gene expression, genomic imprinting, and suppression of transposable elements. It is known that 5mC can be converted to 5-hydroxymethylcytosine (5hmC) by the Tet (ten eleven translocation) proteins. Recently, it has been discovered that in addition to 5hmC, the Tet proteins can convert 5mC to 5-formylcytosine (5fC) and 5-carboxylcytosine (5caC) in an enzymatic activity-dependent manner (Ito et al., 2011, incorporated by reference).

To determine whether the Tet proteins oxidize 5mC not only to 5hmC, but also to 5fC and 5caC, Taq I capable of digesting DNA modified with 5mC, 5hmC (Huang et al., 1982), 5fC or 5caC was identified. Using TaqI digestion and 2D-TLC using two different buffer conditions, the enzymatic activities of the Tet proteins were analyzed. Compared with the catalytic-deficient mutant control, incubation of the Tet1 protein with 5mC containing substrate resulted in a decrease in the 5mC level and an appearance of a radioactive spot that correlates with 5hmC. Two additional radioactive spots, labeled "X" and "Y" were observed and their appearance depends on Tet1 enzymatic activity. Similarly, Tet2 and Tet3 also generated three enzymatic activity-dependent radioactive spots that were detected in Tet1-catalyzed reaction. However, the signal that corresponds to the "Y" spot from the Tet3 reaction is extremely weak (Ito et al., 2011).

Then, it was demonstrated that the "X" and "Y" spots are 5fC and 5caC. The migration patterns of 5fC and 5caC were compared with that of Tet2-treated 5mC-containing DNA substrates. It was found that the "X" and "Y" spots match 5fC and 5caC in terms of their migration. This was further verified by mixing radioactive 5fC or 5caC with the samples before performing 2D-TLC. To confirm the identities of the "X" and "Y" spots, the Tet2-catalyzed reaction mixture was treated with sodium borohydride (NaBH4), which resulted in the disappearance of both "X" and "Y" spots together with an increase in 5hmC. These results shows that both spots represent oxidation products of 5hmC, consistent with the conclusion that they are 5fC and 5caC (Ito et al., 2011.).

It is known that O-ethylhydroxylamine hydrochloride (EHL) and 1-ethyl-3-(3-dimethylaminopropyl) carbodiimide hydrochloride (EDC) react with formyl and carboxyl groups to generate oximes and amides, respectively (Kukushkin et al., 1999, and Williams et al., 1981). To determine the migration patterns of the reaction products, reactions using standard 5fC and 5caC were performed. The products were then separated by 2D-TLC. The migration patterns for oxime and amide were established. Similar EHL treatment of the Tet2 reaction mixture specifically converted the "X" spot to a new spot that co-migrated with oxime. Meanwhile, EDC treatment specifically converted the "Y" spot to a new signal that co-migrated with amide (Ito et al., 2011)

The identities of "X" and Y" were also defined by mass spectrometry. The mass spectrometry fingerprints of standard 5fC and 5caC were first established. Then, we extracted the "X" and "Y" spots were extracted and subjected to mass spectrometric analysis. The "X" spot shows the same major fragment ions as that of 5fC, while the "Y" spot shows the same major fragment ions as that of 5caC.

Collectively, 2D-TLC co-migration, chemical treatment, and mass spectrometry fingerprints demonstrate that Tet proteins not only can convert 5mC to 5hmC, but also can further oxidize 5hmC to 5fC and 5caC (Ito et al., 2011).

To determine if Tet proteins can use 5hmC or 5fC containing DNA as substrates, 20mer DNA oligos with either 5hmC or 5fC in the TaqI site were incubated with Tet proteins. 2D-TLC analysis demonstrated that incubation with wild-type Tet proteins, but not the catalytic mutants, resulted in a decrease in the level of 5hmC/5fC concomitant with the appearance of 5fC and 5caC, or 5caC, suggesting that Tet proteins can act upon 5hmC and 5fC containing substrates. However, the 5caC signal generated by Tet3 is extremely weak (Ito et al., 2011)

A quantitative mass spectrometric assay was used to rule out the possibility that 5fC and 5caC are generated as a side reaction by Tet proteins. A standard curve for each of the cytosine derivatives was first generated by mixing different amounts of each 5mC, 5hmC, 5fC, and 5caC followed by LC-MS. Then, the cytosine derivatives were quantified at different time points after incubating Tet2 with 5mC, 5hmC, or 5fC containing DNA substrates. Quantification of the relative amount of the substrate and the various products during the reaction process demonstrated that the reaction plateaued after 10 min of incubation regardless whether 5mC, 5hmC, or 5fC-containing TaqI 20mer DNA is used as a substrate. The reaction plateaued in 10 min due to the inactivation of the Tet2 enzyme during the incubation. During this period, Tet2 is able to convert more than 95% of the 5mC to 5hmC (~60%), 5fC (~30%), and 5caC (5%), but it can only convert about 40% or 25% when 5hmC or 5fC-containing DNA was used as a substrate. Based on this data, the initial reaction rate of Tet2 for 5mC, 5hmC, and 5fC-containing substrates was calculated to be 429 nM/min, 87.4 nM/min, and 56.6 nM/min, respectively. Although Tet2 has a clear preference for the 5mC-containing DNA substrate, its initial reaction rate for 5hmC and 5fC containing substrate is only 4.9-7.6 fold lower. The fact that there is clear accumulation of 5fC and 5caC when 5mC is used as a substrate strongly suggests that Tet-catalyzed iterative oxidation is a kinetically relevant pathway (Ito et al., 2011)

It has also been demonstrated that Tet-catalyzed iterative oxidation of 5mC can take place in vivo. A mammalian expression construct containing the Tet2 catalytic domain fused to GFP was transfected into HEK293 cells. After FACS sorting, genomic DNA of GFP positive cells was analyzed for the presence of 5hmC, 5fC, and 5caC by 2D-TLC. Compared with the untransfected control, cells expressing Tet2 not only have increased 5hmC levels, but also contain two additional spots, which correspond to 5fC and 5caC, respectively. In addition, we the genomic content of 5hmC, 5fC, and 5caC was quantified (Boysen et al., 2010). After establishing the retention times for each of the cytosine derivatives on HPLC, nucleosides derived from genomic DNA were subjected to the same HPLC conditions for fractionation. Fractions A and B that have the same retention times as that of 5caC and 5hmC or 5fC were collected. Mass spectrometry analysis demonstrates that both 5fC and 5caC are detected in the genomic DNA of cells overexpressing Tet2. By comparison to the standard curves, overexpression of wild-type Tet2, but not a catalytic mutant, increased the genomic content of 5hmC, 5fC and 5caC (Ito et al., 2011).

Furthermore, the presence of 5fC and 5caC in genomic DNA of mouse ES cells and mouse organs were revealed. Using a similar approach as that used for the genomic DNA of Tet2-overexpressing HEK293, it has been shown that not only 5hmC, but also 5fC and 5caC are present in the genomic DNA of mouse ES cells. To quantify the genomic content of 5hmC, 5fC and 5caC in mouse ES cells, standard curves for each of the 5mC derivatives were generated at low concentrations and the limit of detection for 5fC and 5caC was determined to be 5 fmol and 10 fmol, respectively. Then, the genomic content of these cytosine derivatives in mouse ES cells was quantified to be about $1.3 \times 10^3$ 5 hmC, 20 5fC, and 3 5caC in every $10^6$ C. Knockdown of Tet1 reduced the genomic content of 5hmC, as well as 5fC and 5caC, indicating that Tet1 is at least partially responsible for the generation of these cytosine derivatives. The presence of 5fC is not limited to ES cells as similar analysis also revealed their presence in genomic DNA of major mouse organs. However, 5caC can be detected with confidence only in ES cells (Ito et al., 2011)

The data described herein demonstrate that the Tet family of proteins have the capacity to convert 5mC not only to 5hmC, but also to 5fC and 5caC in vitro. In addition, it has been shown that 5fC is present in the genomic DNA of mouse ES cells and organs and 5caC is present in moue ES cells (Ito et al., 2011).

II. Nucleotide Modification

A. Modification of 5mC

Modification of 5mC can be performed using the enzymes or chemical agents, that catalyzes or cause the transfer of a modification moiety to the 5mC, yielding a modified 5mC (m5mC). The inventors found this strategy useful for incorporating modifications to 5mC for labeling or tagging 5mC in eukaryotic nucleic acids.

Chemical tagging can be used to determine the precise locations of 5mC in a high throughput manner. The inventors have shown that the 5mC modification renders the labeled DNA resistant to certain restriction enzyme digestion and/or polymerization. In certain aspects, modified and unmodified genomic DNA may be treated with restriction enzymes and subsequently subjected to various sequencing methods to reveal the precise locations of each cytosine modification that hampers the digestion.

The inventors have shown that a modification moiety, such as a functional group like an azide group, can be incorporated into DNA using methods described herein. This incorporation of a functional group allows further labeling or tagging cytosine residues with biotin and other tags. The labeling or tagging of 5mC can use, for example, click chemistry or other functional/coupling groups known to those skilled in the art. The labeled or tagged DNA fragments containing m5mC can be isolated and/or evaluated using modified methods being currently used to evaluate 5mC containing nucleic acids.

Furthermore, methods and compositions of the invention may be used to introduce a sterically bulky group to 5mC. The presence of a bulky group on the DNA template strand will interfere with the synthesis of a nucleic acid strand by DNA polymerase or RNA polymerase, or the efficient cleavage of DNA by a restriction endonuclease or inhibition of other enzymatic modifications of nucleic acid containing 5mC. As a result, primer extensions or other assays can be employed, for example, to evaluate a partially extended primer of certain length and the modification sites can be revealed by sequencing the partially extended primers. Other approaches taking advantage of this chemical tagging method are also contemplated.

B. Oxidation of 5mC for Detection, Sequencing, and Diagnostic Methods

DNA epigenetic modifications such as 5-methylcytosine (5mC) play key roles in biological functions and various diseases. Currently, most common technique for studying cytosine methylation is the bisulfate treatment-based sequencing. This technique has major drawbacks in not being able to differentiate 5mC from 5hmC (5-hydroxymethylcytosine), and harsh conditions are required. Readily available and robust technologies for clinical diagnostic of 5mC are very limited. Based on the method on selective labeling and detection/sequencing of 5hmC (Song et al., 2011), which is incorporated herein by reference), the inventors present a method for determining the genome wide distribution of 5mC and specific site detection of 5mC for clinical or other applications in an economic, reliable, and highly efficient way. The approach includes one or more of the following steps:

1. Oxidizing 5mC to 5hmC. Oxidation of 5mC to 5hmC can be accomplished by contacting the modified nucleic acid of step 1 with a methylcytosine dioxygenases (e.g., TET1, TET2 and TET3) or an enzyme having similar activity; or chemical modification.

2. Labeling endogenous or pre-existing 5hmC in a nucleic acid with a first glucose, a first modified glucose as described herein, or blocking 5hmC from further modification, then performing step 1.

3. Labeling 5hmC generated by step 1 and/or 2 with a second labeled or modified glucose that can be differentiated from that used for labeling of 5hmC present prior to the oxidation step in the same nucleic acid.

4. Enriching for modified 5mC generated in any of the steps above, e.g., by affinity chromatography, for detection, sequencing and diagnostic applications.

The approach described herein also involves performing step 1 and step 3 at the same time, i.e., the oxidization of 5mC to 5hmC and the modification of generated 5hmC occur in one step.

C. Modification of 5hmC

Certain embodiments are directed to methods and compositions for modifying 5hmC, detecting 5hmC, and/or evaluating 5hmC in nucleic acids. In certain aspects, 5hmC is glycosylated. In a further aspect 5hmC is coupled to a labeled or modified glucose moiety. In certain aspects a target nucleic acid is contacted with a β-glucosyltransferase enzyme and a UDP substrate comprising a modified or modifiable glucose moiety. Using the methods described herein a large variety of detectable groups (biotin, fluorescent tag, radioactive groups, etc.) can be coupled to 5hmC via a glucose modification. Methods and compositions are described in PCT application PCT/US2011/031370, filed Apr. 6, 2011, which is hereby incorporated by reference in its entirety.

Modification of 5hmC can be performed using the enzyme β-glucosyltransferase (βGT), or a similar enzyme, that catalyzes the transfer of a glucose moiety from uridine diphosphoglucose (UDP-Glc) to the hydroxyl group of 5hmC, yielding β-glycosyl-5-hydroxymethyl-cytosine (ghmC). The inventors have found that this enzymatic glycosylation offers a strategy for incorporating modified glucose molecules for labeling or tagging 5hmC in eukaryotic nucleic acids. For instance; a glucose molecule chemically modified to contain an azide ($N_3$) group may be covalently attached to 5hmC through this enzyme-catalyzed glycosylation. Thereafter, phosphine-activated reagents, including but not limited to biotin-phosphine, fluorophore-phosphine, and NHS-phosphine, or other affinity tags can be specifically installed onto glycosylated 5hmC via reactions with the azide.

Chemical tagging can be used to determine the precise locations of 5hmC in a high throughput manner. The inventors have shown that the ghmC modification renders the labeled DNA resistant to restriction enzyme digestion and/or polymerization. In certain aspects, glycosylated and unmodified genomic DNA may be treated with restriction enzymes and subsequently subjected to various sequencing methods to reveal the precise locations of each cytosine modification that hampers the digestion.

The inventors have shown that a functional group (e.g., an azide group) can be incorporated into DNA using methods described herein. This incorporation of a functional group allows further labeling or tagging cytosine residues with biotin and other tags. The labeling or tagging of 5hmC can use, for example, click chemistry or other functional/coupling groups know to those skilled in the art. The labeled or tagged DNA fragments containing 5hmC can be isolated and/or evaluated using modified methods being currently used to evaluate 5mC containing nucleic acids.

Furthermore, methods and compositions of the invention may be used to introduce a sterically bulky group to 5hmC. The presence of a bulky group on the DNA template strand will interfere with the synthesis of a nucleic acid strand by DNA polymerase or RNA polymerase, or the efficient cleavage of DNA by a restriction endonuclease or inhibition of other enzymatic modifications of nucleic acid containing 5hmC. As a result, primer extensions or other assays can be employed, for example, to evaluate a partially extended primer of certain length and the modification sites can be revealed by sequencing the partially extended primers. Other approaches taking advantage of this chemical tagging method are also contemplated.

In certain aspects, differential modification of nucleic acid between two or more samples can be evaluated. Studies including heart, liver, lungs, kidney, muscle, testes, spleen, and brain indicate that under normal conditions 5hmC is predominately in normal brain cells. Additional studies have shown that 5hmC is also present in mouse embryonic stem cells. The Ten-eleven translocation 1 (TET1) protein has been identified as the catalyst for converting 5-mC to 5hmC. Studies have shown that TET1 expression is inversely correlated to 5-mC expression. Overexpression of TET1 in cells seems to correlate with increased expression of 5hmC. Also, TET1 is known to be involved in pediatric and adult acute myeloid leukemia and acute lymphoblastic leukemia. Thus, evaluating and comparing 5hmC levels can be used in evaluating various disease states and comparing various nucleic acid samples.

D. TET Proteins

The ten-eleven translocation (TET) proteins are a family of DNA hydroxylases that have been discovered to have enzymatic activity toward the methyl group on the 5-position of cytosine (5-methylcytosine[5mC]). The TET protein family includes three members, TET1, TET2, and TET3. TET proteins are believed to have the capacity of converting 5mC into 5-hydroxymethylcytosine (5hmC), 5-formylcytosine (5fC), and 5-carboxylcytosine (5caC) through three consecutive oxidation reactions.

The first member of TET family proteins, TET1 gene, was first detected in acute myeloid leukemia (AML) as a fusion partner of the histone H3 Lys 4 (H3K4) methyltransferase MLL (mixed-lineage leukemia) (Ono et al., 2002; Lorsbach et al., 2003). It has been first discovered that human TET1 protein possesses enzymatic activity capable of hydroxylating 5mC to generate 5hmC (Tahiliani et al., 2009). Later on, all members of the mouse TET protein family (TET 1-3) have been demonstrated to have 5mC hydroxylase activities (Ito et al., 2010).

TET proteins generally possess several conserved domains, including a CXXC zinc finger domain which has high affinity for clustered unmethylated CpG dinucleotides, a catalytic domain that is typical of Fe(II)- and 2-oxoglutarate (2OG)-dependent dioxygenases, and a cysteine-rich region (Wu and Zhang, 2011, Tahiliani et al., 2009).

E. β-glycosyltransferase (β-GT)

A glucosyl-DNA beta-glucosyltransferase (EC 2.4.1.28, β-glycosyltransferase (βGT)) is an enzyme that catalyzes the chemical reaction in which a beta-D-glucosyl residue is transferred from UDP-glucose to a glucosylhydroxymethylcytosine residue in a nucleic acid. This enzyme resembles DNA beta-glucosyltransferase in that respect. This enzyme belongs to the family of glycosyltransferases, specifically the hexosyltransferases. The systematic name of this enzyme class is UDP-glucose:D-glucosyl-DNA beta-D-glucosyltransferase. Other names in common use include T6-glucosyl-HMC-beta-glucosyl transferase, T6-beta-glucosyl transferase, uridine diphosphoglucose-glucosyldeoxyribonucleate, and beta-glucosyltransferase.

In certain aspects, the a β-glucosyltransferase is a His-tag fusion protein having the amino acid sequence (βGT begins at amino acid 25(met)):

```
                                           (SEQ ID NO: 2)
SHHHHHHSSGVDLGTENLYFQSNAMKIAIINMGNNVINFKTVPSSETIY

LFKVISEMGLNVDIISLKNGVYTKSFDEVDVNDYDRLIVVNSSINFFGG

KPNLAILSAQKFMAKYKSKIYYLFTDIRLPFSQSWPNVKNRPWAYLYTE

EELLIKSPIKVISQGINLDIAKAAHKKVDNVIEFEYFPIEQYKIHMNDF

QLSKPTKKTLDVIYGGSFRSGQRESKMVEFLFDTGLNIEFFGNAREKQF
```

-continued
```
KNPKYPWTKAPVFTGKIPMNMVSEKNSQAIAALIIGDKNYNDNFITLRV

WETMASDAVMLIDEEFDTKHRIINDARFYVNNRAELIDRVNELKHSDVL

RKEMLSIQHDILNKTRAKKAEWQDAFKKAIDL.
```

In other embodiments, the protein may be used without the His-tag (hexa-histidine tag shown above) portion. For example, βGT was cloned into the target vector pMCSG19 by Ligation Independent Cloning (LIC) method according to Donnelly et al. (2006). The resulting plasmid was transformed into BL21 star (DE3) competent cells containing pRK1037 (Science Reagents, Inc.) by heat shock. Positive colonies were selected with 150 µg/ml Ampicillin and 30 µg/ml Kanamycin. One liter of cells was grown at 37° C. from a 1:100 dilution of an overnight culture. The cells were induced with 1 mM of IPTG when OD600 reaches 0.6-0.8. After overnight growth at 16° C. with shaking, the cells were collected by centrifugation, suspended in 30 mL Ni-NTA buffer A (20 mM Tris-HCl pH 7.5, 150 mM NaCl, 30 mM imidazole, and 10 mM (β-ME) with protease inhibitor PMSF. After loading to a Ni-NTA column, proteins were eluted with a 0-100% gradient of Ni-NTA buffer B (20 mM Tris-HCl pH 7.5, 150 mM NaCl, 400 mM imidazole, and 10 mM β-ME). βGT-containing fractions were further purified by MonoS (Buffer A: 10 mM Tris-HCl pH 7.5; Buffer B: 10 mM Tris-HCl pH 7.5, and 1M NaCl) to remove DNA. Finally, the collected protein fractions were loaded onto a Superdex 200 (GE) gel-filtration column equilibrated with 50 mM Tris-HCl pH 7.5, 20 mM $MgCl_2$, and 10 mM β-ME. SDS-PAGE gel revealed a high degree of purity of βGT. βGT was concentrated to 45 µM and stored frozen at −80° C. with an addition of 30% glycerol.

A variety of proteins can be purified using methods known in the art. Protein purification is a series of processes intended to isolate a single type of protein from a complex mixture. Protein purification is vital for the characterization of the function, structure and interactions of the protein of interest. The starting material is usually a biological tissue or a microbial culture. The various steps in the purification process may free the protein from a matrix that confines it, separate the protein and non-protein parts of the mixture, and finally separate the desired protein from all other proteins. Separation of one protein from all others is typically the most laborious aspect of protein purification. Separation steps exploit differences in protein size, physicochemical properties and binding affinity.

Evaluating purification yield. The most general method to monitor the purification process is by running a SDS-PAGE of the different steps. This method only gives a rough measure of the amounts of different proteins in the mixture, and it is not able to distinguish between proteins with similar molecular weight. If the protein has a distinguishing spectroscopic feature or an enzymatic activity, this property can be used to detect and quantify the specific protein, and thus to select the fractions of the separation, that contains the protein. If antibodies against the protein are available then western blotting and ELISA can specifically detect and quantify the amount of desired protein. Some proteins function as receptors and can be detected during purification steps by a ligand binding assay, often using a radioactive ligand.

In order to evaluate the process of multistep purification, the amount of the specific protein has to be compared to the amount of total protein. The latter can be determined by the Bradford total protein assay or by absorbance of light at 280 nm, however some reagents used during the purification process may interfere with the quantification. For example, imidazole (commonly used for purification of polyhistidine-tagged recombinant proteins) is an amino acid analogue and at low concentrations will interfere with the bicinchoninic acid (BCA) assay for total protein quantification. Impurities in low-grade imidazole will also absorb at 280 nm, resulting in an inaccurate reading of protein concentration from UV absorbance.

Another method to be considered is Surface Plasmon Resonance (SPR). SPR can detect binding of label free molecules on the surface of a chip. If the desired protein is an antibody, binding can be translated to directly to the activity of the protein. One can express the active concentration of the protein as the percent of the total protein. SPR can be a powerful method for quickly determining protein activity and overall yield. It is a powerful technology that requires an instrument to perform.

Methods of protein purification. The methods used in protein purification can roughly be divided into analytical and preparative methods. The distinction is not exact, but the deciding factor is the amount of protein that can practically be purified with that method. Analytical methods aim to detect and identify a protein in a mixture, whereas preparative methods aim to produce large quantities of the protein for other purposes, such as structural biology or industrial use.

Depending on the source, the protein has to be brought into solution by breaking the tissue or cells containing it. There are several methods to achieve this: Repeated freezing and thawing, sonication, homogenization by high pressure, filtration (either via cellulose-based depth filters or cross-flow filtration), or permeabilization by organic solvents. The method of choice depends on how fragile the protein is and how sturdy the cells are. After this extraction process soluble proteins will be in the solvent, and can be separated from cell membranes, DNA etc. by centrifugation. The extraction process also extracts proteases, which will start digesting the proteins in the solution. If the protein is sensitive to proteolysis, it is usually desirable to proceed quickly, and keep the extract cooled, to slow down proteolysis.

In bulk protein purification, a common first step to isolate proteins is precipitation with ammonium sulfate $(NH_4)_2SO_4$. This is performed by adding increasing amounts of ammonium sulfate and collecting the different fractions of precipitate protein. One advantage of this method is that it can be performed inexpensively with very large volumes.

The first proteins to be purified are water-soluble proteins. Purification of integral membrane proteins requires disruption of the cell membrane in order to isolate any one particular protein from others that are in the same membrane compartment. Sometimes a particular membrane fraction can be isolated first, such as isolating mitochondria from cells before purifying a protein located in a mitochondrial membrane. A detergent such as sodium dodecyl sulfate (SDS) can be used to dissolve cell membranes and keep membrane proteins in solution during purification; however, because SDS causes denaturation, milder detergents such as Triton X-100 or CHAPS can be used to retain the protein's native conformation during complete purification.

Centrifugation is a process that uses centrifugal force to separate mixtures of particles of varying masses or densities suspended in a liquid. When a vessel (typically a tube or bottle) containing a mixture of proteins or other particulate matter, such as bacterial cells, is rotated at high speeds, the angular momentum yields an outward force to each particle that is proportional to its mass. The tendency of a given particle to move through the liquid because of this force is offset by the resistance the liquid exerts on the particle. The net effect of "spinning" the sample in a centrifuge is that massive, small, and dense particles move outward faster than less massive particles or particles with more "drag" in the liquid. When suspensions of particles are "spun" in a centrifuge, a "pellet" may form at the bottom of the vessel that is enriched for the most massive particles with low drag in the liquid. Non-compacted particles still remaining mostly in the liquid are called the "supernatant" and can be removed from the vessel to separate the supernatant from the pellet. The rate of centrifugation is specified by the angular acceleration applied to the sample, typically measured in comparison to the g. If samples are centrifuged long enough, the particles in the vessel will reach equilibrium wherein the particles accumulate specifically at a point in the vessel where their buoyant density is balanced with centrifugal force. Such an "equilibrium" centrifugation can allow extensive purification of a given particle.

Sucrose gradient centrifugation is a linear concentration gradient of sugar (typically sucrose, glycerol, or a silica based density gradient media, like Percoll™) is generated in a tube such that the highest concentration is on the bottom and lowest on top. A protein sample is then layered on top of the gradient and spun at high speeds in an ultracentrifuge. This causes heavy macromolecules to migrate towards the bottom of the tube faster than lighter material. After separating the protein/particles, the gradient is then fractionated and collected.

Usually a protein purification protocol contains one or more chromatographic steps. The basic procedure in chromatography is to flow the solution containing the protein through a column packed with various materials. Different proteins interact differently with the column material, and can thus be separated by the time required to pass the column, or the conditions required to elute the protein from the column. Usually proteins are detected as they are coming off the column by their absorbance at 280 nm. Many different chromatographic methods exist:

Chromatography can be used to separate protein in solution or denaturing conditions by using porous gels. This technique is known as size exclusion chromatography. The principle is that smaller molecules have to traverse a larger volume in a porous matrix. Consequentially, proteins of a certain range in size will require a variable volume of eluent (solvent) before being collected at the other end of the column of gel.

In the context of protein purification, the eluant is usually pooled in different test tubes. All test tubes containing no measurable trace of the protein to purify are discarded. The remaining solution is thus made of the protein to purify and any other similarly-sized proteins.

Ion exchange chromatography separates compounds according to the nature and degree of their ionic charge. The column to be used is selected according to its type and strength of charge. Anion exchange resins have a positive charge and are used to retain and separate negatively charged compounds, while cation exchange resins have a negative charge and are used to separate positively charged molecules. Before the separation begins a buffer is pumped through the column to equilibrate the opposing charged ions. Upon injection of the sample, solute molecules will exchange with the buffer ions as each competes for the binding sites on the resin. The length of retention for each solute depends upon the strength of its charge. The most weakly charged compounds will elute first, followed by those with successively stronger charges. Because of the nature of the separating mechanism, pH, buffer type, buffer concentration, and temperature all play important roles in controlling the separation.

Affinity Chromatography is a separation technique based upon molecular conformation, which frequently utilizes application specific resins. These resins have ligands attached to their surfaces which are specific for the compounds to be separated. Most frequently, these ligands function in a fashion similar to that of antibody-antigen interactions. This "lock and key" fit between the ligand and its target compound makes it highly specific, frequently generating a single peak, while all else in the sample is unretained.

Many membrane proteins are glycoproteins and can be purified by lectin affinity chromatography. Detergent-solubilized proteins can be allowed to bind to a chromatography resin that has been modified to have a covalently attached lectin. Proteins that do not bind to the lectin are washed away and then specifically bound glycoproteins can be eluted by adding a high concentration of a sugar that competes with the bound glycoproteins at the lectin binding site. Some lectins have high affinity binding to oligosaccharides of glycoproteins that is hard to compete with sugars, and bound glycoproteins need to be released by denaturing the lectin.

A common technique involves engineering a sequence of 6 to 8 histidines into the N- or C-terminal of the protein. The polyhistidine binds strongly to divalent metal ions such as nickel and cobalt. The protein can be passed through a column containing immobilized nickel ions, which binds the polyhistidine tag. All untagged proteins pass through the column. The protein can be eluted with imidazole, which competes with the polyhistidine tag for binding to the column, or by a decrease in pH (typically to 4.5), which decreases the affinity of the tag for the resin. While this procedure is generally used for the purification of recombinant proteins with an engineered affinity tag (such as a 6xHis tag or Clontech's HAT tag), it can also be used for natural proteins with an inherent affinity for divalent cations.

Immunoaffinity chromatography uses the specific binding of an antibody to the target protein to selectively purify the protein. The procedure involves immobilizing an antibody to a column material, which then selectively binds the protein, while everything else flows through. The protein can be eluted by changing the pH or the salinity. Because this method does not involve engineering in a tag, it can be used for proteins from natural sources.

Another way to tag proteins is to engineer an antigen peptide tag onto the protein, and then purify the protein on a column or by incubating with a loose resin that is coated with an immobilized antibody. This particular procedure is known as immunoprecipitation. Immunoprecipitation is quite capable of generating an extremely specific interaction which usually results in binding only the desired protein. The purified tagged proteins can then easily be separated from the other proteins in solution and later eluted back into clean solution. Tags can be cleaved by use of a protease. This often involves engineering a protease cleavage site between the tag and the protein.

High performance liquid chromatography or high pressure liquid chromatography is a form of chromatography applying high pressure to drive the solutes through the column faster. This means that the diffusion is limited and the resolution is improved. The most common form is "reversed phase" hplc, where the column material is hydrophobic. The proteins are eluted by a gradient of increasing amounts of an organic solvent, such as acetonitrile. The proteins elute according to their hydrophobicity. After purification by HPLC the protein is in a solution that only contains volatile compounds, and can easily be lyophilized. HPLC purification frequently results in denaturation of the purified proteins and is thus not applicable to proteins that do not spontaneously refold.

At the end of a protein purification, the protein often has to be concentrated. Different methods exist. If the solution doesn't contain any other soluble component than the protein in question the protein can be lyophilized (dried). This is commonly done after an HPLC run. This simply removes all volatile component leaving the proteins behind.

Ultrafiltration concentrates a protein solution using selective permeable membranes. The function of the membrane is to let the water and small molecules pass through while retaining the protein. The solution is forced against the membrane by mechanical pump or gas pressure or centrifugation.

Gel electrophoresis is a common laboratory technique that can be used both as preparative and analytical method. The principle of electrophoresis relies on the movement of a charged ion in an electric field. In practice, the proteins are denatured in a solution containing a detergent (SDS). In these conditions, the proteins are unfolded and coated with negatively charged detergent molecules. The proteins in SDS-PAGE are separated on the sole basis of their size.

In analytical methods, the protein migrate as bands based on size. Each band can be detected using stains such as Coomassie blue dye or silver stain. Preparative methods to purify large amounts of protein, require the extraction of the protein from the electrophoretic gel. This extraction may involve excision of the gel containing a band, or eluting the band directly off the gel as it runs off the end of the gel.

In the context of a purification strategy, denaturing condition electrophoresis provides an improved resolution over size exclusion chromatography, but does not scale to large quantity of proteins in a sample as well as the late chromatography columns.

F. Modification Moieties

5mC and/or 5hmC can be directly or indirectly modified with a number of functional groups or labeled molecules. One example is the oxidation of 5mC and the subsequent labeling with a functionalized or labeled glucose molecule. In certain embodiments, 5mC can be first modified with a modification moiety or a functional group prior to being further modified by the attachment of a glucosyl moiety.

In additional embodiments, a functionalized or labeled glucose molecule can be used in conjunction with βGT to modify 5hmC in a nucleic polymer such as DNA or RNA. In certain aspects, the βGT UDP substrate comprises a functionalized or labeled glucose moiety.

In a further aspect, the modification moiety can be modified or functionalized using click chemistry or other coupling chemistries known in the art. Click chemistry is a chemical philosophy introduced by K. Barry Sharpless in 2001 (Kolb et al., 2001; Evans, 2007) and describes chemistry tailored to generate substances quickly and reliably by joining small units.

The modification moiety can be directly or indirectly coupled to a label. The label can be any label that is detected, or is capable of being detected. Examples of suitable labels include, e.g., chromogenic label, a radiolabel, a fluorescent label, and a biotinylated label. Thus, the label can be, e.g., fluorescent glucose, biotin-labeled glucose, radiolabeled glucose and the like. In certain aspects, the label is a chromogenic label. The term "chromogenic label" includes all agents that have a distinct color or otherwise detectable marker. In addition to chemical structures having intrinsic, readily-observable colors in the visible range, other markers used include fluorescent groups, biotin tags, enzymes (that may be used in a reaction that results in the formation of a colored product), magnetic and isotopic markers, and so on. The foregoing list of detectable markers is for illustrative purposes only, and is in no way intended to be limiting or exhaustive.

The label may be attached to the agent using methods known in the art. Labels include any detectable group attached to the glucose molecule, or detection agent that does not interfere with its function. Further labels that may be used include fluorescent labels, such as Fluorescein, Texas Red, Lucifer Yellow, Rhodamine, Nile-red, tetramethyl-rhodamine-5-isothiocyanate, 1,6-diphenyl-1,3,5-hexatriene, cis-Parinaric acid, Phycoerythrin, Allophycocyanin, 4',6-diamidino-2-phenylindole (DAPI), Hoechst 33258, 2-aminobenzamide, and the like. Further labels include electron dense metals, such as gold, ligands, haptens, such as biotin, radioactive labels.

A fluorophore contains or is a functional group that will absorb energy of a specific wavelength and re-emit energy at a different (but equally specific) wavelength. The amount and wavelength of the emitted energy depend on both the fluorophore and the chemical environment of the fluorophore. Fluorophores can be attached to protein using functional groups and or linkers, such as amino groups (Active ester, Carboxylate, Isothiocyanate, hydrazine); carboxyl groups (carbodiimide); thiol (maleimide, acetyl bromide); azide (via click chemistry or non-specifically (glutaraldehyde).

Fluorophores can be proteins, quantum dots (fluorescent semiconductor nanoparticles), or small molecules. Common dye families include, but are not limited to Xanthene derivatives: fluorescein, rhodamine, Oregon green, eosin, Texas red etc.; Cyanine derivatives: cyanine, indocarbocyanine, oxacarbocyanine, thiacarbocyanine and merocyanine; Naphthalene derivatives (dansyl and prodan derivatives); Coumarin derivatives; oxadiazole derivatives: pyridyloxazole, nitrobenzoxadiazole and benzoxadiazole; Pyrene derivatives: cascade blue etc.; BODIPY (Invitrogen); Oxazine derivatives: Nile red, Nile blue, cresyl violet, oxazine 170 etc.; Acridine derivatives: proflavin, acridine orange, acridine yellow etc.; Arylmethine derivatives: auramine, crystal violet, malachite green; CF dye (Biotium); Alexa Fluor (Invitrogen); Atto and Tracy (Sigma Aldrich); FluoProbes (Interchim); Tetrapyrrole derivatives: porphin, phtalocyanine, bilirubin; cascade yellow; azure B; acridine orange; DAPI; Hoechst 33258; Lucifer yellow; piroxicam; quinine and anthraqinone; squarylium; oligophenylenes; and the like.

Other fluorophores include: Hydroxycoumarin; Aminocoumarin; Methoxycoumarin; Cascade Blue; Pacific Blue; Pacific Orange; Lucifer yellow; NBD; R-Phycoerythrin (PE); PE-Cy5 conjugates; PE-Cy7 conjugates; Red 613; PerCP; TruRed; FluorX; Fluorescein; BODIPY-FL; TRITC; X-Rhodamine; Lissamine Rhodamine B; Texas Red; Allophycocyanin; APC-Cy7 conjugates.

Alexa Fluor dyes (Molecular Probes) include: Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, and Alexa Fluor 790.

Cy Dyes (GE Heathcare) include Cy2, Cy3, Cy3B, Cy3.5, Cy5, Cy5.5 and Cy7.

Nucleic acid probes include Hoechst 33342, DAPI, Hoechst 33258, SYTOX Blue, Chromomycin A3, Mithramycin, YOYO-1, Ethidium Bromide, Acridine Orange, SYTOX Green, TOTO-1, TO-PRO-1, TO-PRO: Cyanine Monomer, Thiazole Orange, Propidium Iodide (PI), LDS 751, 7-AAD, SYTOX Orange, TOTO-3, TO-PRO-3, and DRAQ5.

Cell function probes include Indo-1, Fluo-3, DCFH, DHR, SNARF.

Fluorescent proteins include Y66H, Y66F, EBFP, EBFP2, Azurite, GFPuv, T-Sapphire, Cerulean, mCFP, ECFP, CyPet, Y66W, mKeima-Red, TagCFP, AmCyan1, mTFP1, S65A, Midoriishi Cyan, Wild Type GFP, S65C, TurboGFP, TagGFP, S65L, Emerald, S65T (Invitrogen), EGFP (Clontech), Azami Green (MBL), ZsGreen1 (Clontech), TagYFP (Evrogen), EYFP (Clontech), Topaz, Venus, mCitrine, YPet, TurboYFP, ZsYellow1 (Clontech), Kusabira Orange (MBL), mOrange, mKO, TurboRFP (Evrogen), tdTomato, TagRFP (Evrogen), DsRed (Clontech), DsRed2 (Clontech), mStrawberry, TurboFP602 (Evrogen), AsRed2 (Clontech), mRFP1, J-Red, mCherry, HcRed1 (Clontech), Katusha, Kate (Evrogen), TurboFP635 (Evrogen), mPlum, and mRaspberry.

1. Click Chemistry

The Huisgen 1,3-dipolar cycloaddition, in particular the Cu(I)-catalyzed stepwise variant, is often referred to simply as the "click reaction". The Cu(I)-catalyzed variant (Tornoe et al., 2002) was first reported by Morten Meldal and co-workers from Carlsberg Laboratory, Denmark for the synthesis of peptidotriazoles on solid support. Fokin and Sharpless independently described it as a reliable catalytic process offering "an unprecedented level of selectivity, reliability, and scope for those organic synthesis endeavors which depend on the creation of covalent links between diverse building blocks", firmly placing it among the most reliable processes fitting the click criteria.

One of the most popular reactions within the click chemistry philosophy is the azide alkyne Huisgen cycloaddition using a Cu catalyst at room temperature discovered concurrently and independently by the groups of K. Barry Sharpless and Morten Meldal. This was an improvement over the same reaction first popularized by Rolf Huisgen in the 1970s, albeit at elevated temperatures in the absence of water and without a Cu catalyst (it is explained fully in 1,3-Dipolar Cycloaddition Chemistry, published by Wiley and updated in 2002). However, the azides and alkynes are both kinetically stable. Copper and Ruthenium are the commonly used catalysts in the reaction.

Copper catalyzed click reactions work essentially on terminal alkynes. The Cu species undergo metal insertion reaction into the terminal alkynes. Commonly used solvents are polar aprotic solvents such as THF, DMSO, $CH_3CN$, DMF as well as in non-polar aprotic solvents such as toluene. Neat solvents or a mixture of solvents may be used.

Click chemistry has widespread applications. Some of them are: preparative organic synthesis of 1,4-substituted triazoles; modification of peptide function with triazoles; modification of natural products and pharmaceuticals; drug discovery; macrocyclizations using Cu(1) catalyzed triazole couplings; modification of DNA and nucleotides by triazole ligation; supramolecular chemistry: calixarenes, rotaxanes, and catenanes; dendrimer design; carbohydrate clusters and carbohydrate conjugation by Cu(1) catalyzed triazole ligation reactions; polymers; material science; and nanotechnology (Moses and Moorhouse, 2007; Hein et al., 2008, each of which is incorporated herein by reference).

2. Biotinylation of 5mC in Genomic DNA for Affinity Purification

In certain aspects the functional group installed on 5mC can be readily labeled with commercially available maleimide or alkyne (click chemistry) linked with a biotin, respectively. The reaction of thiol with maleimide is highly efficient; however, this labeling reaction cannot tolerate proteins or small molecules that bear thiol groups. Thus, genomic DNA must be isolated from other cellular components prior to the labeling, which can be readily achieved. The azide labeling with commercially available biotin-linked alkyne is completely bio-orthogonal, thus genomic DNA with bound proteins can be directly used. In both cases, the biotin-labeled DNA fragments may pulled down with streptavidin and submitted for high-throughput sequencing in order to map out global distributions and the locations of 5mC in the chromosome. This will reveal a distribution map of 5mC in genomic DNA at different development stages of a particular cell or cell line.

3. Labeling 5mC with a Photosensitizer

An alternative strategy that does not rely on converting 5mC:G base pair to a different base pair is to tether a photosensitizer to 5mC. Photosensitized one-electron oxidation can lead to site-specific oxidation of the modified 5mC or the nearby guanines (Tanabe et al., 2007; Meyer et al., 2003). Subsequent base (piperidine) treatment will lead to specific strand cleavage on the oxidized site (Tanabe et al., 2007; Meyer et al., 2003). Thus, genomic DNA containing 5mC labeled with photosensitizer can be subjected to photo-oxidation and base treatment. DNA fragments will be generated with oxidation sites at the end. High-throughput sequencing will reveal these modification sites.

4. Attachment of a Sterically Bulky Group to 5mC

In another strategy, a sterically bulky group such as polyethyleneglycol (PEG), a dendrimer, or a protein such as streptavidin can be introduced to the thiol- or azide-modified 5mC. Although 5mC in duplex DNA does not interfere with the polymerization reaction catalyzed by various different polymerases, the presence of an additional bulky group on 5mC on the DNA template strand can interfere with the synthesis of the new strand by DNA polymerase. As a result, primer extension will lead to a partially extended primer of certain length. The modification sites can be revealed by sequencing the partially extended primers. This method can be very versatile. It can be used to determine the modification sites for a given promoter site of interest. A high-throughput format can be developed as well. DNA fragments containing multiple 5mC can be affinity purified and random or designed primers can be used to perform primer extension experiments on these DNA fragments. Partially extended primers can be collected and subjected to high-throughput sequencing using a similar protocol as described in the restriction enzyme digestion method. A bulky modification may stop the polymerization reaction a few bases ahead of the modification site. Still, this method will map the modification sites to the resolution of a few bases. Considering that most 5mC exists in a CpG sequence, the resolution can be adequate for most applications. With a bulky substitution on 5mC digestion of modified DNA by restriction enzymes could be blocked for the restriction enzyme digestion-based assay.

5. Synthesis of Modified Uridine Diphosphate Glucose (UDP-Glu) Bearing Thiol or Azide.

Figures 7A, 7B:
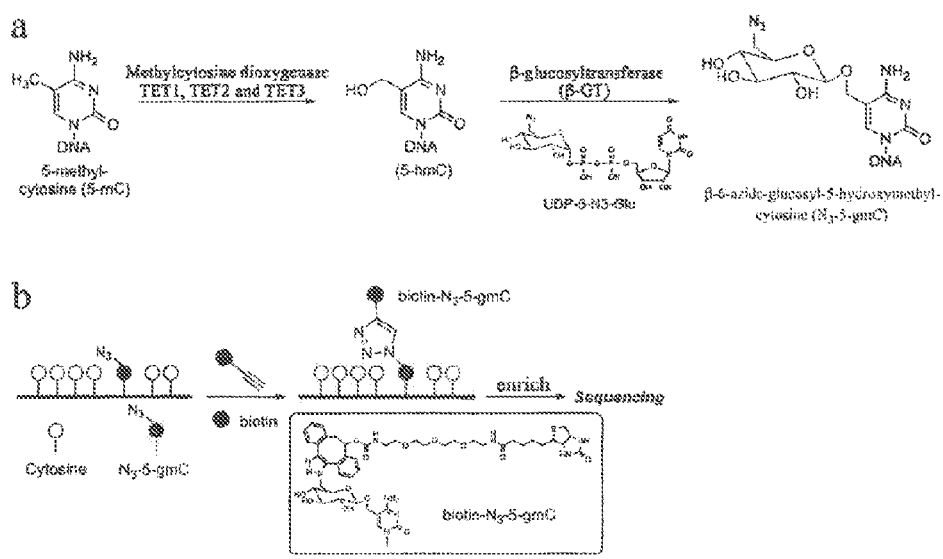

The initial success of 5hmC glycosylation led to the hypothesis that thiol- or azide-modified glucose can be similarly transferred to 5hmC in duplex DNA. Thus, the inventors have synthesized azide-substituted UDP-Glu and contemplate synthesizing thiol-substituted UDP-Glu for 5hmC labeling. An azide tag is preferred since this functional group is not present inside cells. The click chemistry to label this group is completely bio-orthogonal, meaning no interference from biological samples (Kolb et al., 2001). An azide-substituted UDP-Glu is shown in FIG. 7A. The azide-substituted glucoses can be transferred to 5hmC, see Song et al., 2011, which is incorporated herein by reference.

6. Biotinylation of 5hmC in Genomic DNA for Affinity Purification

The functional group installed on 5gmC can be readily labeled with commercially available maleimide or alkyne (click chemistry) linked with a biotin, respectively. The reaction of thiol with maleimide is highly efficient; however, this labeling reaction cannot tolerate proteins or small molecules that bear thiol groups. Thus, genomic DNA must be isolated from other cellular components prior to the labeling, which can be readily achieved. The azide labeling with commercially available biotin-linked alkyne is completely bio-orthogonal, thus genomic DNA with bound proteins can be directly used. In both cases, the biotin-labeled DNA fragments may pulled down with streptavidin and submitted for high-throughput sequencing in order to map out global distributions and the locations of 5hmC in chromosome. This will reveal a distribution map of 5hmC in genomic DNA at different development stages of a particular cell or cell line.

7. Labeling 5gmC with a Photosensitizer

An alternative strategy that does not rely on converting 5hmC:G base pair to a different base pair is to tether a photosensitizer to 5-gmC. Photosensitized one-electron oxidation can lead to site-specific oxidation of the modified 5-gmC or the nearby guanines (Tanabe et al., 2007; Meyer et al., 2003). Subsequent base (piperidine) treatment will lead to specific strand cleavage on the oxidized site (Tanabe et al., 2007; Meyer et al., 2003). Thus, genomic DNA containing 5-gmC labeled with photosensitizer can be subjected to photo-oxidation and base treatment. DNA fragments will be generated with oxidation sites at the end. High-throughput sequencing will reveal these modification sites.

8. Attachment of a Sterically Bulky Group to 5gmC

In another strategy, a sterically bulky group such as polyethyleneglycol (PEG), a dendrimer, or a protein such as streptavidin can be introduced to the thiol- or azide-modified 5gmC. Although 5gmC in duplex DNA does not interfere with the polymerization reaction catalyzed by various different polymerases, the presence of an additional bulky group on 5-gmC on the DNA template strand can interfere with the synthesis of the new strand by DNA polymerase. As a result, primer extension will lead to a partially extended primer of certain length. The modification sites can be revealed by sequencing the partially extended primers. This method can be very versatile. It can be used to determine the modification sites for a given promoter site of interest. A high-throughput format can be developed as well. DNA fragments containing multiple 5hmC can be affinity purified and random or designed primers can be used to perform primer extension experiments on these DNA fragments. Partially extended primers can be collected and subjected to high-throughput sequencing using a similar protocol as described in the restriction enzyme digestion method. A bulky modification may stop the polymerization reaction a few bases ahead of the modification site. Still, this method will map the modification sites to the resolution of a few bases. Considering that most 5hmC exists in a CpG sequence, the resolution can be adequate for most applications. With a bulky substitution on 5gmC digestion of modified DNA by restriction enzymes could be blocked for the restriction enzyme digestion-based assay.

III. Assays Utilizing 5mC and/or 5hmC Modification

Nucleic acid analysis and evaluation includes various methods of amplifying, fragmenting, and/or hybridizing nucleic acids that have or have not been modified.

A. Genomic Analysis

Methodologies are available for large scale sequence analysis. In certain aspects, the methods described exploit these genomic analysis methodologies and adapt them for uses incorporating the methodologies described herein. In certain instances the methods can be used to perform high resolution methylation and/or hydroxymethylation analysis on several thousand CpGs in genomic DNA. Therefore, methods are directed to analysis of the methylation and/or hydroxymethylation status of a genomic DNA sample, comprising one or more of the steps: (a) fragmenting the sample and enriching the sample for sequences comprising CpG islands, (b) generating a single stranded DNA library, (c) subjecting the sample to one or more modification treatments, (d) amplifying individual members of the single stranded DNA library by means of PCR, e.g., emulsion PCR, and (e) sequencing the amplified single stranded DNA library.

The present methods allow for analyzing the methylation and/or hydroxymethylation status of all regions of a complete genome, where changes in methylation and/or hydroxymethylation status are expected to have an influence on gene expression. Due to the combination of the modification treatment, amplification and high throughput sequencing, it is possible to analyze the methylation and/or hydroxymethylation status of at least 1000 and preferably 5000 or more CpG islands in parallel.

A "CpG island" as used herein refers to regions of DNA with a high G/C content and a high frequency of CpG dinucleotides relative to the whole genome of an organism of interest. Also used interchangeably in the art is the term "CG island." The 'p' in "CpG island" refers to the phosphodiester bond between the cytosine and guanine nucleotides.

DNA may be isolated from an organism of interest, including, but not limited to eukaryotic organisms and prokaryotic organisms, preferably mammalian organisms, such as humans.

In certain aspects, the step of enriching a sample for sequences comprising CpG islands can be done in different ways. One technique for enrichment is immunoprecipitation of methylated DNA using a methyl-Cytosine specific antibody (Weber et al., 2005). Alternatively, an enrichment step can comprise digesting the sample with a one or more restriction enzymes which more frequently cut regions of DNA comprising no CpG islands and less frequently cut regions comprising CpG islands, and isolating DNA fragments with a specific size range.

The inventors have demonstrated that while the methylation-insensitive restriction enzyme MspI can completely cut C(5-meC)GG and partially cut C(5hmC)GG, its activity is completely blocked by C(ghmC)GG. This indicates that the introduction of a modification moiety can change the property of 5mC or 5hmC in duplex DNA. With bulkier groups on 5mC or 5hmC, digestions by other restriction enzymes that recognize DNA sequences containing CpG can be blocked. Since modified 5mC can block restriction enzyme digestion, the genomic DNA with modified ghmC can be treated with and without restriction enzymes and subjected to known methods of mapping the genome-wide distribution and location of the 5mC and/or 5hmC modifications.

Such restrictions enzymes can be selected by a person skilled in the art using conventional Bioinformatics approaches. The selection of appropriate enzymes also has a substantial influence on the average size of fragments that ultimately will be generated and sequenced. The selection of appropriate enzymes may be designed in such a way that it promotes enrichment of a certain fragment length. Thus, the selection may be adjusted to the kind of sequencing method which is finally applied. For most sequencing methods, a fragment length between 100 and 1000 by has been proven to be efficient. Therefore, in one embodiment, said fragment size range is from 100, 200 or 300 base pairs to 400, 500, 600, 700, 800, 900, or 1000 base pairs (bp), including all ranges and values there between.

The human genome reference sequence (NCBI Build 36.1 from March 2006; assembled parts of chromosomes only) has a length of 3,142,044,949 bp and contains 26,567 annotated CpG islands (CpGs) for a total length of 21,073,737 bp (0.67%). In certain aspects, a DNA sequence read hits a CpG if the read overlaps with the CpG by at least 50 bp.

As a non-limiting example, the following enzymes or their isoschizomers (with the following restriction sites) can be used for a method according to the present invention: MseI (TTAA), Tsp509 (AATT), AluI (AGCT), N1aIII (CATG), BfaI (CTAG), HpyCH4 (TGCA), Dpul (GATC), MboII (GAAGA), M1yI (GAGTC), BCCI (CCATC). Isoschizomers are pairs of restriction enzymes specific to the same recognition sequence and cut in the same location.

Embodiments include a CG island enriched library produced from genomic DNA by digestion with several restriction enzymes that preferably cut within non-CG island regions. In certain aspects, the restriction enzymes are selected in such a way that digestion can result in fragments with a size range between 300, 400, 500, 600 to 500, 600, 800, 900 bp or greater, including all ranges and values there between. The library fragments are ligated to adaptors. Subsequently, a conventional bisulfite treatment is performed according to methods that are well known in the art. As a result, unmethylated cytosine residues are converted to Uracil residues, which in a subsequent sequencing reaction base calling are identified as "T" instead of "C", when compared with a non bisulfite treated reference. Subsequent to bisulfite treatment, the sample is subjected to a conventional sequencing protocol.

As one example, the 454 Genome Sequencer System supports the sequencing of samples from a wide variety of starting materials including, but not limited to, eukaryotic or bacterial genomic DNA. Genomic DNAs are fractionated into small, 100- to 1000-bp fragments with an appropriate specific combination of restriction enzymes which enriches for CpG island containing fragments. In one embodiment, the restriction enzymes used for a method according to the present invention are selected from a group consisting of MseI, Tsp509, AluI, N1aIII, BfaI, HpyCH4, Dpul, MboII, M1yI, and BCCI, or any isoschizomer of any of the enzymes mentioned. Preferably, 4-5 different enzymes are selected.

Using a series of standard molecular biology techniques, short adaptors (A and B) are added to each fragment. The adaptors are used for purification, amplification, and sequencing steps. Single-stranded fragments with A and B adaptors compose the sample library used for subsequent steps.

Prior to ligation of the adaptors, the fragments can be completely double stranded without any single stranded overhang. A fragment polishing reaction is performed using e.g. E. coli T4 DNA polymerase. In one embodiment, the polishing reaction is performed in the presence of hydroxymethyl-dCTP instead of dCTP. In another embodiment, the fragment polishing reaction is performed in the presence of a DNA polymerase which lacks proofreading activity, such as Tth DNA polymerase (Roche Applied Science Cat. No: 11 480 014 001).

The two different double stranded adaptors A and B are ligated to the ends of the fragments. Some or all of the C-residues of adaptors A and B can be methyl-C or hydroxymethyl-C residues. Subsequently, the fragments containing at least one B adaptor are immobilized on a streptavidin coated solid support and a nick repair-fill-in synthesis is performed using a strand displacement enzyme such as Bst Polymerase (New England Biolabs). Preferably said reaction is performed in the presence of hydroxymethyl –dCTP instead of dCTP. Subsequently single stranded molecules comprising one adaptor A and one adaptor B are removed from the streptavidin coated beads as disclosed in (Margulies et al., 2005). In those cases where methyl or hydroxymethyl –dCTP replaces dCTP, it can be used at the same concentrations as dCTP is used in the original protocol.

Bisulfite treatment can be done according to standard methods that are well known in the art (Frommer et al., 1992; Zeschnigk et al., 1997; Clark et al., 1994). The sample can be purified, for example by a Sephadex size exclusion column or, at least by means of precipitation. It is also within the scope of the present invention, if directly after bisulfite treatment, or directly after bisulfite treatment followed by purification, the sample is amplified by means of performing a conventional PCR using amplification primers with sequences corresponding to the A and B adaptor sequences.

In certain aspects, the bisulfite treated and optionally purified and/or amplified single-stranded DNA library is immobilized onto specifically designed DNA Capture Beads. Each bead carries a unique single-stranded DNA library fragment.

A library fragment can be amplified within its own microreactor comprised of a water-in-oil emulsion, excluding competing or contaminating sequences. Amplification of the entire fragment collection can be done in parallel; for each fragment, this results in a copy number of several million clonally amplified copies of the unique fragment per bead. After PCR amplification within the emulsion, the emulsion is broken while the amplified fragments remain bound to their specific beads.

The inventors developed a relatively cost-effective approach for assessing DNA methylation on a genomic scale by coupling affinity-based enrichment of methylated DNA, with high-throughput sequencing. The development of 5mC specific antibodies has enabled genomic DNA methylation profiling in various biological systems. However, the primary pitfall associated with 5mC immunoprecipitation is methyl-CpG density dependent biases, which ultimately inhibit access to certain portions of the methylome. In addition, various factors contribute to inconsistency of results obtained from independent experiments.

A robust, 5mC-specific chemical tagging approach is described herein. This approach utilizes a covalent linkage and a high-affinity biotin/streptavidin interaction to improve upon the variability of 5mC enrichment associated with the currently used MeDIP- and MBD-Seq type procedures that are introduced by antibody/protein sources and other factors such as salt concentrations. TAmC-Seq is both highly sensitive and specific for 5mC, while also capturing a larger fraction of CpG-dinucleotides with far fewer reads than MeDIP-Seq. Furthermore, TAmC-Seq provides a wider range of access to genomic regions with varying CpG-dinucleotide frequencies, reducing CpG-density dependent biases relative to MeDIP-Seq. Moreover, use of the same biotin/streptavidin interaction for pull-down of 5mC and 5hmC eliminates the potential variability associated with differences in the affinity of the capture reagent toward 5mC versus 5hmC that may be introduced when using, for instance, different antibodies against each mark. TAmC-Seq improves genome-wide correlations between 5mC and 5hmC and that 5mC signals at 5hmC enriched loci are increased in comparison to MeDIP. Thus, parallel application of chemical tagging procedures for 5mC and 5hmC may further refine interpretations of each mark in relation to the other. TAmC-Seq thereby offers a robust means of facilitating cost-effective enrichment and epigenomic profiling of DNA methylation.

A genome-wide approach has been developed to determine 5hmC distribution at base resolution. The inventors have generated the first base-resolution maps of 5hmC in both human and mouse ESCs. These maps provide a template for further understanding the biological roles of 5hmC in stem cells as well as gene regulation in general. In conjunction with methylC-Seq, the TAB-Seq method described herein represents a general approach to measure the absolute abundance of 5mC and 5hmC at specific sites or genome-wide, which could be widely applied to various cell types and tissues.

The TAB-Seq technique was applied to mammalian genomes to generate single-base resolution maps of 5hmC in human and mouse ESCs. These maps agree well with previous maps generated using affinity-based 5hmC profiling, recovering over 80% of 5hmC-enriched sites. Importantly, these single-base maps also revealed a significant number of new 5hmC sites. Analyses of two 5hmC maps in ESCs identified a number of novel sequence-based characteristics of 5hmC that were previously unknown. Much like 5mC, 5hmC tends to occur primarily at CpG-dinucleotides yet, unlike 5mC, exhibits an asymmetric strand bias. A relatively strong local sequence preference surrounding 5hmC, with 5hmC occurring within a G-rich context, has also been observed. These sequence-based features associated with 5hmC provides a basis for future mechanistic insight into the means by which 5hmC is deposited, recognized, and dynamically regulated.

The ability to quantify 5hmC abundance with base resolution offered the unique opportunity to assess its relative abundance at various regulatory elements and genomic annotations without bias. In contrast to the nearly uniform distribution of 5mC outside of promoter regions, the abundance of 5hmC varies among different classes of functional sequences. It is most enriched at distal regulatory regions where levels of 5mC are correspondingly lower than the genome average. This observation agrees with recent findings from others (Stadler et al., 2011), and suggests that active demethylation occurs at active regulatory elements through a hydroxymethylated intermediate. This active demethylation is distributed around, but not within, transcription factor consensus motifs. Supporting the notion of active demethylation, total DNA methylation exhibits a strong negative correlation with 5hmC at distal regulatory elements (Spearman correlation=−0.30). One interesting observation of these distal cis-regulatory elements is that 5hmC and 5mC often occur together at the same cytosine. Application of TAB-Seq to experimental model systems should allow further elucidation of the mechanisms.

Previous affinity-based studies have suggested enrichment of 5hmC at CpG-rich transcription start sites. However, these observations relied heavily on antibody-base detection, which has been shown to exhibit bias toward 5hmC dense regions (Ficz et al., 2011; Pastor et al., 2011; Stroud et al., 2011; Szulwach et al., 2011a; Williams et al., 2011; Wu et al., 2011; Xu et al., 2011). Using the approach described herein, it has been found that, in general, 5hmC is most abundant at regions of low CpG content. Furthermore, even promoters with relatively high 5hmC content tend to have low CpG content in both mouse and human ESCs. These findings highlight the utility of a base-resolution method for measuring 5hmC abundance, and provide new insight into its dynamic regulation at promoter sites with distinct CpG content.

Tahiliani and colleagues (Tahiliani et al., 2009) recently estimated the genome-wide abundance of 5hmC to be about 14 times less than that of 5mC, which would correspond to ~4.4 million hydroxymethylcytosines in human. However, as indicated here that the base-level abundance of 5hmC is several times lower than 5mC, this is likely an underestimate. The comparatively low number of 5hmCs confidently detected in this study (691,414) is likely explained by the frequent hydroxymethylation of gene bodies previously observed in affinity-based studies (Ficz et al., 2011; Pastor et al., 2011; Stroud et al., 2011; Szulwach et al., 2011a; Williams et al., 2011; Wu et al., 2011; Xu et al., 2011). Since genic cytosines likely exist at a relatively low abundance of 5hmC (between 3-4%), they would have escaped detection at the current sequencing depth. In order to resolve low abundance hydroxymethylcytosines at single-base precision, significantly more sequencing (upwards of 100× coverage per strand) would be required. This observation highlights the biases inherent in affinity-based 5hmC mapping, which can easily amplify frequent weak signals found in gene bodies to overshadow rare but stronger ones at distal regulatory elements.

B. Modification Sensitive Enzymes.

DNA methyltransferases (MTases) that transfer a methyl group from S-adenosylmethionine to either adenine or cytosine residues, are found in a wide variety of prokaryotes and eukaryotes. Methylation should be considered when digesting DNA with restriction endonucleases because cleavage can be blocked or impaired when a particular base in the recognition site is methylated or otherwise modified.

In prokaryotes, MTases have most often been identified as elements of restriction/modification systems that act to protect host DNA from cleavage by the corresponding restriction endonuclease. Most laboratory strains of E. coli contain three site-specific DNA methylases. Some or all of the sites for a restriction endonuclease may be resistant to cleavage when isolated from strains expressing the Dam or Dcm methylases if the methylase recognition site overlaps the endonuclease recognition site. For example, plasmid DNA isolated from dam+E. coli is completely resistant to cleavage by MboI, which cleaves at GATC sites.

Not all DNA isolated from E. coli is methylated to the same extent. While pBR322 DNA is fully modified (and is therefore completely resistant to MboI digestion), only about 50% of λ DNA Dam sites are methylated, presumably because the methylase does not have the opportunity to methylate the DNA fully before it is packaged into the phage head. As a result, enzymes blocked by Dam or Dcm modification will yield partial digestion patterns with λ DNA. Restriction sites that are blocked by Dam or Dcm methylation can be un-methylated by cloning DNA into a dam–, dcm– strain of E. coli, such as dam–/dcm– Competent E. coli (NEB #C2925).

CpG MTases, found in higher eukaryotes (e.g., Dnmt1), transfer a methyl group to the C5 position of cytosine residues. Patterns of CpG methylation are heritable, tissue specific and correlate with gene expression. Consequently, CpG methylation has been postulated to play a role in differentiation and gene expression (Josse and Kornberg, 1962). The effects of CpG methylation are mainly a concern when digesting eukaryotic genomic DNA. CpG methylation patterns are not retained once the DNA is cloned into a bacterial host.

The table below summarizes methylation sensitivity for NEB restriction enzymes, indicating whether or not cleavage is blocked or impaired by Dam, Dcm or CpG methylation if or when it overlaps each recognition site. REBASE, the restriction enzyme database, can be consulted for more detailed information and specific examples. (Marinus and Morris, 1973; Geier and Modrich, 1979; May and Hattman, 1975; Siegfried and Cedar, 1997).

| Enzyme | Sequence | Dam | Dcm | CpG |
|---|---|---|---|---|
| AatII | GACGT/C | Not Sensitive | Not Sensitive | Blocked |
| Acc65I | G/GTACC | Not Sensitive | Blocked by Some Overlapping Combinations | Blocked by Some Overlapping Combinations |
| AccI | GT/MKAC | Not Sensitive | Not Sensitive | Blocked by Overlapping Methylation |
| AciI | CCGC(-3/-1) | Not Sensitive | Not Sensitive | Blocked |
| AclI | AA/CGTT | Not Sensitive | Not Sensitive | Blocked |
| AcuI | CTGAAG(16/14) | Not Sensitive | Not Sensitive | Not Sensitive |
| AfeI | AGC/GCT | Not Sensitive | Not Sensitive | Blocked |
| AflII | C/TTAAG | Not Sensitive | Not Sensitive | Not Sensitive |
| AflIII | A/CRYGT | Not Sensitive | Not Sensitive | Not Sensitive |

-continued

| Enzyme | Sequence | Dam | Dcm | CpG |
|---|---|---|---|---|
| AgeI | A/CCGGT | Not Sensitive | Not Sensitive | Blocked |
| AgeI-HF ™ | A/CCGGT | — | — | — |
| AhdI | GACNNN/NNGTC | Not Sensitive | Not Sensitive | Impaired by Some Overlapping Combinations |
| AleI | CACNN/NNGTG | Not Sensitive | Not Sensitive | Impaired by Some Overlapping Combinations |
| AluI | AG/CT | Not Sensitive | Not Sensitive | Not Sensitive |
| AlwI | GGATC(4/5) | Blocked | Not Sensitive | Not Sensitive |
| AlwNI | CAGNNN/CTG | Not Sensitive | Blocked by Overlapping Methylation | Not Sensitive |
| ApaI | GGGCC/C | Not Sensitive | Blocked by Overlapping Methylation | Blocked by Overlapping Methylation |
| ApaLI | G/TGCAC | Not Sensitive | Not Sensitive | Blocked by Overlapping Methylation |
| ApeKI | G/CWGC | Not Sensitive | Not Sensitive | Not Sensitive |
| ApoI | R/AATTY | Not Sensitive | Not Sensitive | Not Sensitive |
| AscI | GG/CGCGCC | Not Sensitive | Not Sensitive | Blocked |
| AseI | AT/TAAT | Not Sensitive | Not Sensitive | Not Sensitive |
| AsiSI | GCGAT/CGC | Not Sensitive | Not Sensitive | Blocked |
| AvaI | C/YCGRG | Not Sensitive | Not Sensitive | Blocked |
| AvaII | G/GWCC | Not Sensitive | Blocked by Overlapping Methylation | Blocked by Overlapping Methylation |
| AvrII | C/CTAGG | Not Sensitive | Not Sensitive | Not Sensitive |
| BaeGI | GKGCM/C | Not Sensitive | Not Sensitive | Not Sensitive |
| BaeI | (10/15)ACNNNNGTAYC(12/7) | Not Sensitive | Not Sensitive | Blocked by Some Overlapping Combinations |
| BamHI | G/GATCC | Not Sensitive | Not Sensitive | Not Sensitive |
| BamHI-HF ™ | G/GATCC | Not Sensitive | Not Sensitive | Not Sensitive |
| BanI | G/GYRCC | Not Sensitive | Blocked by Some Overlapping Combinations | Blocked by Some Overlapping Combinations |
| BanII | GRGCY/C | Not Sensitive | Not Sensitive | Not Sensitive |
| BbsI | GAAGAC(2/6) | Not Sensitive | Not Sensitive | Not Sensitive |
| BbvCI | CCTCAGC(-5/-2) | Not Sensitive | Not Sensitive | Impaired by Overlapping Methylation |
| BbvI | GCAGC(8/12) | Not Sensitive | Not Sensitive | Not Sensitive |
| BccI | CCATC(4/5) | Not Sensitive | Not Sensitive | Not Sensitive |
| BceAI | ACGGC(12/14) | Not Sensitive | Not Sensitive | Blocked |

-continued

| Enzyme | Sequence | Dam | Dcm | CpG |
|---|---|---|---|---|
| BcgI | (10/12)CGANNNNNNTGC(12/10) | Blocked by Overlapping Methylation | Not Sensitive | Blocked by Some Overlapping Combinations |
| BciVI | GTATCC(6/5) | Not Sensitive | Not Sensitive | Not Sensitive |
| BclI | T/GATCA | Blocked | Not Sensitive | Not Sensitive |
| BfaI | C/TAG | Not Sensitive | Not Sensitive | Not Sensitive |
| BfuAI | ACCTGC(4/8) | Not Sensitive | Not Sensitive | Impaired by Overlapping Methylation |
| BfuCI | /GATC | Not Sensitive | Not Sensitive | Blocked by Overlapping Methylation |
| BglI | GCCNNNN/NGGC | Not Sensitive | Not Sensitive | Blocked by Some Overlapping Combinations |
| BglII | A/GATCT | Not Sensitive | Not Sensitive | Not Sensitive |
| BlpI | GC/TNAGC | Not Sensitive | Not Sensitive | Not Sensitive |
| BmgBI | CACGTC(-3/-3) | Not Sensitive | Not Sensitive | Blocked |
| BmrI | ACTGGG(5/4) | Not Sensitive | Not Sensitive | Not Sensitive |
| BmtI | GCTAG/C | Not Sensitive | Not Sensitive | Not Sensitive |
| BpmI | CTGGAG(16/14) | Not Sensitive | Not Sensitive | Not Sensitive |
| Bpu10I | CCTNAGC(-5/-2) | Not Sensitive | Not Sensitive | Not Sensitive |
| BpuEI | CTTGAG(16/14) | Not Sensitive | Not Sensitive | Not Sensitive |
| BsaAI | YAC/GTR | Not Sensitive | Not Sensitive | Blocked |
| BsaBI | GATNN/NNATC | Blocked by Overlapping Methylation | Not Sensitive | Blocked by Some Overlapping Combinations |
| BsaHI | GR/CGYC | Not Sensitive | Blocked by Some Overlapping Combinations | Blocked |
| BsaI | GGTCTC(1/5) | Not Sensitive | Blocked by Overlapping Methylation | Blocked by Some Overlapping Combinations |
| BsaI-HF™ | GGTCTC(1/5) | — | Blocked by Overlapping Methylation | — |
| BsaJI | C/CNNGG | Not Sensitive | Not Sensitive | Not Sensitive |
| BsaWI | W/CCGGW | Not Sensitive | Not Sensitive | Not Sensitive |
| BsaXI | (9/12)ACNNNNNCTCC(10/7) | Not Sensitive | Not Sensitive | Not Sensitive |
| BseRI | GAGGAG(10/8) | Not Sensitive | Not Sensitive | Not Sensitive |
| BseYI | CCCAGC(-5/-1) | Not Sensitive | Not Sensitive | Blocked by Overlapping Methylation |
| BsgI | GTGCAG(16/14) | Not Sensitive | Not Sensitive | Not Sensitive |
| BsiEI | CGRY/CG | Not Sensitive | Not Sensitive | Blocked |

| Enzyme | Sequence | Dam | Dcm | CpG |
| --- | --- | --- | --- | --- |
| BsiHKAI | GWGCW/C | Not Sensitive | Not Sensitive | Not Sensitive |
| BsiWI | C/GTACG | Not Sensitive | Not Sensitive | Blocked |
| BslI | CCNNNNN/NNGG | Not Sensitive | Blocked by Some Overlapping Combinations | Blocked by Some Overlapping Combinations |
| BsmAI | GTCTC(1/5) | Not Sensitive | Not Sensitive | Blocked by Some Overlapping Combinations |
| BsmBI | CGTCTC(1/5) | Not Sensitive | Not Sensitive | Blocked |
| BsmFI | GGGAC(10/14) | Not Sensitive | Blocked by Overlapping Methylation | Blocked by Overlapping Methylation |
| BsmI | GAATGC(1/-1) | Not Sensitive | Not Sensitive | Not Sensitive |
| BsoBI | C/YCGRG | Not Sensitive | Not Sensitive | Not Sensitive |
| Bsp1286I | GDGCH/C | Not Sensitive | Not Sensitive | Not Sensitive |
| BspCNI | CTCAG(9/7) | Not Sensitive | Not Sensitive | Not Sensitive |
| BspDI | AT/CGAT | Blocked by Overlapping Methylation | Not Sensitive | Blocked |
| BspEI | T/CCGGA | Blocked by Overlapping Methylation | Not Sensitive | Impaired |
| BspHI | T/CATGA | Blocked by Overlapping Methylation | Not Sensitive | Not Sensitive |
| BspMI | ACCTGC(4/8) | Not Sensitive | Not Sensitive | Not Sensitive |
| BspQI | GCTCTTC(1/4) | Not Sensitive | Not Sensitive | Not Sensitive |
| BsrBI | CCGCTC(-3/-3) | Not Sensitive | Not Sensitive | Blocked by Some Overlapping Combinations |
| BsrDI | GCAATG(2/0) | Not Sensitive | Not Sensitive | Not Sensitive |
| BsrFI | R/CCGGY | Not Sensitive | Not Sensitive | Blocked |
| BsrGI | T/GTACA | Not Sensitive | Not Sensitive | Not Sensitive |
| BsrI | ACTGG(1/-1) | Not Sensitive | Not Sensitive | Not Sensitive |
| BssHII | G/CGCGC | Not Sensitive | Not Sensitive | Blocked |
| BssKI | /CCNGG | Not Sensitive | Blocked by Overlapping Methylation | Blocked by Overlapping Methylation |
| BssSI | CACGAG(-5/-1) | Not Sensitive | Not Sensitive | Not Sensitive |
| BstAPI | GCANNNN/NTGC | Not Sensitive | Not Sensitive | Blocked by Some Overlapping Combinations |
| BstBI | TT/CGAA | Not Sensitive | Not Sensitive | Blocked |
| BstEII | G/GTNACC | Not Sensitive | Not Sensitive | Not Sensitive |
| BstNI | CC/WGG | Not Sensitive | Not Sensitive | Not Sensitive |

-continued

| Enzyme | Sequence | Dam | Dcm | CpG |
|---|---|---|---|---|
| BstUI | CG/CG | Not Sensitive | Not Sensitive | Blocked |
| BstXI | CCANNNNN/NTGG | Not Sensitive | Blocked by Some Overlapping Combinations | Not Sensitive |
| BstYI | R/GATCY | Not Sensitive | Not Sensitive | Not Sensitive |
| BstZ17I | GTA/TAC | Not Sensitive | Not Sensitive | Blocked by Some Overlapping Combinations |
| Bsu36I | CC/TNAGG | Not Sensitive | Not Sensitive | Not Sensitive |
| BtgI | C/CRYGG | Not Sensitive | Not Sensitive | Not Sensitive |
| BtgZI | GCGATG(10/14) | Not Sensitive | Not Sensitive | Impaired |
| BtsCI | GGATG(2/0) | Not Sensitive | Not Sensitive | Not Sensitive |
| BtsI | GCAGTG(2/0) | Not Sensitive | Not Sensitive | Not Sensitive |
| Cac8I | GCN/NGC | Not Sensitive | Not Sensitive | Blocked by Some Overlapping Combinations |
| ClaI | AT/CGAT | Blocked by Overlapping Methylation | Not Sensitive | Blocked |
| CspCI | (11/13)CAANNNNNGTGG(12/10) | Not Sensitive | Not Sensitive | Not Sensitive |
| CviAII | C/ATG | Not Sensitive | Not Sensitive | Not Sensitive |
| CviKI-1 | RG/CY | Not Sensitive | Not Sensitive | Not Sensitive |
| CviQI | G/TAC | Not Sensitive | Not Sensitive | Not Sensitive |
| DdeI | C/TNAG | Not Sensitive | Not Sensitive | Not Sensitive |
| DpnI | GA/TC | Not Sensitive | Not Sensitive | Blocked by Overlapping Methylation |
| DpnII | /GATC | Blocked | Not Sensitive | Not Sensitive |
| DraI | TTT/AAA | Not Sensitive | Not Sensitive | Not Sensitive |
| DraIII | CACNNN/GTG | Not Sensitive | Not Sensitive | Impaired by Overlapping Methylation |
| DrdI | GACNNNN/NNGTC | Not Sensitive | Not Sensitive | Blocked by Some Overlapping Combinations |
| EaeI | Y/GGCCR | Not Sensitive | Blocked by Overlapping Methylation | Blocked by Overlapping Methylation |
| EagI | C/GGCCG | Not Sensitive | Not Sensitive | Blocked |
| EagI-HF ™ | C/GGCCG | Not Sensitive | Not Sensitive | Blocked |
| EarI | CTCTTC(1/4) | Not Sensitive | Not Sensitive | Impaired by Overlapping Methylation |
| EciI | GGCGGA(11/9) | Not Sensitive | Not Sensitive | Blocked by Some Overlapping Combinations |

-continued

| Enzyme | Sequence | Dam | Dcm | CpG |
|---|---|---|---|---|
| Eco53kI | GAG/CTC | — | — | — |
| EcoNI | CCTNN/NNNAGG | Not Sensitive | Not Sensitive | Not Sensitive |
| EcoO109I | RG/GNCCY | Not Sensitive | Blocked by Overlapping Methylation | Not Sensitive |
| EcoP15I | CAGCAG(25/27) | Not Sensitive | Not Sensitive | Not Sensitive |
| EcoRI | G/AATTC | Not Sensitive | Not Sensitive | Blocked by Some Overlapping Combinations |
| EcoRI-HF ™ | G/AATTC | Not Sensitive | Not Sensitive | Blocked by Some Overlapping Combinations |
| EcoRV | GAT/ATC | Not Sensitive | Not Sensitive | Impaired by Some Overlapping Combinations |
| EcoRV-HF ™ | GAT/ATC | Not Sensitive | Not Sensitive | Impaired by Some Overlapping Combinations |
| FatI | /CATG | Not Sensitive | Not Sensitive | Not Sensitive |
| FauI | CCCGC(4/6) | Not Sensitive | Not Sensitive | Blocked |
| Fnu4HI | GC/NGC | Not Sensitive | Not Sensitive | Blocked by Overlapping Methylation |
| FokI | GGATG(9/13) | Not Sensitive | Impaired by Overlapping Methylation | Impaired by Overlapping Methylation |
| FseI | GGCCGG/CC | Not Sensitive | Impaired by Some Overlapping Combinations | Blocked |
| FspI | TGC/GCA | Not Sensitive | Not Sensitive | Blocked |
| HaeII | RGCGC/Y | Not Sensitive | Not Sensitive | Blocked |
| HaeIII | GG/CC | Not Sensitive | Not Sensitive | Not Sensitive |
| HgaI | GACGC(5/10) | Not Sensitive | Not Sensitive | Blocked |
| HhaI | GCG/C | Not Sensitive | Not Sensitive | Blocked |
| HincII | GTY/RAC | Not Sensitive | Not Sensitive | Blocked by Some Overlapping Combinations |
| HindIII | A/AG CTT | Not Sensitive | Not Sensitive | Not Sensitive |
| HinfI | G/ANTC | Not Sensitive | Not Sensitive | Blocked by Some Overlapping Combinations |
| HinP1I | G/CGC | Not Sensitive | Not Sensitive | Blocked |
| HpaI | GTT/AAC | Not Sensitive | Not Sensitive | Blocked by Some Overlapping Combinations |
| HpaII | C/CGG | Not Sensitive | Not Sensitive | Blocked |

-continued

| Enzyme | Sequence | Dam | Dcm | CpG |
| --- | --- | --- | --- | --- |
| HphI | GGTGA(8/7) | Blocked by Overlapping Methylation | Not Sensitive | Not Sensitive |
| Hpy166II | GTN/NAC | Not Sensitive | Not Sensitive | Blocked by Overlapping Methylation |
| Hpy188I | TCN/GA | Blocked by Overlapping Methylation | Not Sensitive | Not Sensitive |
| Hpy188III | TC/NNGA | Blocked by Overlapping Methylation | Not Sensitive | Blocked by Overlapping Methylation |
| Hpy99I | CGWCG/ | Not Sensitive | Not Sensitive | Blocked |
| HpyAV | CCTTC(6/5) | Not Sensitive | Not Sensitive | Impaired by Overlapping Methylation |
| HpyCH4III | ACN/GT | Not Sensitive | Not Sensitive | Not Sensitive |
| HpyCH4IV | A/CGT | Not Sensitive | Not Sensitive | Blocked |
| HpyCH4V | TG/CA | Not Sensitive | Not Sensitive | Not Sensitive |
| I-CeuI | CGTAACTATAACGGTCCTAAGGTAGCGAA(-9/-13) | — | — | — |
| I-SceI | TAGGGATAACAGGGTAAT(-9/-13) | — | — | — |
| KasI | G/GCGCC | Not Sensitive | Not Sensitive | Blocked |
| KpnI | GGTAC/C | Not Sensitive | Not Sensitive | Not Sensitive |
| KpnI-HF ™ | GGTAC/C | — | — | — |
| MboI | /GATC | Blocked | Not Sensitive | Impaired by Overlapping Methylation |
| MboII | GAAGA(8/7) | Blocked by Overlapping Methylation | Not Sensitive | Not Sensitive |
| MfeI | C/AATTG | Not Sensitive | Not Sensitive | Not Sensitive |
| MfeI-HF ™ | C/AATTG | Not Sensitive | Not Sensitive | Not Sensitive |
| MluI | A/CGCGT | Not Sensitive | Not Sensitive | Blocked |
| MlyI | GAGTC(5/5) | Not Sensitive | Not Sensitive | |
| MmeI | TCCRAC(20/18) | Not Sensitive | Not Sensitive | Blocked by Overlapping Methylation |
| MnlI | CCTC(7/6) | Not Sensitive | Not Sensitive | Not Sensitive |
| MscI | TGG/CCA | Not Sensitive | Blocked by Overlapping Methylation | Not Sensitive |
| MseI | T/TAA | Not Sensitive | Not Sensitive | Not Sensitive |
| MslI | CAYNN/NNRTG | Not Sensitive | Not Sensitive | Not Sensitive |
| MspA1I | CMG/CKG | Not Sensitive | Not Sensitive | Blocked by Overlapping Methylation |
| MspI | C/CGG | Not Sensitive | Not Sensitive | Not Sensitive |

-continued

| Enzyme | Sequence | Dam | Dcm | CpG |
| --- | --- | --- | --- | --- |
| MwoI | GCNNNNN/NNGC | Not Sensitive | Not Sensitive | Blocked by Some Overlapping Combinations |
| NaeI | GCC/GGC | Not Sensitive | Not Sensitive | Blocked |
| NarI | GG/CGCC | Not Sensitive | Not Sensitive | Blocked |
| Nb.BbvCI | CCTCAGC | Not Sensitive | Not Sensitive | Not Sensitive |
| Nb.BsmI | GAATGC | Not Sensitive | Not Sensitive | Not Sensitive |
| Nb.BsrDI | GCAATG | Not Sensitive | Not Sensitive | Not Sensitive |
| Nb.BtsI | GCAGTG | — | — | — |
| NciI | CC/SGG | Not Sensitive | Not Sensitive | Impaired by Overlapping Methylation |
| NcoI | C/CATGG | Not Sensitive | Not Sensitive | Not Sensitive |
| NcoI-HF ™ | C/CATGG | Not Sensitive | Not Sensitive | Not Sensitive |
| NdeI | CA/TATG | Not Sensitive | Not Sensitive | Not Sensitive |
| NgoMIV | G/CCGGC | Not Sensitive | Not Sensitive | Blocked |
| NheI | G/CTAGC | Not Sensitive | Not Sensitive | Blocked by Some Overlapping Combinations |
| NheI-HF ™ | G/CTAGC | Not Sensitive | Not Sensitive | Blocked by Some Overlapping Combinations |
| NlaIII | CATG/ | Not Sensitive | Not Sensitive | Not Sensitive |
| NlaIV | GGN/NCC | Not Sensitive | Blocked by Overlapping Methylation | Blocked by Overlapping Methylation |
| NmeAIII | GCCGAG(21/19) | Not Sensitive | Not Sensitive | Not Sensitive |
| NotI | GC/GGCCGC | Not Sensitive | Not Sensitive | Blocked |
| NotI-HF ™ | GC/GGCCGC | Not Sensitive | Not Sensitive | Blocked |
| NruI | TCG/CGA | Blocked by Overlapping Methylation | Not Sensitive | Blocked |
| NsiI | ATGCA/T | Not Sensitive | Not Sensitive | Not Sensitive |
| NspI | RCATG/Y | Not Sensitive | Not Sensitive | Not Sensitive |
| Nt.AlwI | GGATC(4/-5) | Blocked | Not Sensitive | Not Sensitive |
| Nt.BbvCI | CCTCAGC(-5/-7) | Not Sensitive | Not Sensitive | Blocked by Some Overlapping Combinations |
| Nt.BsmAI | GTCTC(1/-5) | Not Sensitive | Not Sensitive | Blocked |
| Nt.BspQI | GCTCTTC(1/-7) | Not Sensitive | Not Sensitive | Not Sensitive |
| Nt.BstNBI | GAGTC(4/-5) | Not Sensitive | Not Sensitive | Not Sensitive |
| Nt.CviPII | (0/-1)CCD | Not Sensitive | Not Sensitive | Blocked |
| PacI | TTAAT/TAA | Not Sensitive | Not Sensitive | Not Sensitive |

-continued

| Enzyme | Sequence | Dam | Dcm | CpG |
|---|---|---|---|---|
| PaeR7I | C/TCGAG | Not Sensitive | Not Sensitive | Blocked |
| PciI | A/CATGT | Not Sensitive | Not Sensitive | Not Sensitive |
| PflFI | GACN/NNGTC | Not Sensitive | Not Sensitive | Not Sensitive |
| PflMI | CCANNNN/NTGG | Not Sensitive | Blocked by Overlapping Methylation | Not Sensitive |
| PhoI | GG/CC | Not Sensitive | Impaired by Some Overlapping Combinations | Impaired by Some Overlapping Combinations |
| PI-PspI | TGGCAAACAGCTATTATGGGTATTATGGGT(-13/-17) | — | — | — |
| PI-SceI | ATCTATGTCGGGTGCGGAGAAAGAGGTAAT(-15/-19) | — | — | — |
| PleI | GAGTC(4/5) | Not Sensitive | Not Sensitive | Blocked by Some Overlapping Combinations |
| PmeI | GTTT/AAAC | Not Sensitive | Not Sensitive | Blocked by Some Overlapping Combinations |
| PmlI | CAC/GTG | Not Sensitive | Not Sensitive | Blocked |
| PpuMI | RG/GWCCY | Not Sensitive | Blocked by Overlapping Methylation | Not Sensitive |
| PshAI | GACNN/NNGTC | Not Sensitive | Not Sensitive | Blocked by Some Overlapping Combinations |
| PsiI | TTA/TAA | Not Sensitive | Not Sensitive | Not Sensitive |
| PspGI | /CCWGG | Not Sensitive | Blocked | Not Sensitive |
| PspOMI | G/GGCCC | Not Sensitive | Blocked by Overlapping Methylation | Blocked by Overlapping Methylation |
| PspXI | VC/TCGAGB | Not Sensitive | Not Sensitive | Impaired |
| PstI | CTGCA/G | Not Sensitive | Not Sensitive | Not Sensitive |
| PstI-HF™ | CTGCA/G | — | — | — |
| PvuI | CGAT/CG | Not Sensitive | Not Sensitive | Blocked |
| PvuII | CAG/CTG | Not Sensitive | Not Sensitive | Not Sensitive |
| PvuII-HF™ | CAG/CTG | Not Sensitive | Not Sensitive | Not Sensitive |
| RsaI | GT/AC | Not Sensitive | Not Sensitive | Blocked by Some Overlapping Combinations |
| RsrII | CG/GWCCG | Not Sensitive | Not Sensitive | Blocked |
| SacI | GAGCT/C | Not Sensitive | Not Sensitive | Not Sensitive |
| SacI-HF™ | GAGCT/C | Not Sensitive | Not Sensitive | Not Sensitive |
| SacII | CCGC/GG | Not Sensitive | Not Sensitive | Blocked |
| SalI | G/TCGAC | Not Sensitive | Not Sensitive | Blocked |
| SalI-HF™ | G/TCGAC | Not Sensitive | Not Sensitive | Blocked |

-continued

| Enzyme | Sequence | Dam | Dcm | CpG |
|---|---|---|---|---|
| SapI | GCTCTTC(1/4) | Not Sensitive | Not Sensitive | Not Sensitive |
| Sau3AI | /GATC | Not Sensitive | Not Sensitive | Blocked by Overlapping Methylation |
| Sau96I | G/GNCC | Not Sensitive | Blocked by Overlapping Methylation | Blocked by Overlapping Methylation |
| SbfI | CCTGCA/GG | Not Sensitive | Not Sensitive | Not Sensitive |
| SbfI-HF ™ | CCTGCA/GG | Not Sensitive | Not Sensitive | Not Sensitive |
| ScaI | AGT/ACT | Not Sensitive | Not Sensitive | Not Sensitive |
| ScaI-HF ™ | AGT/ACT | Not Sensitive | Not Sensitive | Not Sensitive |
| ScrFI | CC/NGG | Not Sensitive | Blocked by Overlapping Methylation | Blocked by Overlapping Methylation |
| SexAI | A/CCWGGT | Not Sensitive | Blocked | Not Sensitive |
| SfaNI | GCATC(5/9) | Not Sensitive | Not Sensitive | Impaired by Some Overlapping Combinations |
| SfcI | C/TRYAG | Not Sensitive | Not Sensitive | Not Sensitive |
| SfiI | GGCCNNNN/NGGCC | Not Sensitive | Impaired by Overlapping Methylation | Blocked by Some Overlapping Combinations |
| SfoI | GGC/GCC | Not Sensitive | Blocked by Some Overlapping Combinations | Blocked |
| SgrAI | CR/CCGGYG | Not Sensitive | Not Sensitive | Blocked |
| SmaI | CCC/GGG | Not Sensitive | Not Sensitive | Blocked |
| SmlI | C/TYRAG | Not Sensitive | Not Sensitive | Not Sensitive |
| SnaBI | TAC/GTA | Not Sensitive | Not Sensitive | Blocked |
| SpeI | A/CTAGT | Not Sensitive | Not Sensitive | Not Sensitive |
| SphI | GCATG/C | Not Sensitive | Not Sensitive | Not Sensitive |
| SphI-HF ™ | GCATG/C | Not Sensitive | Not Sensitive | Not Sensitive |
| SspI | AAT/ATT | Not Sensitive | Not Sensitive | Not Sensitive |
| SspI-HF ™ | AAT/ATT | Not Sensitive | Not Sensitive | Not Sensitive |
| StuI | AGG/CCT | Not Sensitive | Blocked by Overlapping Methylation | Not Sensitive |
| StyD4I | /CCNGG | Not Sensitive | Blocked by Overlapping Methylation | Impaired by Overlapping Methylation |
| StyI | C/CWWGG | Not Sensitive | Not Sensitive | Not Sensitive |
| StyI-HF ™ | C/CWWGG | — | — | — |
| SwaI | ATTT/AAAT | Not Sensitive | Not Sensitive | Not Sensitive |
| TaqαI | T/CGA | Blocked by Overlapping Methylation | Not Sensitive | Not Sensitive |

| Enzyme | Sequence | Dam | Dcm | CpG |
|---|---|---|---|---|
| TfiI | G/AWTC | Not Sensitive | Not Sensitive | Blocked by Some Overlapping Combinations |
| TliI | C/TCGAG | Not Sensitive | Not Sensitive | Impaired |
| TseI | G/CWGC | Not Sensitive | Not Sensitive | Blocked by Some Overlapping Combinations |
| Tsp45I | /GTSAC | Not Sensitive | Not Sensitive | Not Sensitive |
| Tsp509I | /AATT | Not Sensitive | Not Sensitive | Not Sensitive |
| TspMI | C/CCGGG | Not Sensitive | Not Sensitive | Blocked |
| TspRI | NNCASTGNN/ | Not Sensitive | Not Sensitive | Not Sensitive |
| Tth111I | GACN/NNGTC | Not Sensitive | Not Sensitive | Not Sensitive |
| XbaI | T/CTAGA | Blocked by Overlapping Methylation | Not Sensitive | Not Sensitive |
| XcmI | CCANNNNN/NNNNTGG | Not Sensitive | Not Sensitive | Not Sensitive |
| XhoI | C/TCGAG | Not Sensitive | Not Sensitive | Impaired |
| XmaI | C/CCGGG | Not Sensitive | Not Sensitive | Impaired |
| XmnI | GAANN/NNTTC | Not Sensitive | Not Sensitive | Not Sensitive |
| ZraI | GAC/GTC | Not Sensitive | Not Sensitive | Blocked |

C. Microarray Analysis

Microarray methods can be used in conjunction with the methods described herein for simultaneous testing of numerous genetic alterations of the human genome. The subject matter described herein can also be used in various fields to greatly improve the accuracy and reliability of nucleic acid analyses, chromosome mapping, and genetic testing. Selected chromosomal target elements can be included on the array and evaluated for 5mC and/or 5hmC content in conjunction with hybridization to a nucleic acid array. In an implementation that uses a diagnostic array (hereafter, "array"), such as a microarray used for comparative genomic hybridization (CGH), a comprehensive battery of clinically relevant chromosomal loci can be selected and evaluated for 5mC and/or 5hmC status or content. 5mC and/or 5hmC in genomic DNA fragments are specifically labeled using radio-labels, fluorescent labels or amplifiable signals. These labeled target DNA fragments are then screened by hybridization using microarrays.

D. FRET-based Hybridization Assay

A fluorescent tag can be attached to the 5mC and/or 5hmC and subsequently analyzed. A probe can be labeled with a first fluorescent tag and hybridized to a nucleotide labeled with a second fluorescent tag that functions as a FRET partner to the first. If the labeled based in the probe is juxtaposed with a labeled 5mC and/or 5hmC, a FRET signal will be observed.

E. Electrochemical Labeling

This method involves using AC impedance as a measurement for the presence of 5mC and/or 5hmC. Briefly, a nucleic acid probe specific for the sequence to be analyzed is immobilized on a gold electrode. The DNA fragment to be analyzed is added and allowed to hybridize to the probe. Excess non-hybridized, single-strand DNA is digested using nucleases. Biotin is covalently linked to the 5mC and/or 5hmC using the methods of the invention either before or after hybridization. Avidin-HRP is bound to the biotinylated DNA sequence then 4-chloronaphthol is added. If the HRP molecule is bound to the hybridized target DNA near the gold electrode, the HRP oxidizes the 4-chloronaphthol to a hydrophobic product that absorbs to the electrode surface. This results in a higher AC impedance if 5hmC is present in the target DNA compared to a control sequence lacking 5hmC.

F. Chromosomal Staining

Chromosomal DNA is prepared using standard karotyping techniques known in the art. The 5mC and/or 5hmC in the chromosomal DNA is labeled with a detectable moiety (fluorophore, radio-label, amplifiable signal) and imaged in the context of the intact chromosomes.

IV. Kits

The invention additionally provides kits for modifying cytosine bases of nucleic acids and/or subjecting such modified nucleic acids to further analysis. The contents of a kit can include one or more of a modification agent(s), a labeling reagent for detecting or modifying a 5mC and/or a 5hmC, and, if desired, a substrate that contains or is capable of attaching to one or more modified 5mC and/or 5hmC. The substrate can be, e.g., a microsphere, antibody, or other binding agent.

Each kit preferably includes a 5mC or 5hmC modifying agent or agents, e.g., TET, βGT, modification moiety, etc. One or more reagent is preferably supplied in a solid form or liquid buffer that is suitable for inventory storage, and later for addition into the reaction medium when the method of using the reagent is performed. Suitable packaging is provided. The kit may optionally provide additional components that are useful in the procedure. These optional components include buffers, capture reagents, developing reagents, labels, reacting surfaces, means for detection, control samples, instructions, and interpretive information.

Each kit may also include additional components that are useful for amplifying the nucleic acid, or sequencing the nucleic acid, or other applications of the present invention as described herein. The kit may optionally provide additional components that are useful in the procedure. These optional components include buffers, capture reagents, developing reagents, labels, reacting surfaces, means for detection, control samples, instructions, and interpretive information.

The kit may optionally include a detectable label or a modified glucose-binding agent and, if desired, reagents for detecting the binding agent.

V. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of certain embodiments, are provided as an example, and are not intended as limitations on the scope of the invention. Changes therein and other uses which are encompassed within the spirit of the invention as defined by the scope of the claims will occur to those skilled in the art.

EXAMPLE 1

Materials and Methods

Recombinant mTET1 expression and purification. The catalytic domain of Mouse TET1 (GU079948) gene was cloned into BssH1 and NotI sites of N-terminal Flag-tagged pFastBac Dual vector (Invitrogen) and expressed in Bac-to-Bac baculovirus insect cell expression system. The recombinant Flag-mTET1 (residues 1367-2039) was purified by using the published procedure (FIGS. 4a and 4b) (Ito et al., 2010).

Recombinant β-glucosyltransferase (β-GT) expression and purification. The Recombinant β-GT was expressed and purified by the protocol known in the art (Song et al., 2011).

Oligonucleotide synthesis. 9mer, 11mer, 32mer and 44mer oligonucleotides containing single CpG with modified cytosine (5mC or 5hmC) were prepared by incorporating the phosphoramidite (5mC and 5hmC) at the desired position during solid-phase synthesis (Dai and He, 2011). The reagents and phosphoramidites (5mC and 5hmC) were purchased from Glen Research. All synthetic oligonucleotides were further purified with denaturing polyacrylamide gel electrophoresis (Mishina and He, 2003). The oligonucleotides containing normal bases were purchased from Operon.

Synthesis of UDP-6-$N_3$-UDP. UDP-6-$N_3$-UDP is synthesized by using the protocol known in the art (Song et al., 2011).

Figures 4A, 4B, 4C:
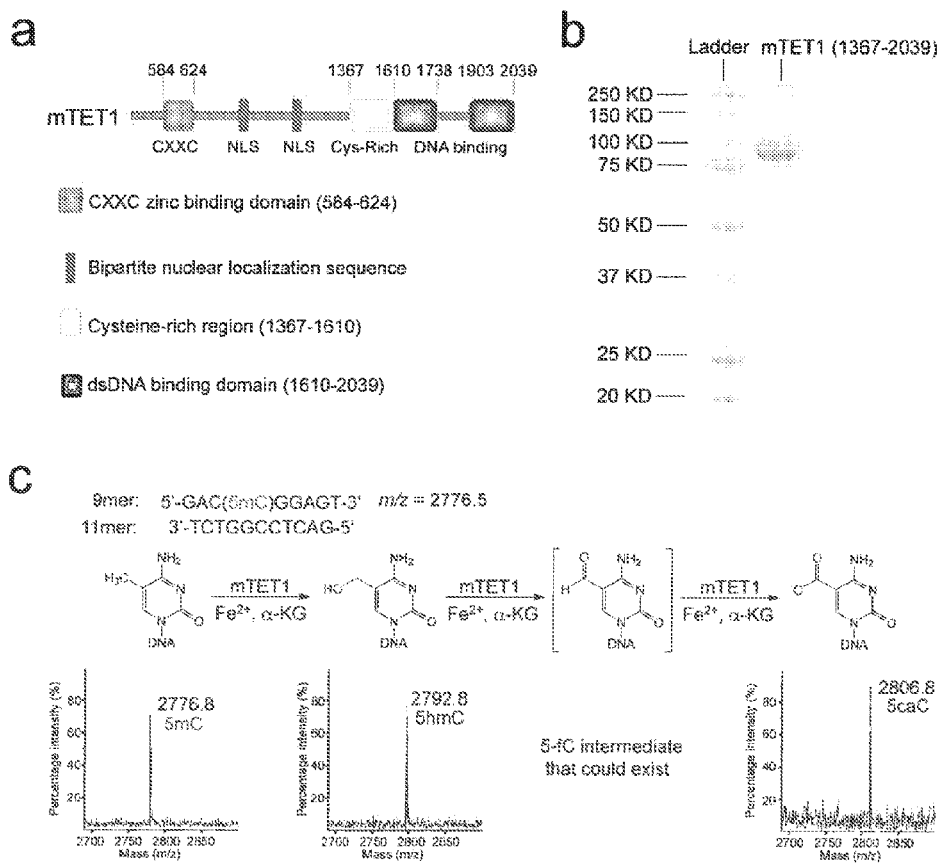
FIGS. 4A-4C Recombinant mTET1 protein (1367-2039) purification and activity test. (a) Schematic diagrams of mouse TET1 proteins. The major domains are shown as cubes as indicated. (b) Coomassie-stained SDS-PAGE gel containing purified recombinant Flag-mTET1 proteins that were purified from SF9 insect cells. (c) In vitro activity test of recombinant mTET1 protein by MALDI-TOF. The short model dsDNA sequence is also shown. The MALDI-TOF characterization on 9mer DNA is shown with the calculated and observed molecular weight indicated.

Recombinant mTET1 in vitro activity assay. Various concentration of recombinant mTET1 and 20 pmol 9mer-11mer dsDNA with internal 5-position methylated cytosine on 9mer DNA were added into the 20 µl reaction mixture containing 50 mM HEPES, pH8.0, 75 µM Fe(NH4)$_2$(SO$_4$)$_2$, 2 mM ascorbic acid, and 1 mM α-KG for 1 h at 37° C. The reaction products were then validated by MALDI-TOF (FIG. 4c).

Figures 5A, 5B, 5C:
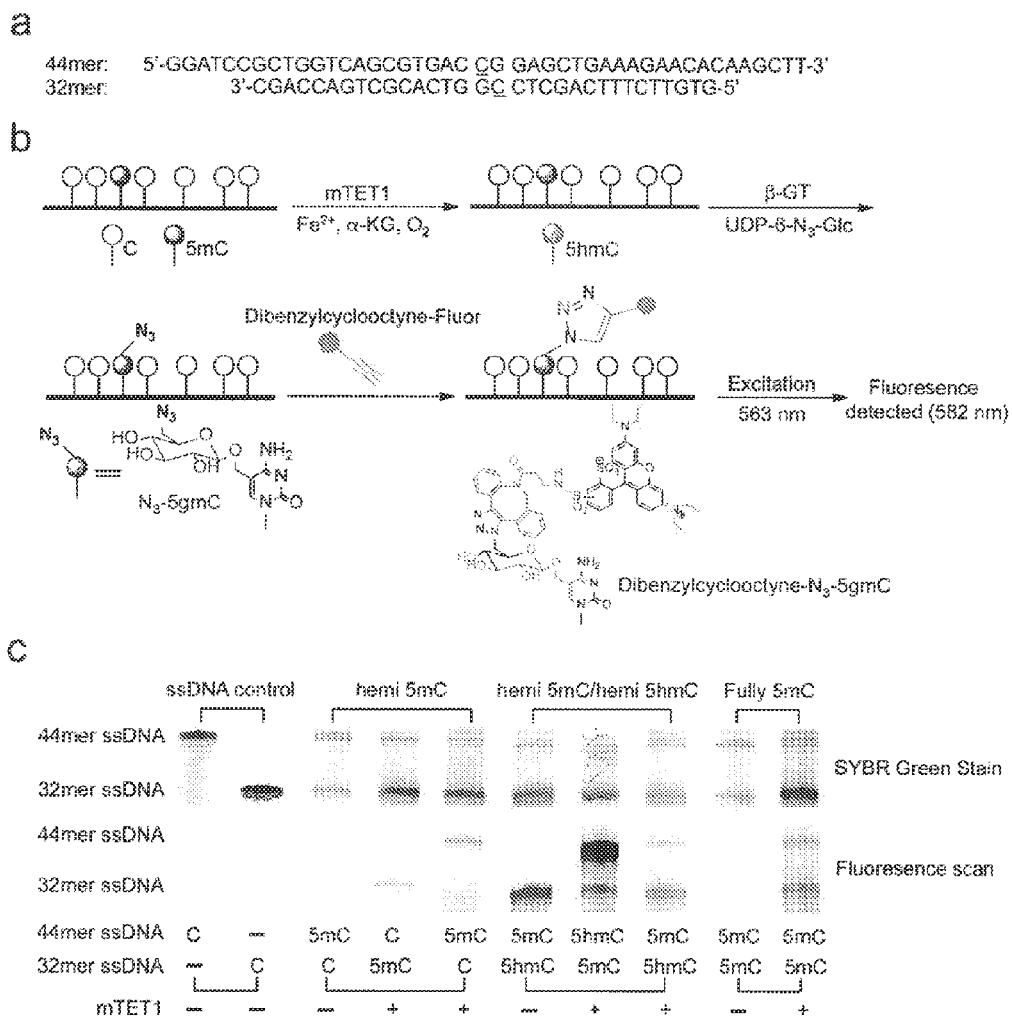
FIGS. 5A-5C Recombinant mTET1 substrate selectivity assay. (a) The sequences of 32mer-44mer dsDNA are shown. The underlined Cytosines indicate desired specific modification (C, 5mC or 5hmC) as shown in (c). (b) Schematic diagrams of the substrate selectivity assay. (c) The assay products were separated via 16% urea denatured acrylamide gels. The gel was first scanned under 563 nm and the fluorescence was detected at 582 nm. The gel was then stained with Syber Green.

Recombinant mTET1 substrate selectivity assay. 20 pmol recombinant mTET1, 40 pmol β-GT and 20 pmol 32mer-44mer dsDNA with desired modified cytosine (C, 5mC or 5hmC) were added into the 30 µl reaction mixture containing 50 mM HEPES, pH8.0, 75 µM Fe(NH4)$_2$(SO$_4$)$_2$, 2 mM ascorbic acid, 1 mM α-KG, 1 mM MgCl$_2$, 1 mM DTT and 100 UDP-6-$N_3$-Glucose for 1 h at 37° C. The DNA products were then purified by using Qiagen DNA purification kit, and subsequently mixed with 150 µM Dibenzylcyclooctyne-Fluor (Purchased from Click Chemistry Tools Bioconjugate Technology Company) for 2 h at 37° C. The labeled products were purified by the Qiagen purification kit again, and 200 ng were loaded to 16% Urea denatured acrylamide gels to separate the annealed strands. The gel was firstly scanned under 563 nm and the fluorescence is detected at 582 nm. The gel was then stained with Syber Green (FIG. 5).

Recombinant mTET1 and β-GT chemical labeling on genomic DNA (mESC and HCT116). 40 pmol β-GT recombinant protein and 3 µg sonicated genomic DNA (mESC J1 or HCT116 genomic DNA) were added into the 30 µl reaction mixture containing 50 mM HEPES, pH 8.0, 25 mM MgCl$_2$, and 300 µM UDP-Glucose for 1 h at 37° C. The product was purified by using Qiagen DNA purification kit. Subsequently, 160 pmol recombinant mTET1, 80 pmol β-GT protein and 2 µg treated genomic DNA were added into the 50 µl reaction mixture containing 50 mM HEPES, pH 8.0, 75 µM Fe(NH4)$_2$(SO$_4$)$_2$, 2 mM ascorbic acid, 1 mM α-KG, 1 mM MgCl$_2$, 1 mM DTT and 300 µM UDP-6-$N_3$-Glucose for 1 h at 37° C. The DNA product was then purified by using Qiagen DNA purification kit, and directly used in click reaction.

Huisgen cycloaddition (click) reaction and pull down. The click reaction and pull down was processed by following the protocol known in the art (Song et al., 2011).

TAmC-Seq library generation. 25 ng 5mC enriched DNA was end-repaired, adenylated, and ligated to methylated (5mC) adapters (Illumina Genomic DNA adapters) according to standard Illumina protocols for ChIP-Seq library construction. The proper molar ratios of adapter to insert was maintained. Adapter ligated fragments of ~200-350 bp were gel purified by 2% agarose gel electrophoresis and amplified by PCR for 18 cycles.

TAmC-Seq library sequencing. TAmC-Seq libraries were sequenced using the Illumina HiSscan platform. Cluster generation was performed with Illumina TruSeq cluster kit v2-cBot-HS. Single reads 51-bp sequencing was completed with Illumina TruSeq SBS kit v3-HS. A dedicated PhiX control lane, as well as 1% PhiX spike in all other lanes, was used for automated matrix and phasing calculations. Image analysis and base calling were performed with the standard Illumina pipeline.

Results

It has been newly discovered that 5mC could be oxidized by the iron(II)/αKG-dependent dioxygenases, TET family proteins (TET1, 2 and 3), to 5-hydroxymethylcytosine (5hmC), which can be further converted to 5-formylcytosine (5fC) and 5-carboxylcytosine (5caC) in genomic DNA of mammalian cells (He et al., 2011; Ito et al., 2011; Tahiliani et al., 2009; Ito et al., 2010; Pfaffeneder et al., 2011). Efficient chemical labeling methods were developed to selectively tag 5hmC with functional groups such as biotin for its robust affinity enrichment and sequencing without sequence and modification density bias (Song et al., 2011; Pastor et al., 2011). The inventors combined chemical labeling of 5hmC with TET-mediated conversion of 5mC to 5hmC for a selective labeling of 5mC for genome-wide detection and profiling.

In the strategy described herein, 5hmC is first protected with a glucose using T4 bacteriophage β-glucosyltransferase (β-GT)-mediated glucosylation of 5hmC (Song et al., 2011). The mouse TET1 catalytic domain (residues 1367-2039, named mTET1 hereinafter) is employed to oxidize 5mC to 5hmC, and the 5hmC that is newly generated by β-GT-mediated transfer of a modified glucose moiety (6-$N_3$-glucose) is simultaneously trapped to yield 6-$N_3$-β-glucosyl-5-hydroxymethyl-cytosine ($N_3$-5gmC) (Song et al., 2011). Utilizing Huisgen cycloaddition (click) chemistry, a biotin tag (or any chemical tag) is then installed to the azide group of $N_3$-5gmC for selective, efficient and unbiased pull-down of the original 5mC-containing DNA fragments for genome-wide profiling (FIG. 1) (Song et al., 2011). This new approach is named Tet-assisted 5-methylcytosine sequencing (TAmC-Seq).

Coupling Tet oxidation with β-glucosyltransferase for 5mC specific labeling. mTET1 was cloned, expressed, and purified using a baculovirus expression system according to the published procedure (Ito et al., 2010). The enzyme activity was confirmed with in vitro activity assays (FIG. 4) (Ito et al., 2011; Tahiliani et al., 2009; Ito et al., 2010; Pfaffeneder et al., 2011). As indicated in the previous studies, the overall conversion of 5mC to 5fC/5caC by mTET1 is not processive as the step of 5mC oxidation to 5hmC is kinetically faster than the subsequent 5hmC oxidation, which presents an opportunity to capture the newly generated 5hmC with an efficient β-GT-mediated labeling reaction (FIG. 1) (Song et al., 2011). It was further confirmed that mTET1 could recognize and oxidize 5mC from model double-stranded DNA (dsDNA) that contains hemi-5mC, fully-5mC or hemi-5mC/hemi-5hmC modification (FIG. 5), ensuring 5mC in various contexts could be efficiently labeled.

Figures 2A, 2B, 2C, 2D:
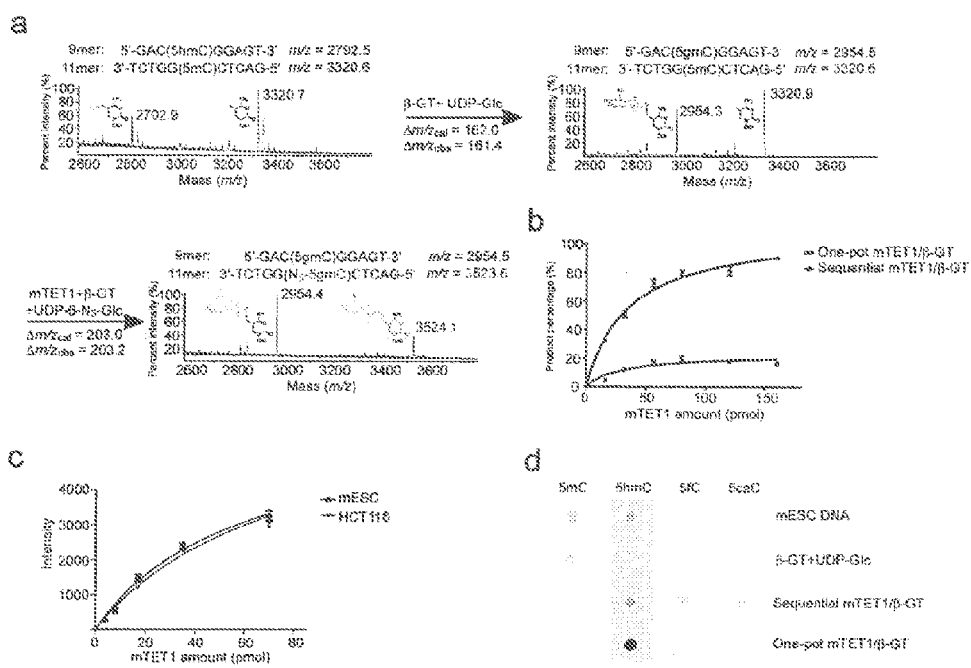
FIGS. 2A-2D The validation of the 5mC labeling using model dsDNA and genomic DNA. (a) MS characterization of the model reaction with a 5mC-containing 9mer DNA annealed to a 5hmC-containing 11mer DNA. The reactions were monitored by MALDI-TOF with the calculated molecular weight and observed molecular weight indicated. (b) The comparison of the 5mC conversion and labeling by using the one-pot mTET1/β-GT method and sequential mTET1/β-GT method. Various concentrations of recombinant mTET1 were used as indicated. The conversion ratio was evaluated by dot blot assay of the attached biotin. As shown in the figure, the one-pot mTET1/b-GT method labeled over 90% of 5mC in the model DNA. (c) 5mC labeling on genomic samples (mESC and HCT116) by using the one-pot mTET1/β-GT method. Various concentrations of recombinant mTET1 were used as indicated. 70-80 pmol mTET1 protein labeled most 5mC in 1 μg genomic DNA. (d) The labeled genomic DNA (mESC) products were validated by using antibodies against 5mC, 5fC and 5caC, respectively, and dot blot assay for 5hmC. The one-pot mTET1/b-GT method converted most 5mC to 5hmC for subsequent labeling with no over-oxidation products detected.

The inventors tested the new approach on a model dsDNA with a 5mC-containing 9mer oligonucleotide (5'-GAC(5hmC)GGAGT-3') annealed to a complementary 11mer oligonucleotide containing a 5hmC modification (3'-TCTGG(5mC)CTCAG)(FIG. 2a). In the first step, a regular glucose from uridinediphosphoglucose (UDP-Glc) was transferred to the 5hmC base by β-GT. The resulting β-glucosyl-5-hydroxymethyl-cytosine (5gmC) can no longer be oxidized or labeled as indicated by treating the dsDNA with mTET1 under oxidation conditions (FIG. 2a). mTET1 oxidation efficiently converts the 5mC on the opposite strand to 5hmC.

To avoid the potential over-oxidation of 5mC to 5fC and 5caC by mTET1, the inventors developed an one-pot procedure (referred to as one-pot mTET1/β-GT reaction). The 5hmC generated from oxidation of 5mC could be immediately captured and labeled with 6-$N_3$-glucose by β-GT-mediated glucosylation, which could effectively prevent over-oxidation of the newly generated 5hmC. The new $N_3$-5gmC is then labeled with biotin via click chemistry. As shown in FIG. 2b, ~90% hemi-5mC on the model dsDNA could be successfully labeled with biotin in the one-pot mTET1/β-GT reaction, whereas the sequential treatment of the same dsDNA with mTET1 and then β-GT only generated ~20% of the labeling. The click chemistry used in this system typically gives ~90% efficiency (Song et al., 2011), thus the one-pot mTET1/β-GT protocol affords a close to quantitative yield of labeling.

5mC specific labeling in genomic DNA The established method described herein were applied to label and profile genomic DNAs from mouse embryonic stem cell and human colon cancer HCT116 cell line. The candidate genomic DNA was sonicated into small fragments (~300-500 base pairs). After 5hmC being protected with glucose, an appropriate amount of mTET1 was added to mediate 5mC oxidation. Using the subsequenct one-pot mTET1/β-GT protocol, 70-80 pmol mTET1 converted and labeled most of 5mC to biotin in 1 genomic DNA with no over-oxidized products (5fC and 5caC) detected by western (FIG. 2c), whereas, the sequential mTET1/β-GT treatment led to noticeable amounts of 5fC and 5caC (FIG. 2d). It has also been confirmed that 5hmCs in genomic DNA were fully protected (FIG. 2d). The biotin-labeled genomic DNA samples were subsequently processed following the previously developed streptavidin pull-down method (Song et al., 2012).

Figure 6A:
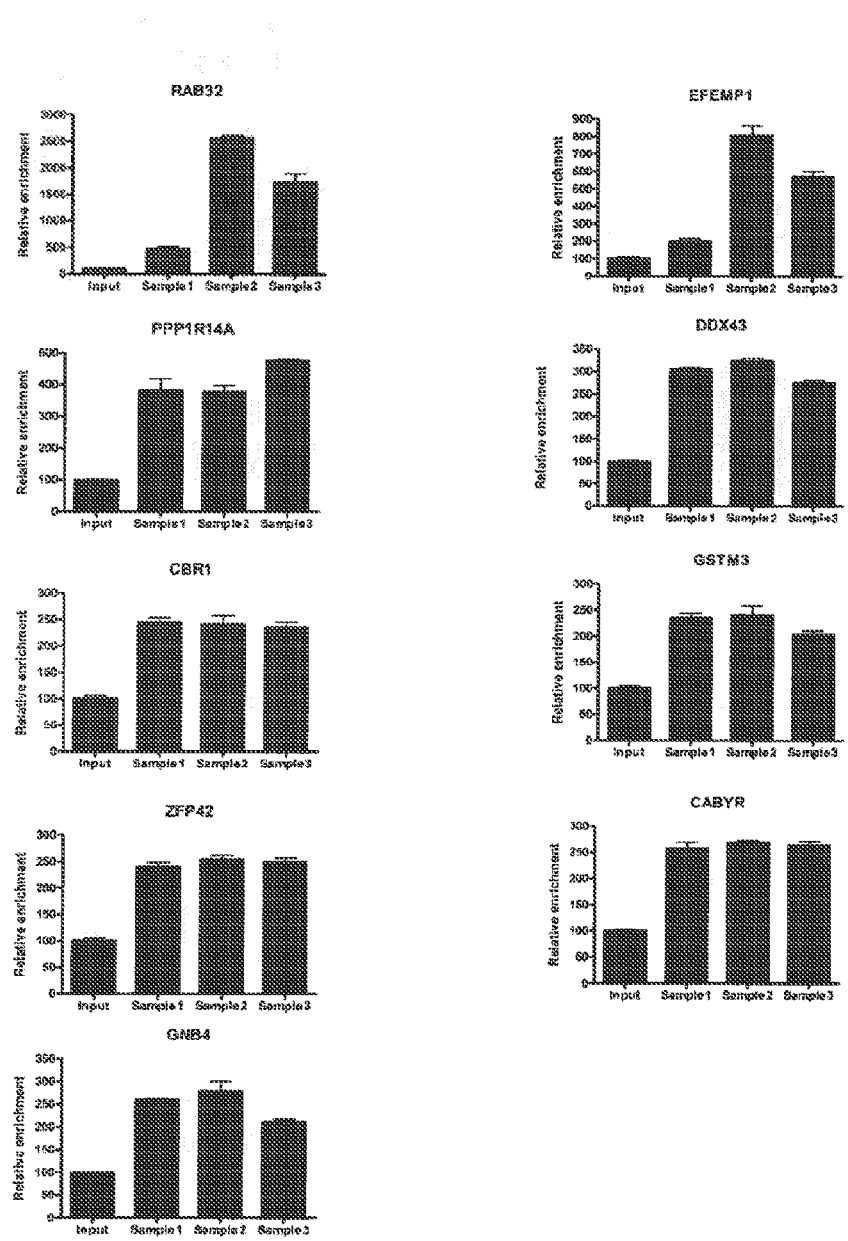
FIGS. 6A-6B Sensitivity and specificity of TAmC capture by qPCR. (a) 17 known methylated and 9 known non-methylated loci (Jones, P A and Baylin, S B, 2002) were assayed for 5mC enrichment by TAmC. 16 out 17 known methylated loci and 1 out of 9 known non-mehtylated loci exhibited 5mC enrichment. Enrichment is calibrated relative to non-enriched input genomic DNA, which is set to a value of 100. (b) Genomic snapshot of MeDIP-Seq, TAmC-Seq, 5hmC-Seq, and non-enriched Input genomic DNA read densities across the Pcdha locus (chr18:37,056,628-37,322, 944).

Specificity and sensitivity of 5mC enrichment at endogenous loci. The sensitivity and specificity of the approach were determined by applying it to assay enrichment of 5mC at known methylated and non-methylated regions. 5mC was captured and the enriched fragments were subjected to qPCR, measuring enrichment at 17 methylated loci and 9 non-methylated loci, as previously defined by multiple independent approaches (Schuebel et al., 2007), in 3 independent capture experiments from HCT116 colon cancers cells. The approach displayed 94.1% sensitivity, detecting 16 out of 17 known methylated regions, and 88.9% specificity, with only 1 out of 9 unmethylated loci exhibiting enrichment (FIG. 6A). These results demonstrated the general use of the method in correctly identifying methylated loci.

Application of TAmC-Seq genome-wide. Previous comparison of methods for mapping DNA methylation in human ES cells highlighted the advantage of MeDIP for capturing a relatively large number of CpGs genome-wide with relatively few reads, making it a cost effective approach despite the known biases associated with it (Harris et al., 2010). Having established TAmC-Seq as both sensitive and specific for 5mC on model DNA, as well as for known endogenously methylated loci, the inventors further assessed the utility of this new method in mapping 5mC genome-wide by appling it to J1 mouse embryonic stem (ES) cells. This experiment further allowed for direct comparison of TAmC-Seq with previously published MeDIP (Ficz et al., 2011), and quantitative assessment of 5mCs enriched by the two approaches.

Figures 3A, 3B, 3C, 3D, 3E:
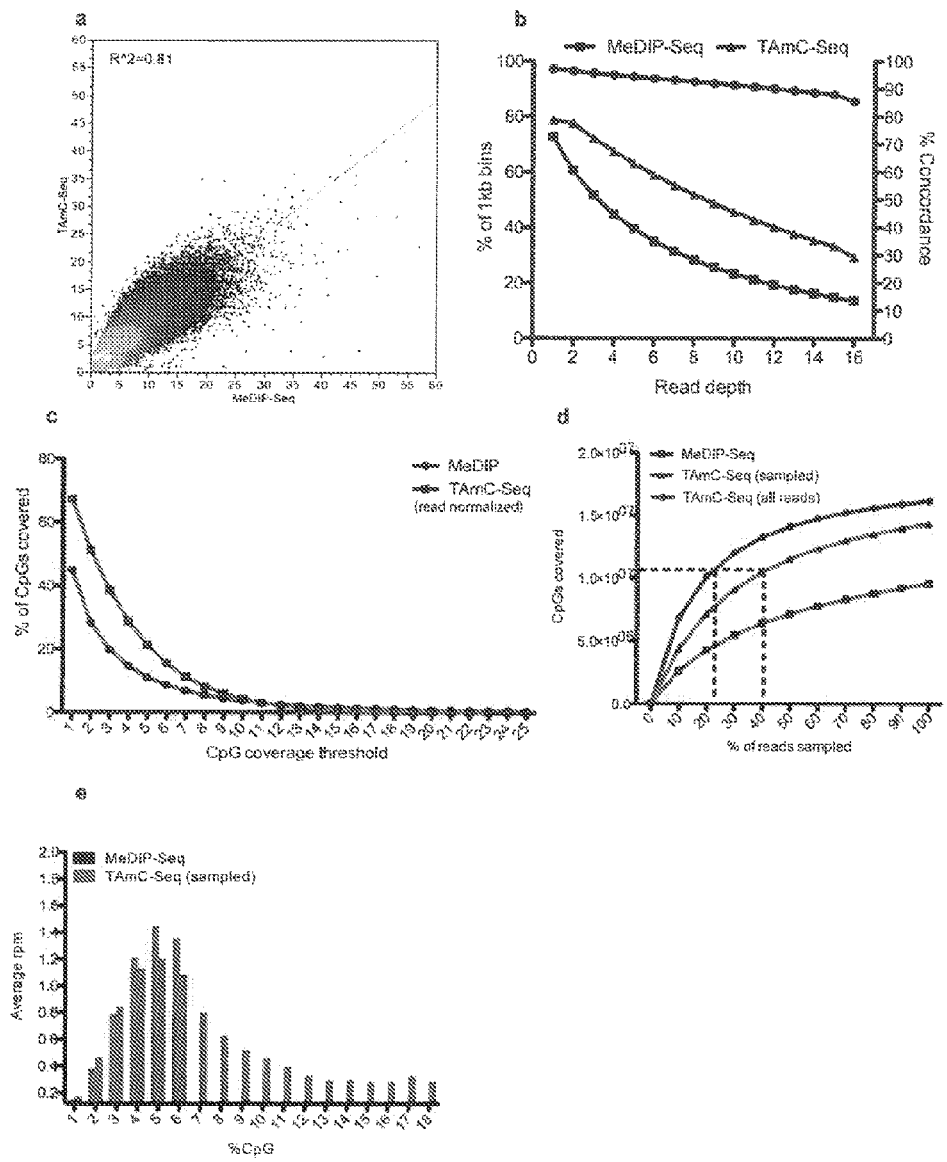
FIGS. 3A-3E Genome-wide Comparison of MeDIP and TAmC-Seq. (a) Genome-wide correlation between TAmC-Seq and MeDIP-Seq (10 kb bins, reads per million). (b) Concordance and genomic coverage of TAmC-Seq and MeDIP-Seq with varying read depth thresholds. Percent concordance shows the percentage of 1 kb bins with the given read depth threshold in MeDIP that agree with TAmC-Seq. (c) The fraction of CpGs covered genome wide as a function of the depth of coverage for TAmC-Seq and MeDIP-Seq. TAmC-Seq reads were randomly sampled to match the number of reads in MeDIP. (d) The number of CpGs covered genome wide by TAmC-Seq and MeDIP-Seq with varying fractions of reads used. TAmC-Seq The horizontal dotted line indicates 50% of all CpGs genome-wide. Vertical horizontal lines indiate the percentage of reads required to cover 50% of all CpGs ($K_{CpG-Seq}$) with all TAmC-Seq reads or TAmC-Seq reads randomly sampled to match the number of MeDIP-Seq reads. (e) The distribution of the average reads per million (rpm) derived from MeDIP-Seq or TAmC-Seq for 1 kb bins stratified by percent CpG content.
Figure 6B:
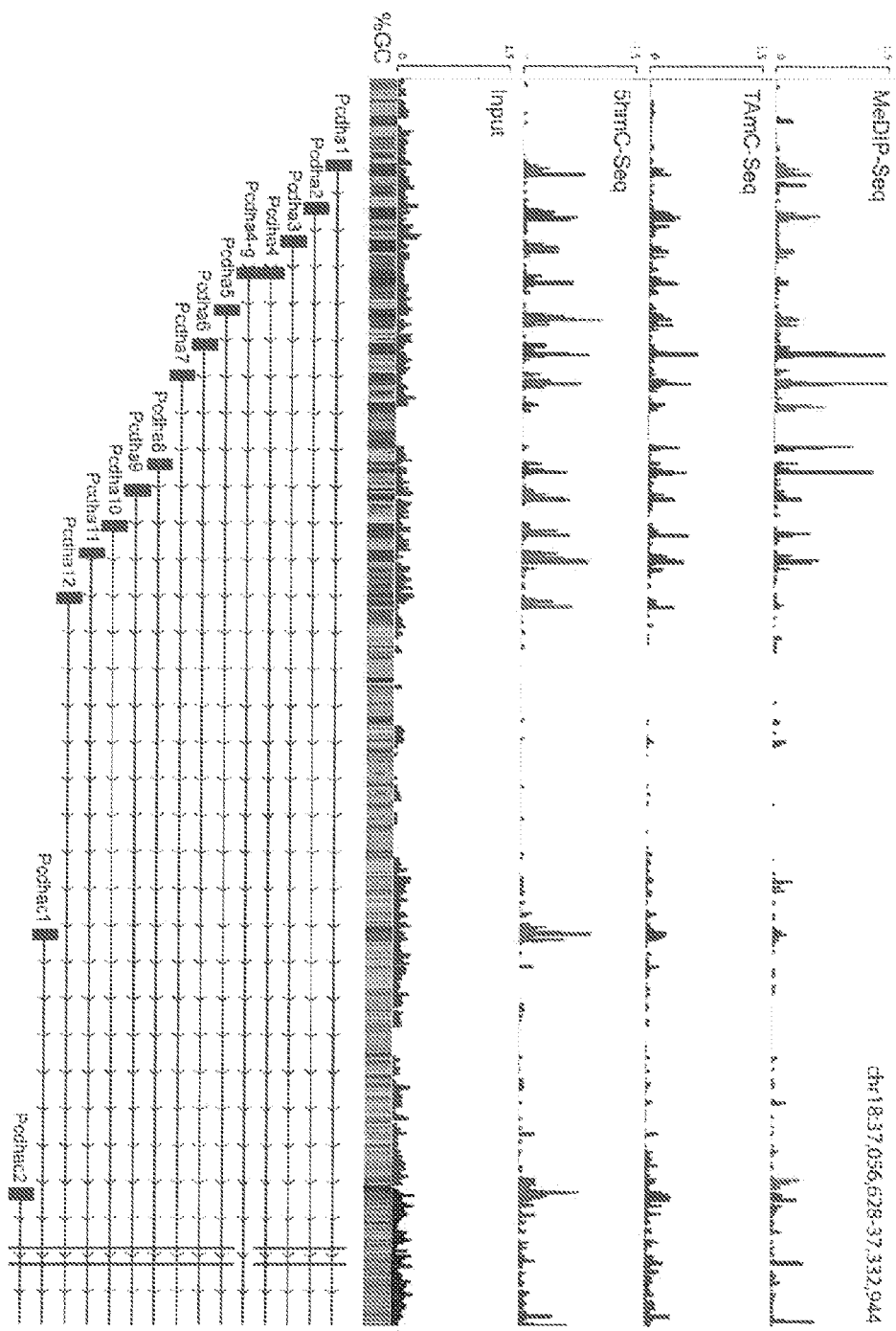

Read densities indicated that TAmC-seq provides a highly similar pattern of enrichment as compared to MeDIP. Indeed, normalized count data in genome-wide bins (10 kb) displayed a correlation coefficient of 0.81 ($R^2$) between TAmC-Seq and MeDIP-Seq (FIG. 3a). Likewise, read normalized binary calling of methylated regions with increasing read coverage thresholds showed that TAmC-Seq could account for >94% of the genomic space identified as methylated by MeDIP-Seq with a minimum read depth of five (FIG. 3b). However, TAmC-Seq generally exhibited more broad coverage than did MeDIP-Seq (FIG. 6B). This observation suggests that while specifically interrogating 5mC TAmC-Seq is able to capture a larger fraction of methylated CpGs with reduced density-related biases, resulting in an effective spreading of reads more evenly throughout methylated regions.

To quantify the comparative efficiency of capture by each approach, the inventors measured the number of CpG-dinucleotides covered genome-wide as a function of the number of reads sequenced. TAmC-Seq is capable of covering 22.4% more CpG dinucloetides than MeDIP-Seq, using an equivalent number of reads (FIG. 3c). When using the full set of TAmC-Seq reads, 76% percent of all CpGs were covered, approaching the estimated percentage of methylated cytosines observed in mouse embryonic stem cells (~80%) as determined by conventional bisulfite sequencing (Stadler et al., 2011). As an overall measure of efficiency the inventors next determined the number of reads required to cover 50% of all CpG dinucleotides, assuming that greater than this fraction are methylated in mouse ES cells (Stadler et al., 2011). TAmC-Seq achieved 50% coverage with 7.7×10⁶ reads (~41%) while MeDIP failed to achieve 50% coverage (FIG. 3c). These results indicate that TAmC-Seq is able to more effectively enrich methylated CpGs as compared to MeDIP and demonstrate the increased cost-efficiency of the approach for specifically interrogating cytosine methylation.

The primary downfall associated with current affinity-based 5mC enrichment procedures is that they often exhibit CpG density dependent biases, which can vary depending on antibody/protein source and the concentration of salts used during immunoprecipitation. To compare the relative biases associated with TAmC-Seq and MeDIP-Seq, the inventors stratified the genome into 1 kb bins based on CpG content and measured the frequencies of enriched reads from each approach. TAmC-Seq is able to capture a wider range of CpG content than is MeDIP, demonstrating the increased access TAmC-Seq provides into the methylome and the CpG-density related bias associated with MeDIP-Seq (FIG. 3d).

Figures 10A, 10B, 10C:
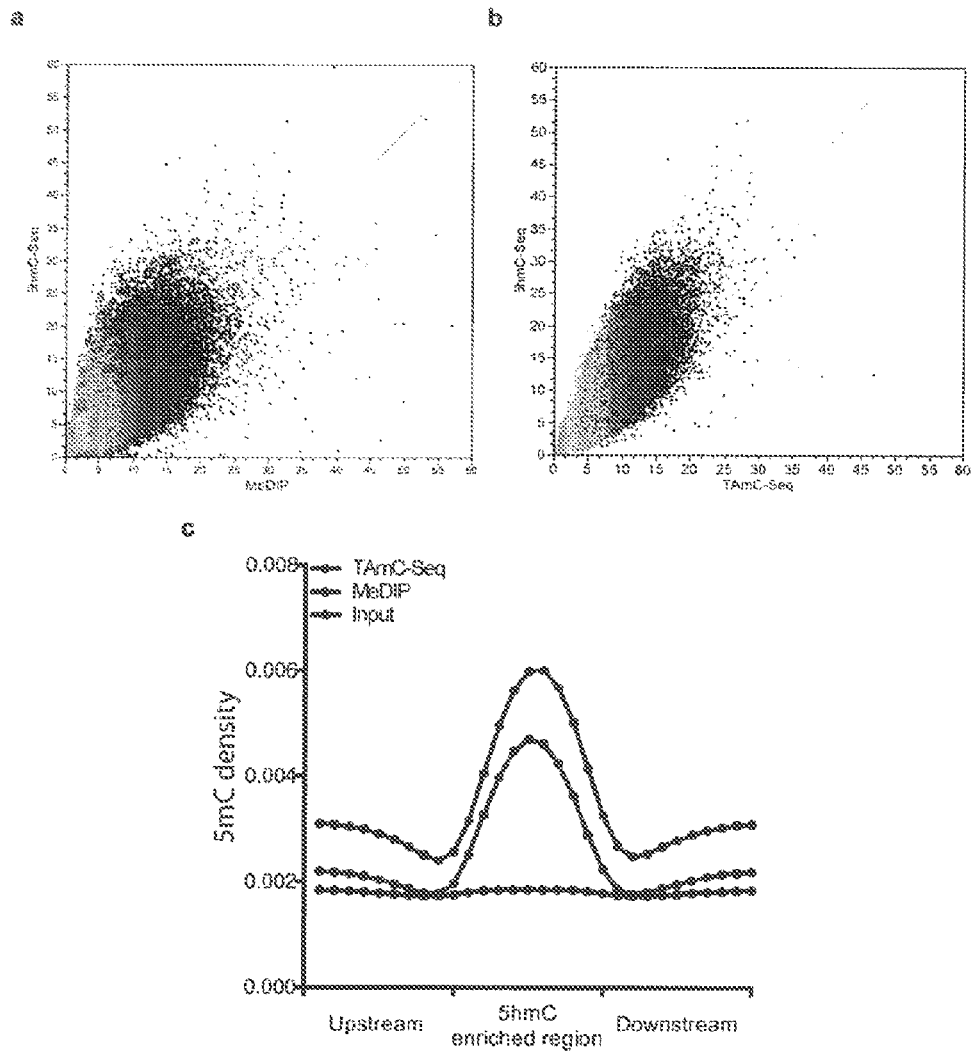
FIGS. 10A-10C Direct comparison of TAmC-Seq and MeDIP to 5hmC-Seq.

Direct comparison of TAmC-Seq and MeDIP to 5Hmc-Seq. The development of an improved approach for 5mC-specific capture might also be utilized to improve interpretation and comparison of 5mC to 5hmC. To explore this possibility, the inventors generated 5hmC specific profiles using the analogous capture technology that were previously developed, and subsequently compared them to profiles provided by MeDIP and TAmC-Seq. Consistent with the fact that 5hmC is derived from 5mC and previous reports demonstrating good genome-wide correlation between the two marks, it was observed relatively high correlation between 5mC and 5hmC, although to a different degree when comparing MeDIP and TAmC-seq 5mC profiles to one another (FIGS. 10a, b). However, TAmC-Seq provides an overall higher correlation between 5mC and 5hmC($R^2$=0.79) as compared to MeDIP-Seq ($R^2$=0.67). Likewise, after defining regions significantly enriched for 5hmC, TAmC-Seq yielded an increase in 5mC signal at 5hmC-enriched regions, above that produced by MeDIP-Seq. (FIG. 10c). These results indicate that previous antibody based maps of 5hmC can be improved upon through parallel application of a consistent enrichment procedure.

EXAMPLE 2

Figure 8A:
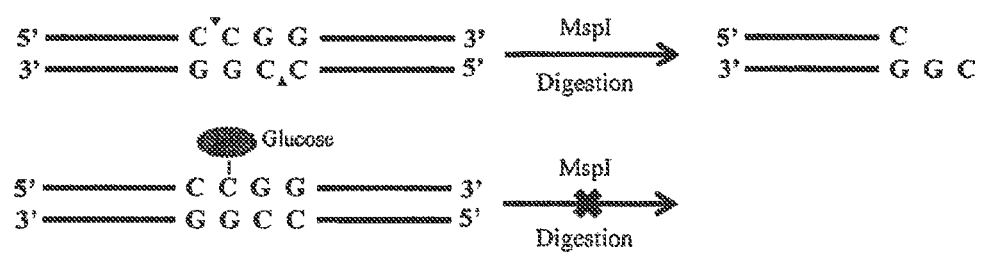
FIGS. 8A-8B Activity assay using TET1 and TET2 protein. Once the methyl group of cytosine is oxidized by TET and labeled with glucose, the MspI restrict enzyme cutting site is blocked by the glucose and the DNA cannot be digested. (a) Schematic diagram of MspI digestion. (b) TET1 and TET2 activity test. Lane 1, negative control; Lane 2, positive control; Lane 3-5, DNA is treated with 0.5, 1 and 3 μg TET1 before digestion; Lane 6, DNA is treated with 1 μg TET2 before digestion.
Figure 8B:
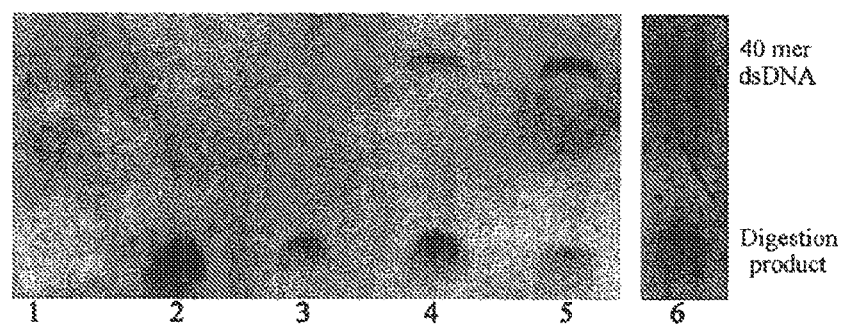
Figures 9A, 9B:
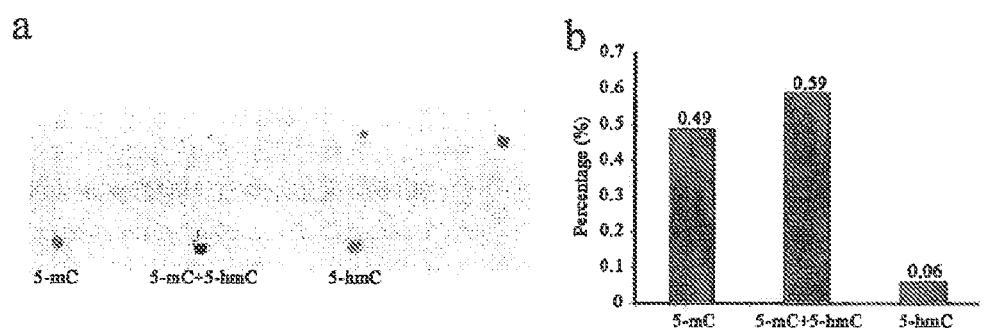
FIGS. 9A-9B Quantification of 5mC and 5hmC in mouse cerebellum genomic DNA. (a) Dot-blot assay of avidin-HRP detection and quantification of mouse cerebellum genomic DNA containing biotin-5-N3-gmC. Top row: 1-8 ng of 32 by synthetic biotin-$N_3$-ghmC-containing DNA as the standards. Bottom row: 43.5 ng mouse cerebellum genomic DNA sample (5-methylcytosine is oxidized by TET2 and labeled with biotin); 53.4 ng mouse cerebellum genomic DNA sample (the original 5-hydroxymethylcytosine and 5-methylcytosine are labeled with biotin); 448.6 ng mouse cerebellum genomic DNA sample (the original 5-hydroxymethylcytosine is labeled with biotin). (b) Amounts of 5mC and 5hmC in mouse cerebellum genomic DNA are shown in percentage of total nucleotides in the genome.

In the methods described herein, all TET family proteins (TET 1, 2, 3) could be employed to oxidize 5mC to 5hmC (FIG. 7). The inventors have demonstrated that the catalytic domains of mouse TET1 (1367-2039) and TET2 protein (916-1921) display high activity in converting 5mC to 5hmC (FIG. 8). Once 5mC is converted to 5hmC, it can be labeled with biotin, quantified by Dot-blot assay, enriched by biotin beads and sequenced or detected as described herein (FIG. 9). Initial results demonstrate that 5mC contributes 0.49% while 5hmC contributes 0.06% of total nucleotides of mouse cerebellum genomic DNA.

EXAMPLE 3

Materials and Methods

All the bisulfite conversion and purification of DNA was accomplished using the EpiTect Bisulfite Conversion Kit (Qiagen) in which 80 ng of substrate was used. The bisulfite-treated DNA was amplified by PCR and sent for sequencing.

The TET2 oxidative reaction was carried out by incubating 150 ng substrate with 5 µg TET2 (or TET1) in 50 mM HEPES, pH 8.0, 100 µM Fe(NH$_4$)$_2$(SO$_4$)$_2$.6H$_2$O, 1 mM α-KG, 2 mM ascorbic acid, 2.5 mM DTT, 1 mM ATP, 50 mM NaCl at 37° C. for 1.5 h.

The sequence of the 76mer 5caC-containing oligonucleotide (SEQ ID NO: 7)
5'-<u>CCTCACCATCTCAACCAATATTATATTATGTGTATAT</u>$^{ca}$CG$^{ca}$CGT ATTTTGTGTTATAATAT<u>TGAGGGAGAAGTGGTGA</u>-3'

The sequence of the 76mer 5mC-containing oligonucleotide, (SEQ ID NO: 8)
5'-<u>CCTCACCATCTCAACCAATATTATATTA</u>$^m$CG$^m$CGTATAT$^m$CG$^m$CGT ATTT$^m$CG$^m$CGTTATAATAT<u>TGAGGGAGAAGTGGTGA</u>-3'

Primer used for PCR after bisulfite treatment, (SEQ ID NO: 9)
Forward: 5'-CCC<u>TTTTATTATTTTAATTAATATTATATT</u>-3'

(SEQ ID NO: 10)
Reverse: 5'-<u>TCACCACTTCTCCCTCAAT</u>-3'

The sequence of 76mer oligonucleotide containing only one 5mC (SEQ ID NO: 11)
5'-<u>CCTCACCATCTCAACCAATATTATATTATGTGTATAT</u>$^m$CGATATTT TGTGTTATAATAT<u>TGAGGGAGAAGTGGTGA</u>-3'

Results

DNA epigenetic modifications such as 5-methylcytosine (5mC), the fifth base, play crucial roles in biological functions and various diseases. Recently, 5-hydroxymethylcytosine (5hmC) is discovered to be the sixth base in the mammalian genome and was widely accepted to be another player of epigenetic regulation and a potential disease marker. 5hmC and its natural creators, the TET dioxygenases, have received a tremendous amount of attention from the epigenetics and other related communities since its discovery. Currently, there are no single-base resolution sequencing method for 5hmC; the widely used bisulfite treatment-based sequencing is unable to differentiate 5mC from 5hmC (FIG. 11A).

To elucidate the exact biological roles of these two base modifications, the development of new analytical technologies, especially PCR-based single-base resolution sequencing methods for 5hmC has become essential. It has been discovered that TET proteins can over-oxidize 5mC and 5hmC to 5carboxylcytosine (5caC), and more importantly, 5caC behave the same as cytosine in bisulfite treatment. With these key findings as well as the inventors' previously developed method on selective labeling and detection/sequencing of 5hmC (Song et al., 2011), the inventors has developed a new strategy, termed oxidation-coupled bisulfite sequencing of 5hmC, to determine the specific sites of 5hmC in the genome at single-base resolution for research, clinical or other applications in an economic and efficient way.

Figures 11A, 11B:
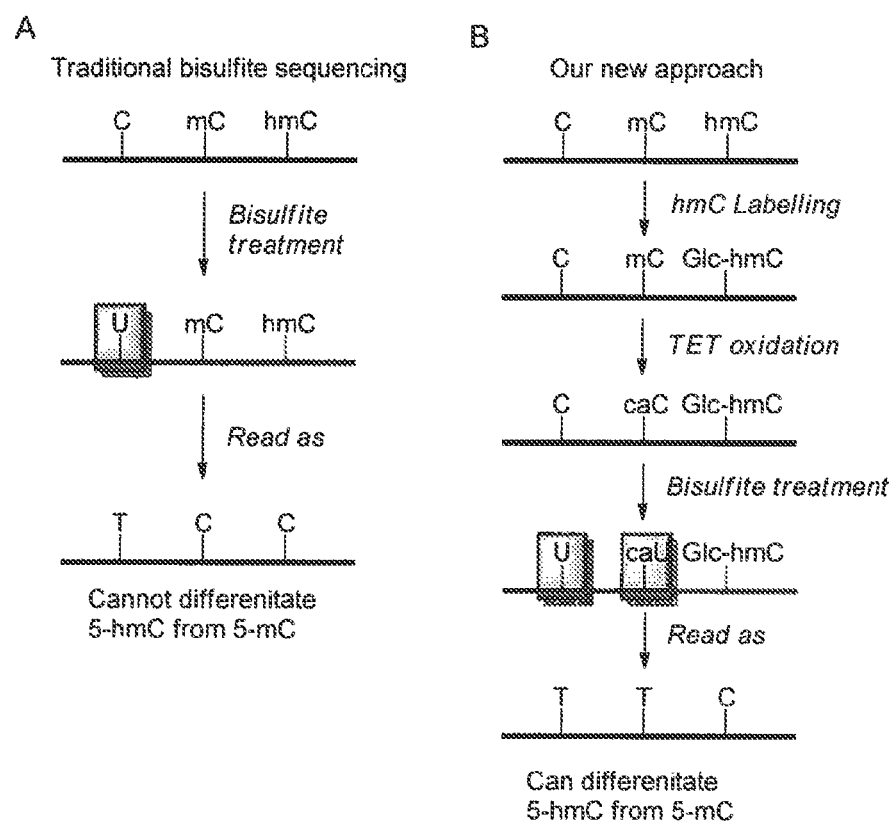
FIGS. 11A-11B FIG. 11A shows the flow chart of the traditional bisulfite sequencing, which cannot differentiate 5hmC from 5mC.

FIG. 11B demonstrates the new approach for single base-resolution 5hmC sequencing, which comprises following steps: 1. 5hmC in genomic DNA is labeled with a glucose or a modified glucose as developed by the inventors previously to protect it from TET oxidation; 2. 5mC in genomic DNA is oxidized to 5caC by mammalian methylcytosine dioxygenases (TET1, TET2 and TET3) or their homologues (including those improved by directed protein evolution) in other organisms; 3. Standard bisulfite treatment is employed, so that all the cytosines and 5caCs (the original 5mC) are deaminated, but the protected 5hmCs remain the same. After bisulfite treatment, cytosine and 5caC (from 5mC) will read as T in sequencing while 5hmC still reads as C, thus allowing single-base resolution detection of 5hmC by subsequent PCR-based sequencing.

Figure 12:
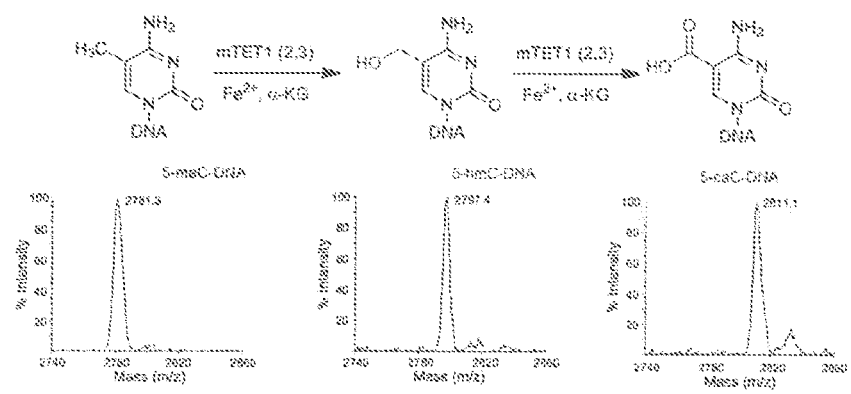
FIG. 12 Scheme of over oxidation of 5mC and 5hmC to 5caC by TET protein (top) and the corresponding MALDI-TOF of short DNA showing the high efficiency of conversion (bottom).

It has been shown that the catalytic domains of mouse TET1 (1367-2039) and human TET2 protein (916-1921) not only display high activity in converting 5mC to 5hmC, but they can also over oxidize 5mC and 5hmC to 5caC efficiently (FIG. 12). Once 5hmC is protected by glucose or modified glucose, it can no longer be oxidized. It has also been found that 5caC behaves like cytosine in bisulfite treatment, thus, 5hmC could be differeniated from 5mC by TET oxidation/bisufite treatment in this new approach.

Figure 13:
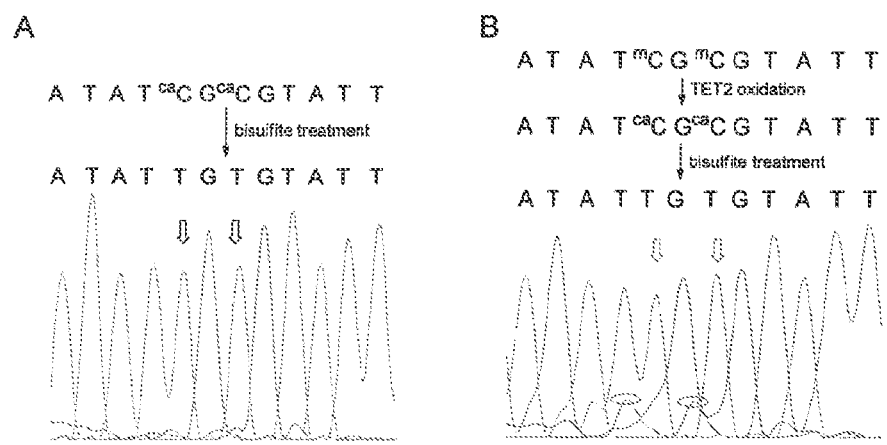
FIGS. 13A-13B Sequencing traces for standard bisulfite-treated 5caC and TET2-oxidized 5mC. (A) 5caC containing DNA was treated by standard bisulfite procedure. After purification and PCR amplification, the product was sent for sequencing. The 5caC bases behave as C under the standard bisulfite conditions. (B) 5mC-containing DNA was oxidized to 5caC by TET2 first and then treated by usinf standard bisulfite procedure. After purification and PCR amplification, the product was sent for sequencing. Most 5mC bases were converted to 5caC and read as T in the sequencing trace; circles indicate remaining 5mC that still read as C. Since protected 5hmC cannot be oxidized and will be read as C under standard bisulfite conditions the method can be used to differentiate 5hmC from 5mC. A sequence with two closely spaced 5mC was used. For less dense 5mC, even higher conversion efficiency is expected.

It has been confirmed that 5caC can be deaminated as readily as cytosine in standard bisulfite treatment (FIG. 13A). After TET-mediated over-oxidation, 5mC is converted to 5caC, which, upon bisulfite treatment, reads as T in close to 75% signal in sequencing in the inventor's model system (FIG. 13B).

Figure 14:
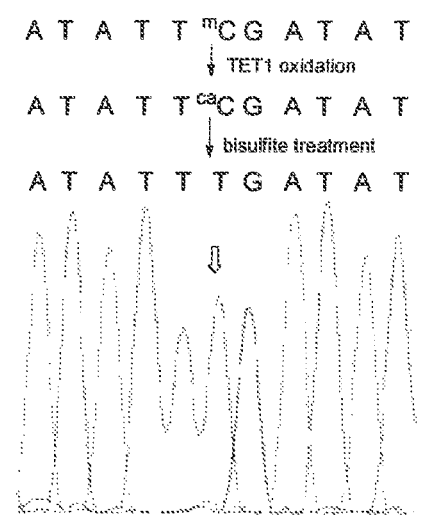
FIG. 14 Sequencing traces for a 76 mer DNA containing one 5mC after TET1-mediated oxidation of 5mC to 5caC. The TET1 oxidation reaction was carried out by incubating 150 ng substrate with 7 μg TET1 in 50 mM HEPES, pH 8.0, 100 μM Fe($NH_4$)$_2$($SO_4$)$_2$.6$H_2$O, 1 mM α-KG, 2 mM ascorbic acid, 2.5 mM DTT, 1 mM ATP, 100 mM NaCl at 37° C. for 1.5 h. After standard bisulfite treatment (60° C.) DNA sequencing indicates a complete conversion of the modified cytosine to T, indicating a complete conversion of 5mC to 5caC and that 5caC behave similarly to normal cytosine under standard bisulfite conditions.

FIG. 14 shows the sequencing traces for a 76 mer DNA containing one 5mC after TET2-mediated oxidation of 5mC to 5caC. It is demonstrated that after standard bisulfite treatment (60° C.), a complete conversion of the modified cytosine to T, indicating a complete conversion of 5mC to 5caC and that 5caC behave similarly to normal cytosine under standard bisulfite conditions.

EXAMPLE 4

Materials and Methods

Glucosylation and Oxidation of Genomic DNA. Glucosylation reactions were performed in a 50 µl solution containing 50 mM HEPES buffer (pH 8.0), 25 mM $MgCl_2$, 100 ng/µl sonicated genomic DNA with spiked-in control, 200 µM UDP-Glc, and 1 µM wild-type βGT. The reactions were incubated at 37° C. for 1 h. After the reaction, the DNA was purified by QIAquick Nucleotide Removal Kit (Qiagen). The oxidation reactions were performed in a 50 µl solution containing 50 mM HEPES buffer (pH 8.0), 100 µM ammonium iron (II) sulfate, 1 mM α-ketoglutarate, 2 mM ascorbic acid, 2.5 mM DTT, 100 mM NaCl, 1.2 mM ATP, 10 ng/µl glucosylated DNA and 3 µM recombinant mTet1. The reactions were incubated at 37° C. for 1.5 h. After proteinase K treatment, the DNA was purified with Micro Bio-Spin 30 Columns (Bio-Rad) first and then by QIAquick PCR Purification Kit (Qiagen)

Quantifying %5hmCG and %5mCG. For a given genomic interval, the abundance of hydroxymethylation (% hmCG) is estimated as the number of cytosine base calls in the interval divided by the number of cytosine plus thymine base calls in the interval from TAB-Seq reads, where the reference is in CG context. To estimate %5mC level, the total methylation level was substracted from methylC-Seq by the %5hmC level from TAB-Seq. In all instances, only base calls with Phred score ≥20 were considered.

Cell Culture. E14 (E14Tg2A) ES cell lines were cultured in feeder-free gelatin-coated plates in Dulbecco's Modified Eagle Medium (DMEM) (Invitrogen Cat. No. 11995) supplemented with 15% FBS (GIBCO), 2 mM L-glutamine (GIBCO), 0.1 mM 2-mercaptoethanol (Sigma), 1× non-essential amino acids (GIBCO), 1,000 units/ml LIF (Millipore Cat. No. ESG1107), 1× pen/strep (GIBCO), 3 µM CHIR99021 (Stemgent) and 1 µM PD0325901 (Stemgent). The culture was passaged every 2 days.

Expression and Purification of Recombinant mTET1. The catalytic domain (amino acids 1367-2039) of Mouse TET1 (GU079948) gene was cloned into BssH1 and NotI sites of N-terminal Flag-tagged pFastBac Dual vector (Invitrogen, cat:10712024) and then expressed in Bac-to-Bac baculovirus insect cell expression system. The recombinant protein was first purified with the anti-Flag M2 antibody agarose affinity gel (Sigma-Aldrich) as reported (Ito et al., 2010) and then loaded onto a Superdex 200 (GE Healthcare) gel-filtration column equilibrated with 20 mM HEPES (pH 8.0), 150 mM NaCl and 1 mM DTT.

Expression and Purification of β-Glucosyltransferase Protein (βGT). The βGT protein was expressed and purified following the previous protocol (Song et al., 2011).

Oligonucleotide Synthesis. 9-mer oligonucleotides containing modified cytosine (5mC or 5hmC) were prepared by using Applied Biosystems 392 DNA synthesizer with 5-Me-dC-CE or 5-hydroxymethyl-dC-CE phosphoramidite (Glen Research). All synthetic oligonucleotides were then purified by denaturing PAGE. The complementary 11-mer oligonucleotide without modified bases was purchased from Operon. 11-mer and 13-mer 5hmC containing oligonucleotides for HPLC analysis were prepared in the same way.

Figures 15A, 15B, 15C, 15D:
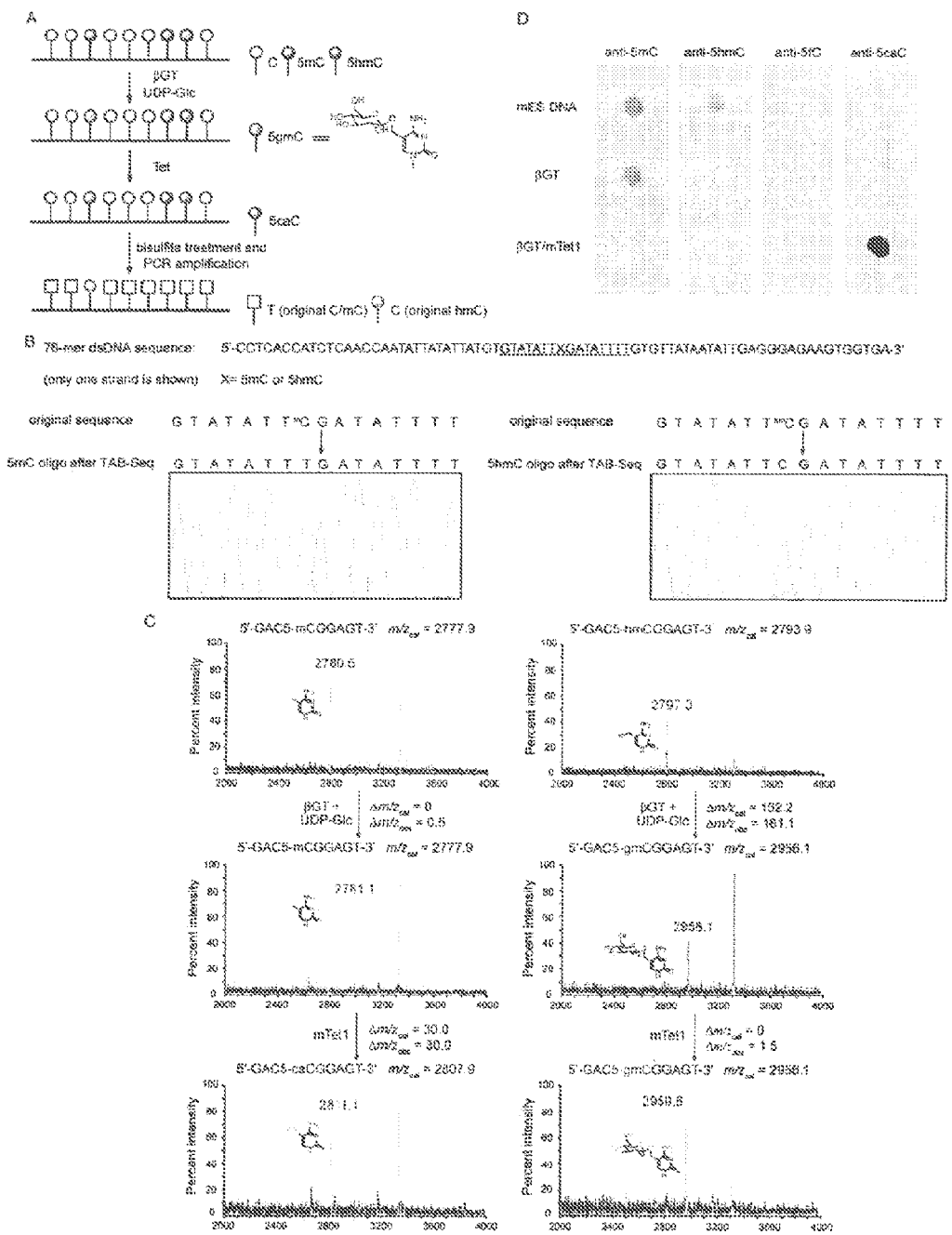
FIGS. 15A-15D. TAB-Seq Strategy and Validation. (A) Single-base resolution sequencing strategy for 5hmC (TAB-Seq). The 5hmCs (blue circles) in genomic DNA are protected by glucosylation (green circles), and then 5mCs (black circles) are converted to 5caCs (purple circles) by Tet-mediated oxidation. After bisulfite treatment, both 5mC and C (white circles) display as T (white squares) while 5gmC (generated from original 5hmC) displays as C (pink circle). (B) TAB-Seq of 76-mer dsDNA with 5mC or 5hmC. The 76-mer dsDNA with 5mC (left) or 5hmC (right) modification was subject to TAB-Seq as described in FIG. 15A. Sanger sequencing results showed that 5mC was completely converted to T (left) and 5hmC still read as C (right). (C) Mass spectrometry characterization of the products from TAB-Seq with a model dsDNA. The dsDNA contains a 5mC (left) or 5hmC (right) on a 9mer strand annealed to a 11mer complementary strand. The DNA was subject to βGT-mediated glucosylation and mTet1-mediated oxidation. The reactions were monitored by MALDI-TOF/TOF with the calculated and observed molecular weight indicated. (D) Validation of 5mC and 5hmC conversion in genomic DNA (mouse ES) with western blotting. The untreated genomic DNA, βGT-treated genomic DNA, and βGT/mTet1-treated genomic DNA were tested with dot blot assays using antibodies against 5mC, 5hmC, 5fC and 5caC, respectively. No 5hmC could be observed after βGT-mediated glucosylation. Almost all 5mCs were converted into 5caC after the mTet1-mediated oxidation based on the assay.

Preparation of 76-mer Double-Stranded DNA with 5mC or 5hmC Modification. The 76-mer dsDNA with one 5mC or 5hmC on one strand (as shown in FIG. 15B) were generated using PCR reaction with 5-methyl-2'-deoxycytidine 5'-triphosphate (5mdCTP) (Fermentas) or 5-hydroxymethyl-2'-deoxycytidine 5'-triphosphate (5hmdCTP) (Bioline) in place of dCTP and RED Taq polymerase (Sigma-Aldrich). To remove the unmodified template from product, two rounds of PCR were applied with 22 cycles in the first round and 30 cycles in the second round as described (Jin et al., 2010). The PCR products were then purified using PCR purification kits (Qiagen) (Forward primer: 5'-CCTCAC-CATCTCAACCAATA-3' (SEQ ID NO:12); Reverse primer: 5'-TCACCACTTCTCCCTCAAT-3' (SEQ ID NO:10)).

TAB-Seq of 76-mer dsDNA. The glucosylation reactions were performed in a 20 µl solution containing 50 mM HEPES buffer (pH 8.0), 25 mM $MgCl_2$, 100 ng/µl model DNA, 200 µM UDP-Glc, and 1 µM βGT. The reactions were incubated at 37° C. for 1 h. After the reaction, the DNA was purified by QIAquick Nucleotide Removal Kit (Qiagen). The oxidation reactions were performed in a 20 µl solution containing 50 mM HEPES buffer (pH 8.0), 100 µM ammonium iron (II) sulfate, 1 mM α-ketoglutarate, 2 mM ascorbic acid, 2.5 mM DTT, 100 mM NaCl, 1.2 mM ATP, 15 ng/µl glucosylated DNA and 3 µM recombinant mTet1. The reactions were incubated at 37° C. for 1.5 h. After proteinase K treatment, the DNA was purified with QIAquick Nucleotide Removal Kit (Qiagen) and then applied to EpiTect Bisulfite Kit (Qiagen) following the supplier's instruction. After PCR amplification with Hotstar Taq polymerase (Qiagen) (Forward primer: 5'-CCCTTT TATTATTTTAATTAAT-ATTATATT-3' (SEQ ID NO:13); Reverse primer: 5'-CTC-CGACATTATCACTACCATCAACCACCCATCCTACCT GGACTACATTCTTATTC AGTATTCACCACTTCTC-CCTCAAT-3' (SEQ ID NO:14)), the PCR product was purified using PCR purification kits (Qiagen) and sent for sequencing.

HPLC Analysis of βGT Catalyzed Glucosylation. The glucosylation reactions were performed in a 120 μl solution containing 50 mM HEPES buffer (pH 8.0), 25 mM MgCl$_2$, 10 μM fully-hydroxymethylated dsDNA, 200 μM UDP-Glc, and 1 μM βGT. The reactions were incubated at 37° C. for 1 h. After the reaction, both the substrate DNA (1.2 nmol) and glucosylated DNA were digested by two unit Nuclease P1 (Sigma) in 0.01 M NH$_4$Ac (pH 5.3) at 45° C. for 2 h and then two unit of Alkaline Phosphatase (Sigma) in 0.1 M fresh NH$_4$HCO$_3$ at 37° C. overnight. The digested DNA was analyzed by HPLC with a C18 reverse-phase column equilibrated with buffer A (50 mM ammonium acetate) and buffer B (50 mM ammonium acetate, 0.1% TFA, 60% CH$_3$CN).

Dot Blot Assay. βGT-treated and βGT/mTet1-treated mouse ES genomic DNA was generated as described above. 2 μg of DNA was denatured in 0.4 M NaOH, 10 mM EDTA at 95° C. for 10 min, and then neutralized by adding an equal volume of cold 2 M ammonium acetate (pH 7.0). 150 ng denatured DNA samples were spotted on nitrocellulose membrane (GE Healthcare). The membrane was then blocked with 5% non-fat milk and incubated with 5mC antibody (1:500) (Epigentek), 5hmC antibody (1:10000) (Active Motif), 5fC antibody (1:5000) (Active Motif) or 5caC antibody (1:2000) (Active Motif). Binding of an HRP-conjugated secondary antibody (1:1000) was visualized by enhanced chemiluminescence.

Semiconductor Sequencing. E14Tg2a genomic DNA was spiked with 0.5% M.SssI treated DNA and subjected to TAB-Seq treatment as described above or used directly in sodium bisulfite conversion. After MethylCode bisulfite conversion of 50 ng, 1 pL of converted DNA was PCR amplified as follows in a 50 pL final reaction volume: 2.5U PfuTurbo Cx Hotstart DNA polymerase, 5 μL 10× PfuTurbo Cx reaction buffer, 1 pL 10 mM dNTPs, 1 μL 10 μM FW primer (5'-CCATCTCATCCCTGCGTGT CTCCGACTCA-GAATTTGGTGGTGAGTAATGGTTTTA (SEQ ID NO:15)), 1 μL, 10 pM RV primer (5'-CCTCTC-TATGGGCAGTCGGTGATAACCTACCCCAACACCT-ATTTAAAT (SEQ ID NO:16)). Cycling parameters: 95° C. 2 min, 35 cycles of 95° C. 30 sec, 55° C. 30 sec, 72° C. 1 min, followed by 72° C. 5 min. Fusion PCR primers were designed to incorporate sequences at their 5' ends that are compatible with Ion Torrent template generation. PCR products were purified on Qiagen MinElute columns and quantified on an Agilent 2100 Bioanalyzer High Sensitivity DNA Chip. Sequencing template was generated using and Ion Torrent OneTouch System and Ion OneTouch System Template Kits (Life Technologies). Sequencing reactions were performed for 100 cycles on an Ion PGM semiconductor instrument using an Ion 314 chip and Ion Sequencing Kit (Life Technologies). Sequences were aligned to an index built from only the targeted amplicon using Bowtie in an analogous way to that used for genome-wide sequencing, except without preprocessing reads and requiring full-length perfect matches. Validation of TAB-Seq calls was done in the same manner using an independent mTet1 oxidation of H1 genomic DNA and testing two separate loci that were not previously identified as enriched with 5hmC (Szulwach et al., 2011). These loci included a total of 57 cytosines (11 CpG dincleotides) and 9 same strand 5hmC calls. The hg18 genomic coordinates for the amplicons were chr4:182,423, 188-182,423,312 and chr11:45,723,245-45,723,393. The corresponding fusion primer sequences, respectively, were (FW-5'-CCATCTCATCCCTGCGTGTCTCCGACTCAG-TAGAAGTAAA GGAAGTAAAGGAAGTATG (SEQ ID NO:17); RV-5'-CCTCTCTATGGGCAGTCGGTGA-TAAACCTAAAT AATAACAAACACACC (SEQ ID NO:18)) and (FW-5'-CCATCTCATCCCTGCGTGTCTC-CGACTCAG GAAGTTGTATAAAATTTTTGGATGTG (SEQ ID NO:19); RV-5'-CCTCTCTATGGGCAGTCGGT-GAT CCTCTCCTATCTCCCTTAACTACTC (SEQ ID NO:20))

TAB-Seq of Specific Loci in Mouse Cerebellum. 500 ng-1 μg untreated or βGT/mTet1-treated (the same procedure as mouse ES/H1 cell) mouse cerebellum sample was applied to EpiTect Bisulfite Kit (Qiagen) following the supplier's instruction. After PCR amplification with RED Taq polymerase (Sigma-Aldrich) or Hotstar Taq polymerase (Qiagen) (for 5hmC site, Forward primer: 5'-TTTGATTTTTGT-GTTTAGTAGTT TTGTG-3' (SEQ ID NO:21); Reverse primer: 5'-CCTCCTCAATTTTAAAATCTATTCC-3' (SEQ ID NO:22); for 5mC site, Forward primer: 5'-TTTAGGAAT-TGATAGGTAGTTGTAG-3' (SEQ ID NO:23); Reverse primer: 5'-AAACACAAACAATCTTACAAAAAAAAA-3' (SEQ ID NO:24)), the PCR product was purified using PCR purification kits (Qiagen) and sent for sequencing.

Generation of 5mC Spike in Conversion Controls for Mouse ES Cells. For the E14Tg2a mouse ES samples, unmethylated Lambda c1857 DNA (Promega) was treated with M.SssI to fully-methylate all CpG cytosines. CpG methylation was confirmed by spiking M.SssI treated Lambda DNA into genomic DNA at 0.5% followed by standard bisulfite conversion, PCR amplification, TOPO cloning, and Sanger sequencing. After MethylCode bisulfite conversion of 50 ng, 1 μL of converted DNA was PCR amplified as follows in a 50 μL final reaction volume: 2.5U PfuTurbo Cx Hotstart DNA polymerase, 5 μL 10× PfuTurbo Cx reaction buffer, 1 μL 10 mM dNTPs, 1 μL 10 μM FW primer (5'-TTTGGGTTATGTAAGTTGATTTTATG (SEQ ID NO:25)), 1 μL 10 μM RV primer (5'-CACCCTACT-TACTAAAATTTACACC (SEQ ID NO:26)). Cycling parameters: 95° C. 2 min, 35 cycles of 95° C. 30 sec, 57° C. 30 sec, 72° C. 1 min, followed by 72° C. 5 min. 1 μL PCR product was TOPO cloned using the Zero-blunt TOPO cloning kit (Invitrogen) and individual clones were subjected to Sanger sequencing using the an SP6 priming site. 5mC conversion after βGT glucosylation and Tet oxidation was assessed in the same way.

Generation of Spiked-in Conversion Controls for H1 Cells. Several spiked-in controls were generated and tested. Spike-in control A consisted of a 1:1 mixture of unmethylated lambda DNA (Promega Cat. No. D1521) with M.SssI-converted pUC19 DNA (NEB, Cat. No. M0226S). To generate the spiked-in control B, unmethylated lambda DNA (Promega Cat. No. D1521) was PCR amplified and purified by gel electrophoresis in non-overlapping 2-kb amplicons, with a cocktail of dATP/dGTP/dTTP and either: d5mCTP (Zymo Research, Cat. No. D1035) at genomic positions 0-10 kb, dCTP at genomic positions 20-30 kb, and d5hmCTP (Zymo Research, Cat. No. D1045) at genomic positions 38-48 kb. Amplicons with d5mCTP/d5hmCTP and dCTP were amplified by ZymoTaq DNA polymerase (Zymo Research, Cat. No. E2001) and Phusion HF DNA polymerase (NEB, Cat. No. M0530S), respectively, as per manufacturers' instructions. Spiked-in DNA was added to H1 genomic DNA to a final concentration of 0.5% (control A for replicate 1, control B for replicate 2), and sonicated to a range of 300-500 bp with a Biorupter 300 (high power, 15 s on, 15 s off, 20 cycles).

Figures 18A, 18B, 18C, 18D, 18E, 18F, 18G, 18H, 18I, 18J:
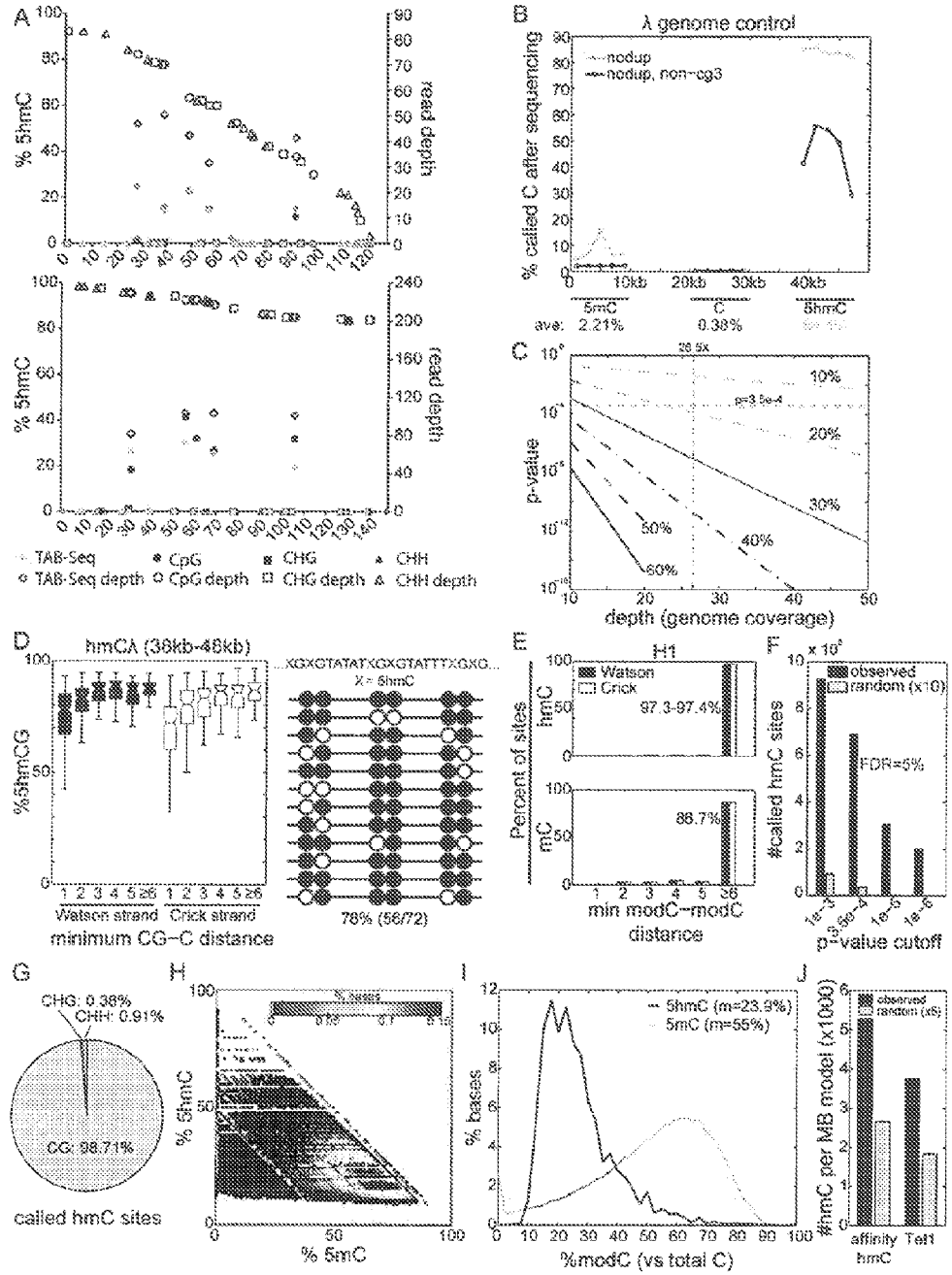
FIGS. 18A-18J (A) Validation of TAB-Seq signals by semiconductor sequencing. The left y-axis shows the percentage of bases read as C and the right y-axis shows the depth of sequencing at each C position in the targeted amplicon, which is plotted on the x-axis. For reference, TAB-Seq 5hmC calls (orange diamond) and TAB-Seq read depth (clear diamond) have been plotted on the same axes, with all other C signals and read depths being derived from the semiconductor sequencing experiments. (B) Lambda DNA was used as a spiked-in control as follows: regions 0-10 kb were amplified with 5mdCTP, regions 20-30 kb used dCTP, and regions 38-48 kb used 5hmdCTP. Shown is the percent of bases read as cytosine after high-throughput sequencing, for reads after PCR duplicate removal (green) and after additional removal of reads having greater than 3 cytosine base calls in non-CG context (red). The average percentage of cytosine base calls is indicated below. While the average 5hmC abundance of every cytosine in hmCλ is 84.4%, later analysis shows this rate increases to 87.0% when considering the subset of bases in the similar 5hmC content as mammalian genomes. (C) A theoretical calculation of the probability of calling a 5hmC for a given sequencing depth and a known abundance of 5hmC (percentages indicated), assuming a binomial distribution with parameter p as the 5mC non-conversion rate. Dotted lines indicate the average sequencing depth of H1 and the final p-value cutoff chosen at a false discovery rate of 5%. (D) The 38-48 kb region of lambda DNA (hmCλ), constructed by PCR amplification with 5hmCTP, was used to estimate the 5hmCG protection rate in mammalian cells. Shown is the protection rate of hmCλ as a function of distance to the closest cytosine to the CpG dinucleotide. Data for both strands are shown, and each strand was analyzed independent of the other strand. It was observed that hmC protection is most efficient when the closest neighboring hmC residue is 4 bases away (hmCNNNhmC), which was denoted as neighborless hmCs. However, even with the extreme case of hmCGhmCG (2 bases away) in hmCλ, the analysis shows that each 5hmC still has a ~80% non-conversion rate. To support this conclusion, a synthetic model DNA (right panel, sequence: 5'-CCTCACCATCTCAACCAATATTATATTANGNGTATATNGNGTATTTNGNGTTATA ATATTGAGGGAGAAGTGGTGA-3' (SEQ ID NO:3), N=5hmC) was prepared. After TAB-Seq, cloning and sequencing, it was observed at least 78% non-conversion rate for each 5hmC in the two hmCGhmCG sequences presented in the model DNA. (E) For each 5hmC (top) and 5mC (bottom) in H1, the distance to the nearest 5hmC and 5mC, respectively, was calculated. The distribution of these minimal distances is shown. Data for both strands are shown, and each strand was analyzed independent of the other strand. In H1, >98.8% of 5hmC and 94.4% of 5mC are separated by at least 4 bases to the nearest 5hmC and 5mC, respectively, indicating that the vast majority of 5hmC bases we observe are more efficiently protected. (F) The number of 5hmCs called for various p-value cutoffs of the binomial distribution, for actual data (black) and randomly sampled 5mCs (grey). The final p-value chosen was 3.5E-4, which corresponds to a false discovery rate of 5%. (G) Sequence context of 5hmC sites in mouse ES cells, compared to the reference mouse genome. (H) Heatmap of the abundance of 5hmC and 5mC for cytosines significantly enriched with 5hmC in mouse ES cells. 5mC was estimated as the rate from traditional bisulfite sequencing (5hmC+5mC) minus the measured 5hmC rate. (I) The distribution of the abundance of 5hmC (red, the left curve) and 5mC (green, the right curve) at the 5hmC sites in mouse ES cells. m: median. (J) In mouse ES cells, the overlap of 5hmCs (black) with 73,173 genomic regions identified as enriched by affinity mapping and 29,794 TET1 peaks identified by ChIP-Seq (Williams et al., 2011; Wu et al., 2011), in comparison to randomly chosen 5mCs (grey).
Figures 26A, 26B, 26C, 26D, 26E, 26F:
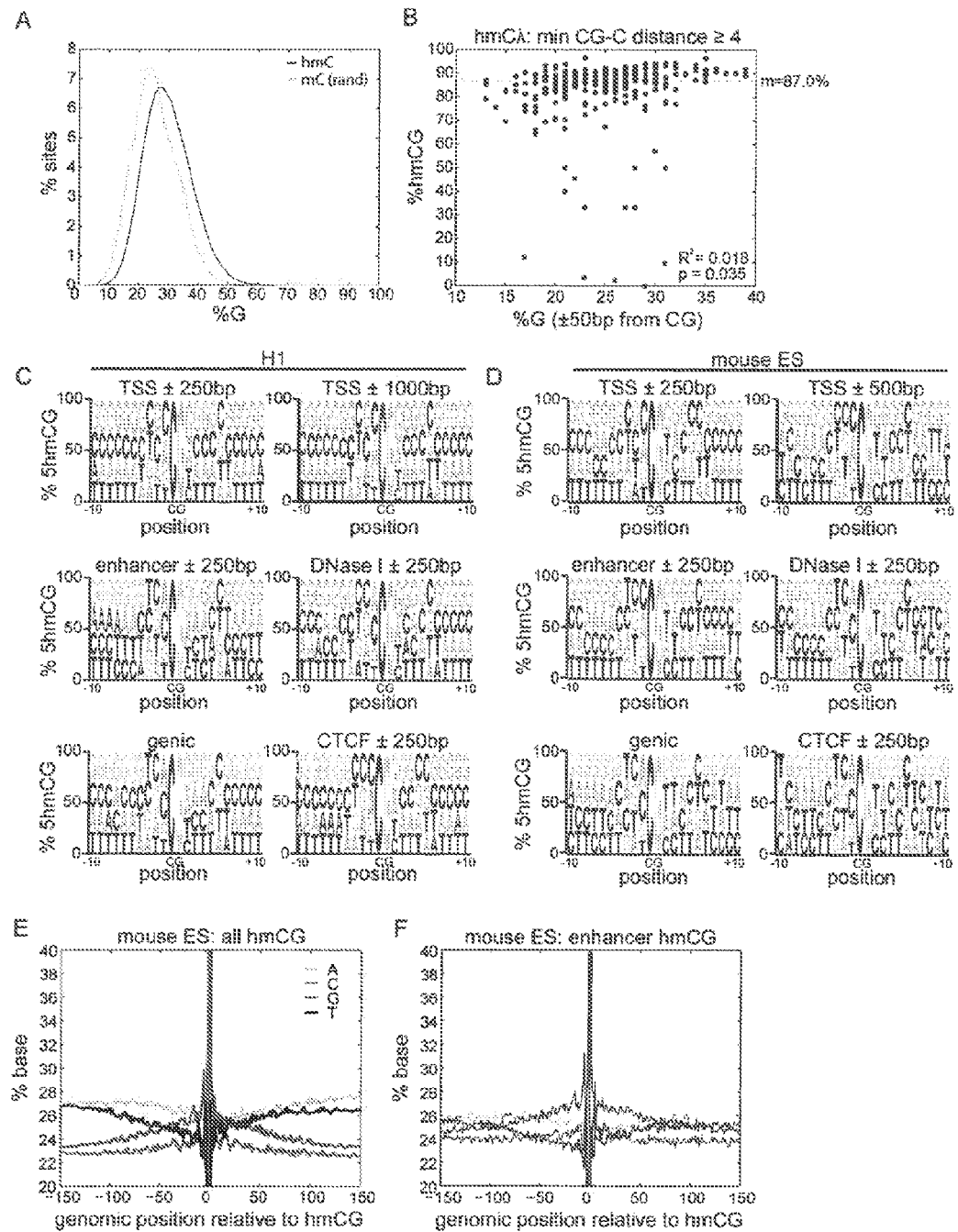
FIGS. 26A-26F (A) The percentage of guanine bases found in the 75-bp region [−25, +50] around 5hmCG sites, compared to randomly selected 5-methylcytosines. (B) In hmCλ, the abundance of 5hmC as a function of guanine content was plotted for all neighborless CpGs. The dotted line indicates the median 5hmC abundance. The data indicates that the guanine content around these bases does not significantly correlate with 5hmC abundance in hmCλ ($R^2=0.018$, p=0.035), indicating that the observations in H1 cells is not a result of TAB-Seq being biased. (C) In H1, the sequence context ±10 bp around 5hmCG sites that are on the Watson strand, for sites in various genomic elements. Similar results are observed on the Crick strand. (D) In mouse ES cells, the sequence context ±10 bp around 5hmCG sites that are on the Watson strand, for sites in various genomic elements. Similar results are observed on the Crick strand. (E) In mouse ES cells, the sequence context+150 bp around all 5hmCG sites. Shown sequences are on the same strand as the 5hmC base. Positive coordinates indicate the 3' direction. (F) In mouse ES cells, the sequence context+150 bp around the subset of 5hmCG sites at enhancers. Shown sequences are on the same strand as the 5hmC base. Positive coordinates indicate the 3' direction.

Assessing 5hmC Protection Rate in H1. To estimate the 5hmC protection rate in H1, we have performed further analysis of our spiked-in lambda control. The 38-48 kb region of lambda, which we designate hmCλ, was constructed by PCR amplification with 5hmCTP. Thus we assume that every cytosine sequenced in hmCλ exists as 100% 5hmC. As the structure of the glucose moiety of 5gmC suggests steric hindrance with neighboring 5gmC residues, we observe that 5hmC protection is most efficient when the closest neighboring 5hmC residue is at least 4 bases away (hmCNNNhmC), which we denote as neighborless 5hmCs (FIG. 18D, left). In H1, >98.8% of 5hmC and 94.4% of 5mC are separated by at least 4 bases to the nearest 5hmC and 5mC, respectively (FIG. 18E), indicating that the vast majority of 5hmC bases we observe are more efficiently protected. In hmC2, these neighborless 5hmCs in CG context are protected at a median level of 87.0% (FIG. 26B). In addition, even with an hmCGhmCG sequence (99.89% 5hmCs exist in CG context in H1) the analyses of both hmCλ and a model DNA indicate over 78% protection of each hmC (FIG. 18D)

Library Generation. 500 ng-1 μg treated genomic DNA was end-repaired, adenylated, and ligated to methylated (5mC) adapters (Illumina TruSeq Genomic DNA adapters) according to standard Illumina protocols for genomic DNA library construction, maintaining the proper molar ratios of adapter to insert. Adapter ligated fragments with 200-600 by inserts were gel purified by 2% agarose gel electrophoresis and sodium-bisulfate treated using the MethylCode kit (Invitrogen). Bisulfite treated adapter-ligated DNA was amplified by PCR with PfuTurbo Cx Hotstart DNA polymerase. The number of PCR cycles used was determined by quantification of bisulfite treated adapter-ligated DNA by qPCR (KAPABiosystems library quant kit for Illumina libraries) such that the final library concentration obtained was approximately 20 nM. Final sequencing libraries were purified with AMPure XP beads or 2% agarose gel electrophoresis and quantified by qPCR (KAPABiosystems library quant kit for Illumina libraries). Up to 3 separate PCR reactions were performed per sample.

TAB-Seq Library Sequencing. TAB-Seq libraries were sequenced using the Illumina HiSeq2000 platform. Cluster generation was performed with Illumina TruSeq-PE cluster kit v3-cBot-HS. 2× 101-bp sequencing was completed with Illumina TruSeq SBS kit v3-HS. A dedicated PhiX control lane, as well as 1% PhiX spike in all other lanes, was used for automated matrix and phasing calculations. Image analysis and base calling were performed with the standard Illumina pipeline.

Data Processing. Reads were processed as previously reported (Hon et al., 2012; Lister et al., 2009). Briefly, raw reads were trimmed for low quality bases and adapter sequences. Then, cytosine bases were computationally replaced with thymines, mapped with the Bowtie program (Langmead et al., 2009) against computationally converted copies of hg18 or mm9, and mapped reads were resorted to their pre-computationally-converted bases. PCR duplicates were removed for each PCR amplification reaction using the Picard program (http://picard.sourceforge.net). To eliminate reads not bisulfite converted, reads having more than 3 base calls in non-CG context were removed, as previously (Lister et al., 2009). All libraries were then merged and indexed by the SAMtools suite (Li et al., 2009).

Calling 5-Hydroxymethylcytosines. Since traditional bisulfite sequencing identifies both 5mC and 5hmC, we restricted our search space for 5-hydroxymethylcytosines to the subset of cytosines previously called as methylated by methylC-Seq/BS-Seq. For each such base, the inventors counted the number of "C" bases from TAB-Seq reads as hydroxymethylated (denoted $N_C$) and the number of "T" bases as not hydroxymethylated (denoted $N_T$). Then, the inventors used the binomial distribution having parameters N as the sequencing depth ($N_C+N_T$) and p as the 5mC non-conversion rate (2.22% for H1), to assess the probability of observing NC or greater cytosines by chance.

Assessing False Discovery Rate of 5hmC in H1. To estimate the false discovery rate of calling hydroxymethylated cytosines, the inventors repeated the steps above on randomly sampled methylcytosines. First, for each (chromosome chr, strand str, context con) combination, the inventors counted the number of cytosine base calls having Phred score ≥20 spanned by every read (denoted $C_{chr,str,con}$). Then, using calls of methylcytosines from methylC-Seq, the inventors randomly sampled $C_{chr,str,con}$ methylcytosines spanned by TAB-Seq reads on chromosome chr, strand str, and context con, with probability proportional to sequencing depth at each cytosine. This sampling method guarantees an equal chromosomal, strand, and context distribution as the original data, and normalizes for sequencing depth. Thus, the false discovery rate for a given p-value cutoff of the binomial distribution is the average number of hydroxymethylcytosines called in 10 random samplings divided by the number observed in the original data.

Quantifying Enrichment of 5hmC Bases at Genomic Elements. To calculate the enrichment of hydroxymethylcytosine calls at a set of genomic loci, the inventors counted the number of overlapping 5hmCs and divided by the average of 10 random samplings of hydroxymethylcytosine calls, as performed above. Finally, we normalized this enrichment value by the genomic span of the corresponding set of genomic elements.

Generation of E14Tg2a 5hmC Enrichment Profiles. 5hmC enrichment from E14Tg2a genomic DNA was done as previously described (Song et al., 2011) utilizing a 5hmC specific chemical labeling and capture approach. Sequence reads were generated and analyzed in the same manner as previously reported for H1 hES cells (Szulwach et al., 2011). Enriched regions were identified by MACS (Zhang et al., 2008) analysis with a p-value threshold of 1e-8 against a matched unenriched input genomic DNA library prepared and sequenced in parallel with the 5hmC enriched DNA.

ChIP-Seq Correlation at Distal Elements. To correlate %5hmCG with histone modifications measured by ChIP-Seq (Hawkins et al., 2010), the inventors calculated the enrichment of histone modifications at each DNase I hypersensitive site as log2 (ChIP RPKM/input RPKM), using a pseudocount as previously (Hon et al., 2012).

Figures 24A, 24B, 24C:
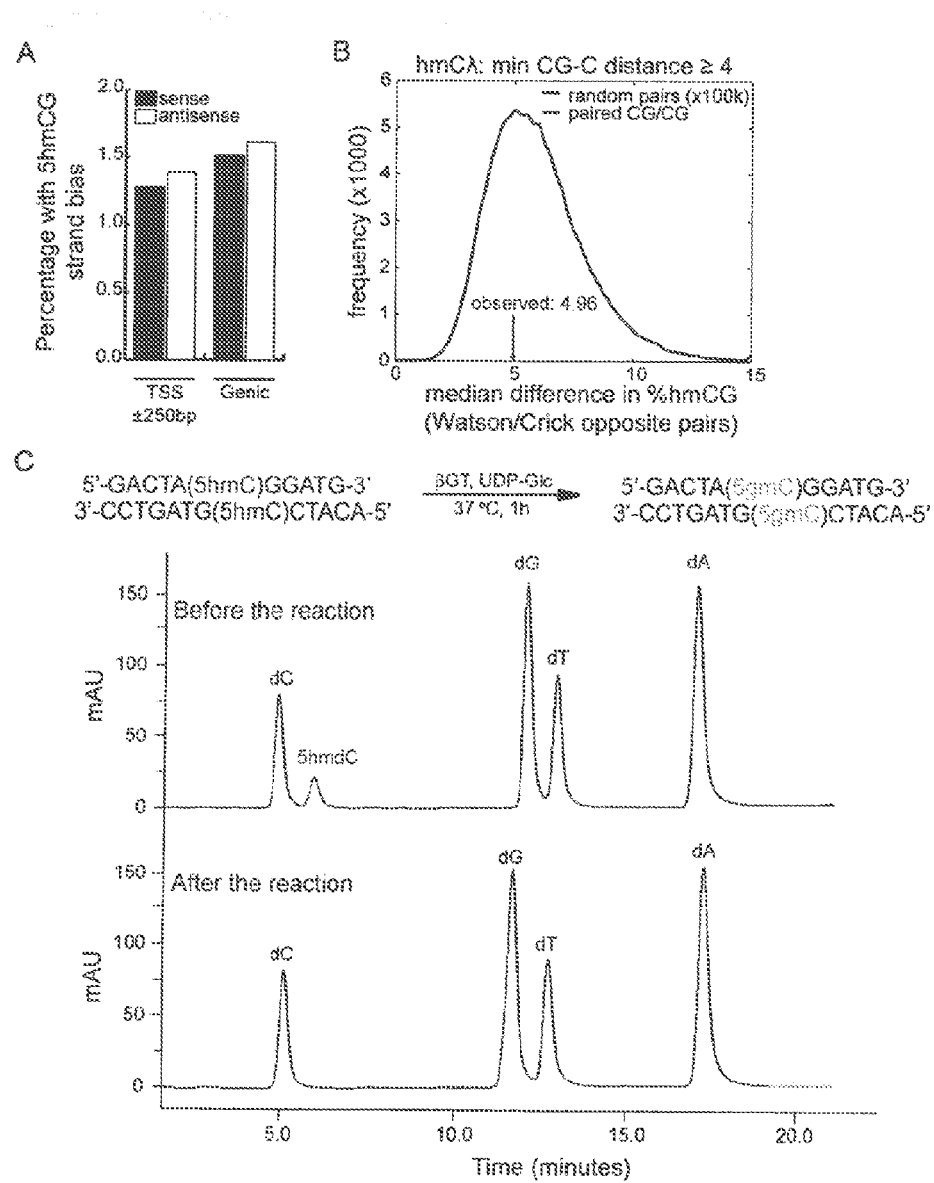
FIGS. 24A-24C (A) The percentage of promoters and gene bodies having significant strand bias of 5hmCG, relative to the direction of transcription. (B) There are 16 pairs of neighborless 5hmCGs in hmCλ, and shown in red is the asymmetry score (median absolute difference in 5hmCG abundance between pairs). The background distribution was computed as the asymmetry score of 100,000 randomly sampled sets of 16 neightborless CGs from each strand. The data indicates no asymmetry of 5hmCG in the control lambda DNA. Thus, our observations of asymmetry in H1 are not a result of the assay itself being biased. (C) HPLC chromatogram (at 260 nm) of the nucleosides derived from a fully-hydroxymethylated double-stranded DNA before and after βGT catalyzed glucosylation. The peak of 5hmC decreased dramatically after glucosylation which indicates that over 90% of 5hmC is protected. The 5gmC elutes within the peak of dG in the chromatograph; however, formation of 5gmC was independently confirmed by mass spectrometry analysis of the product DNA as shown in FIG. 15C.

Assessing Potential Biases in TAB-Seq. In H1, >98.8% of hmCs are separated by at least 4 bases to the nearest 5hmC (FIG. 18E). The inventors analyzed these neighborless 5hmC bases (hmCNNNhmC) within hmCλ. There are 16 pairs of neighborless 5hmCG's in hmCλ, which are assumed to be symmetrically modified by 5hmC. As a measure of asymmetry, the inventors computed the median absolute difference in 5hmCG abundance between pairs to be 4.96%. To get a background distribution for this asymmetry score, the inventors computed the same score for 100000 randomly sampled sets of 16 neighborless CGs from each strand. It was found that the observed asymmetry score is not significantly different from that expected by chance (FIG. 24B). In the remaining 1.2% hmCs in H1, even with an hmCGhmCG sequence (99.89% 5hmCs exist in CG context in H1) our analyses of both hmCλ and model DNA indicate over 78% protection of each hmC (FIG. 18D). Therefore, the inventors conclude that there is no asymmetry of 5hmCG in lambda DNA, and that our observations of asymmetry in H1 are not a result of the assay itself being biased. The inventors find that that guanine content is a predictor of 5hmC in H1 cells. To assess if this observation is a result of TAB-Seq being biased by sequence content, the inventors focused on neighborless 5hmC bases within hmCλ. Since hmCλ is assumed to be fully modified, the inventors expect no correlation between sequence content and 5hmC. It was found that guanine content around these bases does not significantly correlate with 5hmC abundance in hmCλ ($R^2=0.018$, p=0.035) (FIG. 26B), suggesting that the observations of the opposite to be true in H1 cells is not a result of TAB-Seq being biased.

External Data. CTCF ChIP-Seq peaks and DNase I hypersensitive sites for H1 ES cells were downloaded from the UCSC Genome Browser (Kent et al., 2002) and produced by the ENCODE Project Consortium (Myers et al., 2011). Distal regulatory elements are defined as those that are at least 5-kb from a transcription start site. Mouse Tet1 binding sites were derived from (Williams et al., 2011; Wu et al., 2011). Raw Tet1 ChIP-Seq sequence reads from both studies (SRA accessions: SRR070927, SRR070925, SRR096330, SRR096331) were aligned and monoclonal reads from each were combined into a single set. Peaks were identified against the combined set of IgG control monoclonal reads (SRA accessions: SRR070931, SRR096334, SRR096335), as well as monoclonal reads from the El4Tg2a input genomic DNA sample sequenced as part of this study, using a standard MACS analysis (Zhang et al., 2008).

Accession Numbers. Sequencing data have been deposited to GEO (accession GSE36173).

Results

Bisulfite sequencing has been broadly used to analyze the genomic distribution and abundance of 5mC (Bernstein et al., 2007; Clark et al., 1994; Lister et al., 2008; Meissner, 2010; Pelizzola and Ecker, 2011). However, because traditional bisulfite sequencing cannot distinguish 5mC from 5hmC, results from such approaches cannot yet accurately reveal 5mC abundance (Huang et al., 2010; Jin et al., 2010). Recent experiments show that 5hmC is widespread in the mammalian genome, and at least two functions have been proposed for this cytosine modification. First, 5hmC serves as an intermediate in the process of DNA demethylation, either passively since it is not replicated during mitosis (Inoue and Zhang, 2011), or actively through further oxidation (He et al., 2011; Ito et al., 2011; Maiti and Drohat, 2011; Zhang et al., 2012). Second, recent studies from several groups suggested that 5hmC is recognized by chromatin factors (Frauer et al., 2011; Yildirim et al., 2011), and that its presence could reduce binding of certain methyl-CpG-binding proteins (Hashimoto et al., 2012; Kriaucionis and Heintz, 2009; Valinluck et al., 2004). Importantly, these functions implicate two opposing notions about the relative stability of 5hmC at distinct genomic loci. As the first step toward understanding these molecular mechanisms associated with 5hmC function, it is important to not only precisely locate 5hmC in the genome, but also to determine the relative abundance at each modified site.

Described herein is a Tet-assisted bisulfite sequencing (TAB-Seq) strategy, which provides a method for single-base resolution detection of 5hmC amenable to both genome-wide and loci-specific sequencing. Combining this modified bisulfate sequencing method with conventional bisulfate sequencing can determine the location of 5hmC at single-base resolution and quantitatively assess the abundance of 5mC and 5hmC at each modified cytosine. Applying TAB-Seq strategy, the first genome-wide, single-base resolution maps of 5hmC in ESCs is generated. Distinct classes of functional elements exhibit variable abundance of 5hmC, with promoter-distal regulatory elements harboring the highest levels of 5hmC. High levels of 5hmC and reciprocally low levels of 5mC can be found near binding sites of transcription factors. In contrast to 5mC, most 5hmC sites display strand asymmetry and sequence bias. Finally, the base-resolution maps of 5hmC provide more accurate estimates of both 5hmC and 5mC levels at each modified cytosine than previous whole genome bisulfite sequencing approaches, which do not distinguish between these two DNA base modifications.

Figures 16A, 16B, 16C, 16D:
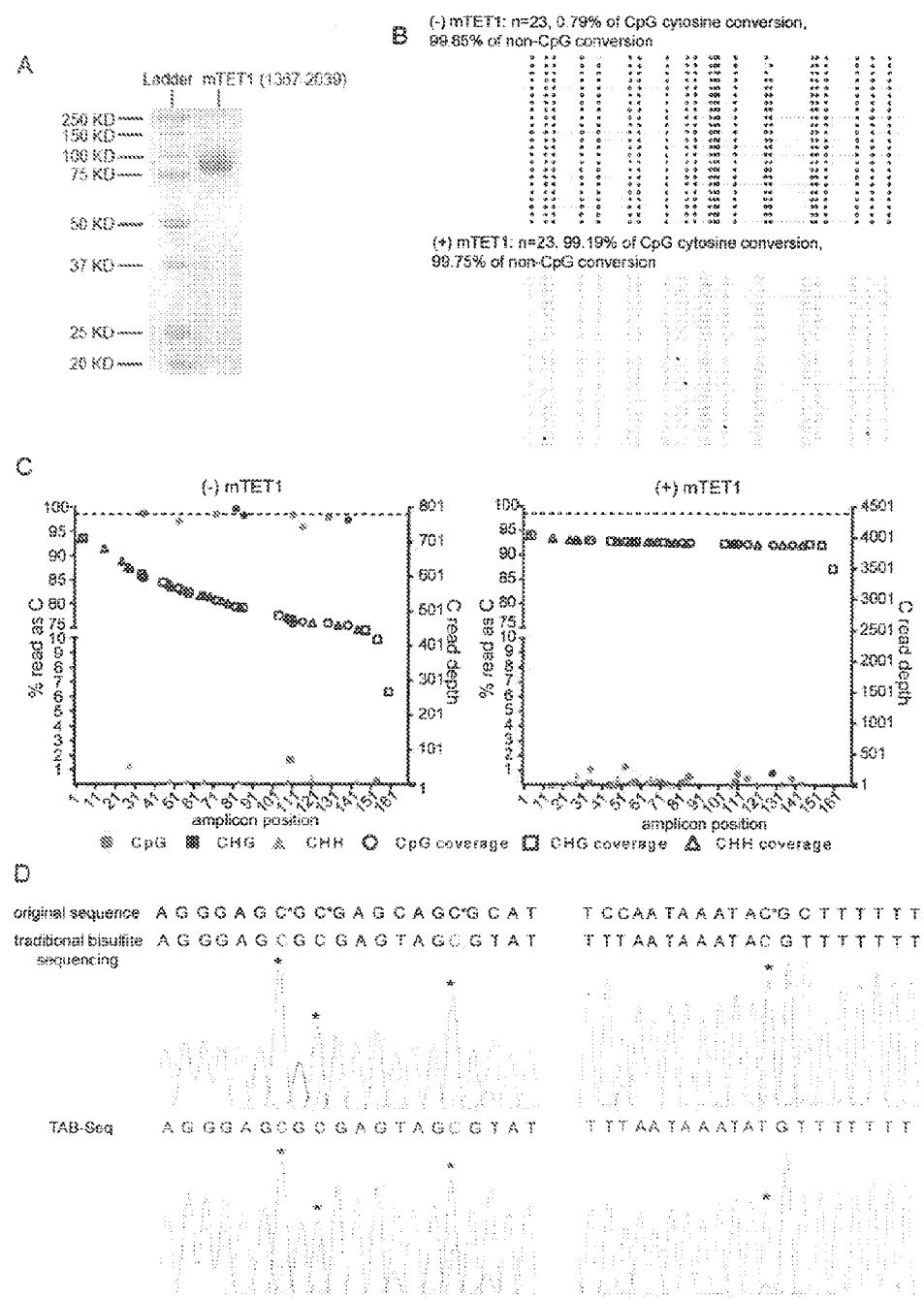
FIGS. 16A-16D TAB-Seq of Specific Loci and 5mC Conversion Rate Test in the Context of Genomic DNA. (A) Purified mTet1 catalytic domain used for oxidation of genomic DNA. (B) Sanger sequencing of M.SssI treated lambda DNA spiked into a genomic DNA background at 0.5% before (−mTet1) and after (+mTet1) subjecting the DNA to TAB-Seq. (C) Semiconductor sequencing of M.SssI-treated lambda DNA spiked into a genomic DNA background at 0.5% before (−mTet1) and after (+mTet1) subjecting the DNA to TAB-Seq. The left y-axis shows the percentage of bases read as C and the right y-axis shows the depth of sequencing at each C position in the targeted amplicon, which is plotted on the x-axis. For reference, a dotted line is plotted at 98% on the left y-axis. (D) Several loci in mouse cerebellum were tested by both traditional bisulfite sequencing and TAB-Seq. Genuine 5hmC is read as C in both methods (left) while genuine 5mC is read as C in traditional bisulfite sequencing but displays as T in TAB-Seq (right).

TAB-Seq of Model DNA and Specific Loci. Traditional bisulfite sequencing cannot discriminate 5mC from 5hmC because both resist deamination by bisulfite treatment (Huang et al., 2010; Jin et al., 2010). The inventors have recently shown that TET proteins not only oxidize 5mC to 5hmC, but also further oxidize 5hmC to 5caC, and that 5caC exhibits similar behavior as unmodified cytosine after bisulfite treatment (He et al., 2011; Ito et al., 2011). This deamination difference between 5caC and 5mC/5hmC under standard bisulfite conditions inspired the inventors to explore TAB-Seq. In this approach, a glucose is introduced onto 5hmC using β-glucosyltransferase (βGT), generating β-glucosyl-5-hydroxymethylcytosine (5gmC) to protect 5hmC from further TET oxidation. After blocking 5hmC, all 5mC is converted to 5caC by oxidation with excess of recombinant Tet1 protein. Bisulfite treatment of the resulting DNA then converts all C and 5caC (derived from 5mC) to uracil or 5caU, respectively, while the original 5hmC bases remain protected as 5gmC. Thus, subsequent sequencing reveals 5hmC as C, providing an accurate assessment of abundance of this modification at each cytosine (FIG. 15A). First, it has been confirmed that 5gmC is read as C in traditional bisulfite sequencing (data not shown). The catalytic domain of mouse Tet1 (mTet1) was cloned and expressed (FIG. 16A), as previously reported (Ito et al., 2010). In vitro activity tests confirmed that mTet1 oxidizes 5mC to 5caC as reported (He et al., 2011; Ito et al., 2011). The inventors tested a synthetic 76-mer double-stranded DNA with site-specifically incorporated 5mC or 5hmC modification to verify the feasibility of this approach (FIG. 15B). Application of this method with Sanger sequencing of the PCR amplified products showed that the original 5mC was completely converted into T after treatment, indicating efficient oxidation of 5mC to 5caC (FIG. 15B). However, the original 5hmC was sequenced as C, confirming that the protected 5gmC is resistent to deamination under bisulfite treatment (FIG. 15B). The products of each step were also confirmed by MALDI-TOF/TOF using a shorter model duplex DNA (FIG. 15C). Full conversion of 5mC in the context of genomic DNA was also confirmed by conventional bisulfite, PCR, and both Sanger and semiconductor sequencing (FIGS. 16B-C). Additionally, application to genomic DNA confirmed conversion of 5mC to 5caC, protection of 5hmC, and that 5fC is undetectable by immunoblot on the final reaction products (FIG. 15D). Thus, coupling βGT-mediated transfer of glucose to 5hmC with mTet1 oxidation of 5mC to 5caC enables the distinction of 5hmC from both C and 5mC after sodium bisulfite treatment.

The ability to distinguish 5hmC at base resolution offers a significant opportunity to further parse DNA methylation/hydroxymethylation states at specific genomic loci. The traditional bisulfite sequencing and TAB-Seq were applied to known 5hmC-enriched loci in mouse cerebellum which have been previously identified by affinity based 5hmC capture (Song et al., 2011; Szulwach et al., 2011b). Comparing the sequencing results, the genuine 5hmC sites were identified, which are read as C in both methods (FIG. 16D). In contrast, the inventors also identified genuine 5mC sites, which are read as C under traditional bisulfate treatment, but as T using TAB-Seq (FIG. 16D).

Generation of Base-Resolution Maps of 5hmC in Embryonic Stem Cell. TAB-Seq was applied to genomic DNA from H1 human ES cells and E14Tg2a mouse ES cells, and sequenced to an average depth of 26.5× and 17× per cytosine, respectively. Successful detection of 5hmC is governed by three key parameters: 1) efficient conversion of unmodified cytosine to uracil; 2) efficient conversion of 5mC to 5caU/U; and 3) efficient protection of 5hmC. To directly assess these conversion rates in the context of genomic DNA, sequenced samples were spiked in with fragments of lambda DNA amplified by PCR to contain three distinct domains having either unmodified cytosine, 5mC, or 5hmC. The inventors observe low non-conversion rates for unmodified cytosine (0.38%) and 5mC (2.21%), contrasted to a high non-conversion rate of 5hmC (84.4%) (FIG. 18B). Further analysis indicates that this latter value is an underestimate of the true 5hmC protection rate in H1, which is closer to 87.0% (FIG. 18D-E). These data further confirm the capability of TAB-Seq for robust distinction of 5hmC from 5mC and unmodified cytosine in the context of genomic DNA and demonstrate its utility for mapping relative 5hmC abundance at base resolution.

The inventors next focused on the map of H1 human ES cells, with comparison made to results obtained from mouse ES cells. To confidently identify 5hmC-modified bases the inventors took advantage of the highly annotated H1 methylome generated using methylC-Seq, which identifies both 5mC as well as 5hmC. Accordingly, the inventors restricted our search for 5hmC to the subset of methylated bases previously identified by methylC-Seq (Lister et al., 2009). The probability that a cytosine can be confidently identified as 5hmC is governed by the sequencing depth at the cytosine and abundance of the modification (FIG. 18C). Modeling this probabilistic event with a binomial distribution (Lister et al., 2009) with N as the depth of sequencing at the cytosine and p as the 5mC non-conversion rate, a total of 691,414 hydroxymethylated cytosines was identified with a false discovery rate of 5% (FIG. 18F). Given an average sequencing depth of 26.5, on average, this assay can resolve 5hmC having an abundance of 20% or higher (FIG. 18C). With increased sequencing depth, additional 5hmC bases with lower abundance may be found.

Figures 17A, 17B, 17C, 17D, 17E:
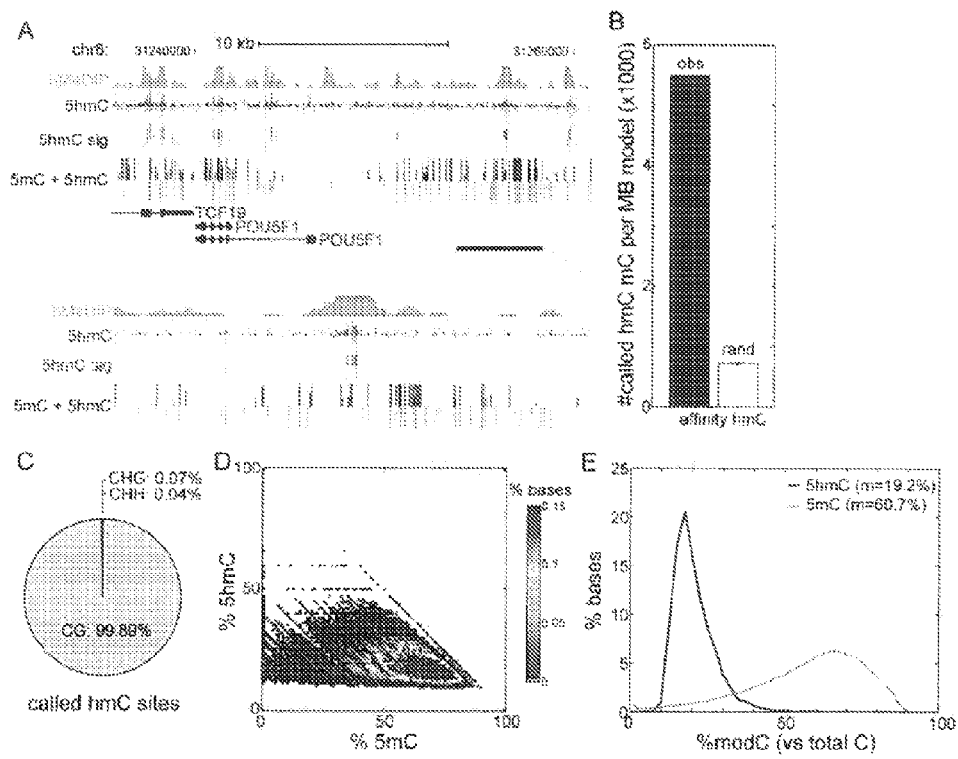
FIGS. 17A-17E Generation of Genome-wide Base-Resolution Maps of 5hmC. (A) Snapshot of base-resolution 5hmC maps (red) compared to affinity-based 5hmC maps (grey) in H1 cells near the POU5F1 gene. Also shown are base-resolution maps of traditional bisulfite sequencing in H1 cells (black). Positive values (darker shades) indicate cytosines on the Watson strand, whereas negative values indicate cytosines on the Crick strand. For 5hmC, the vertical axis limits are −50% to +50%. For traditional bisulfite sequencing, the limits are −100% to +100%. Only cytosines sequenced to depth ≥5 are shown. (B) Overlap of 5hmC with 82,221 genomic regions previously identified as enriched with 5hmC by affinity mapping (black), in comparison to randomly chosen 5mC (white). (C) Sequence context of 5hmC sites compared to the reference human genome. (D) Heatmap of estimated abundances of 5hmC and 5mC for modified cytosines significantly enriched with 5hmC. 5mC was estimated as the rate from traditional bisulfite sequencing (5hmC+5mC) minus the measured 5hmC rate. (E) The distribution of estimated abundances of 5hmC (red, the left curve) and 5mC (green, the right curve) at 5hmC sites. m: median.

Genomic profiles of absolute 5hmC levels are comparable to a map previously generated using an affinity-based approach (Szulwach et al., 2011a) (FIG. 17A). As sequenced fragments are equally distributed among the population of cells, TAB-Seq provides a steady-state glimpse of 5hmC in the entire population. This is in contrast to affinity-based approaches, which bias sequencing towards 5hmC-enriched DNA fragments. By TAB-Seq, identified 5hmCs are highly clustered, unlike 5mCs (FIG. 20A), and track well with peaks of 5hmC enrichment previously identified by affinity sequencing (FIG. 17A). There are 7.6 times as many 5hmCs overlapping affinity-identified regions as expected by chance (FIG. 17B, Z-score=1,579). Furthermore, 81.5% of these 82,221 affinity-identified regions were recovered by at least one 5hmC. In contrast, only 35.6% of 5hmCs are recovered by affinity-based approaches, suggesting an increased sensitivity of TAB-Seq. Using semiconductor sequencing, the presence/absence of 5hmC at 57 out of 59 individual cytosines (9 out of 11 hydroxymethylated CpGs, with depth ≥30) were verified within regions that previously escaped detection by 5hmC affinity capture (FIG. 18A), underscoring the sensitivity and specificity of the present described approach.

Application of TAB-Seq to mouse ESCs resulted in 2,057,636 high-confidence 5hmCs. This larger number of sites is likely attributable to higher level expression of both Tet1 and Tet2 in mouse ESCs as revealed by RNA-Seq analysis (Lister et al., 2011; Myers et al., 2011) (B.R., unpublished data). Like H1, these 5hmCs are also significantly enriched at genomic loci recovered by affinity sequencing (FIG. 18J). In addition, these hydroxymethylated sites are significantly enriched for previously mapped binding sites of Tet1 (Williams et al., 2011; Wu et al., 2011), confirming the TAB-Seq approach.

Base Composition and Genomic Distribution of 5-Hydroxymethylcytosine. DNA methylation of cytosines can exist in several contexts: CpG (denoted CG), CHG, and CHH (where H=A, C, or T). While it has been suggested that mouse ESCs may harbor 5hmC in non-CG content (Ficz et al., 2011) and while non-CG methylation is present in human and mouse ESCs (Lister et al., 2009; Stadler et al., 2011), it has been found that nearly all (99.89%) of H1 5hmCs exist in the CG context (FIG. 2C). Similarly, this figure is 98.7% in mouse ESCs (FIG. 18G).

Traditional bisulfite sequencing cannot resolve the steady-state abundance of 5hmC and 5mC at a given cytosine. However, the combination of methylC-Seq and TAB-Seq maps could estimate the true abundance of both 5hmC and 5mC. In a steady-state population of cells, 5mC and 5hmC often coexist at the same cytosine (FIG. 17D). The median observed abundance of 5hmC at 5hmC-rich cytosines is 19.2%, compared to 60.7% for 5mC as estimated from traditional bisulfite sequencing (FIG. 17E). Adjusting for the 87.0% protection rate of 5hmC by TAB-Seq, the corrected median 5hmC and 5mC abundance are estimated to be 22.1% and 57.8%, respectively. These results suggest that, at the base level, the abundance of 5hmC is lower than 5mC. This observation is corroborated in mouse ESCs (FIGS. 18H-I), and is consistent with a previous estimate of global 5hmC levels in embryonic stem cells (Tahiliani et al., 2009).

Figures 19A, 19B, 19C, 19D, 19E, 19F:
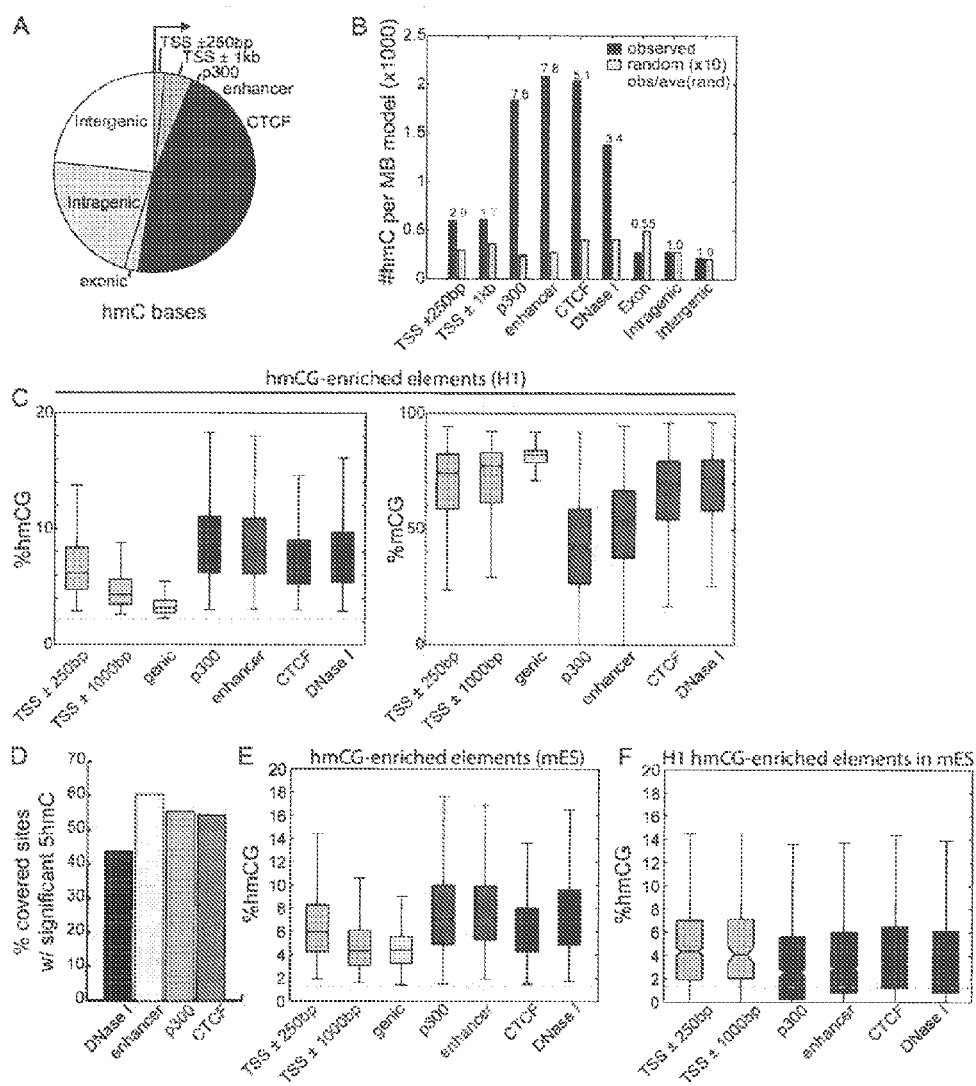
FIGS. 19A-19F Genomic Distribution of 5hmC Sites. (A) Overlap of H1 5hmC with genomic elements. Genic features were extracted from the UCSC Known Genes database (Hsu et al., 2006). Promoter-distal regulatory elements (>5 kb from TSS) reflect those experimentally mapped in H1 cells from ChIP-Seq and DNase-Seq experiments. Each 5hmC base is counted once: the overlap of a genomic element excludes all previously overlapped cytosines counterclockwise to the arrow. Green: promoter-proximal; red: promoter-distal regulatory elements; grey: genic regions; white: intergenic regions. (B) The relative enrichment of H1 5hmC (black) and random sites (grey) at genomic elements, normalized to the total coverage of the element type. Random consists of 10 random samplings of 5mC (see Extended Experimental Procedures). (C) The levels of 5hmCG (left) and 5mCG (right) for several classes of genomic elements significantly enriched with 5hmCG in H1 (p=0.01, binomial). The dotted line indicates the 5mC non-conversion rate. Colors as in (A). (D) The percentage of distal regulatory elements significantly enriched with 5hmCG in H1. (E) In mouse ES cells, the absolute level of 5hmCG for several classes of genomic elements significantly enriched with 5hmCG (p=0.01, Fisher's exact test). Colors as in (A). (F) For genomic elements significantly enriched with 5hmCG in H1 ES cells and conserved in mouse, the distribution of 5hmCG in mouse ES cells. Colors as in (A). In all panels, definitions of enhancers, p300, CTCF, and DNase I sites are promoter-distal (>5-kb from TSS).
Figures 20A, 20B, 20C, 20D, 20E, 20F, 20G, 20H, 20I, 20J, 20K, 20L:
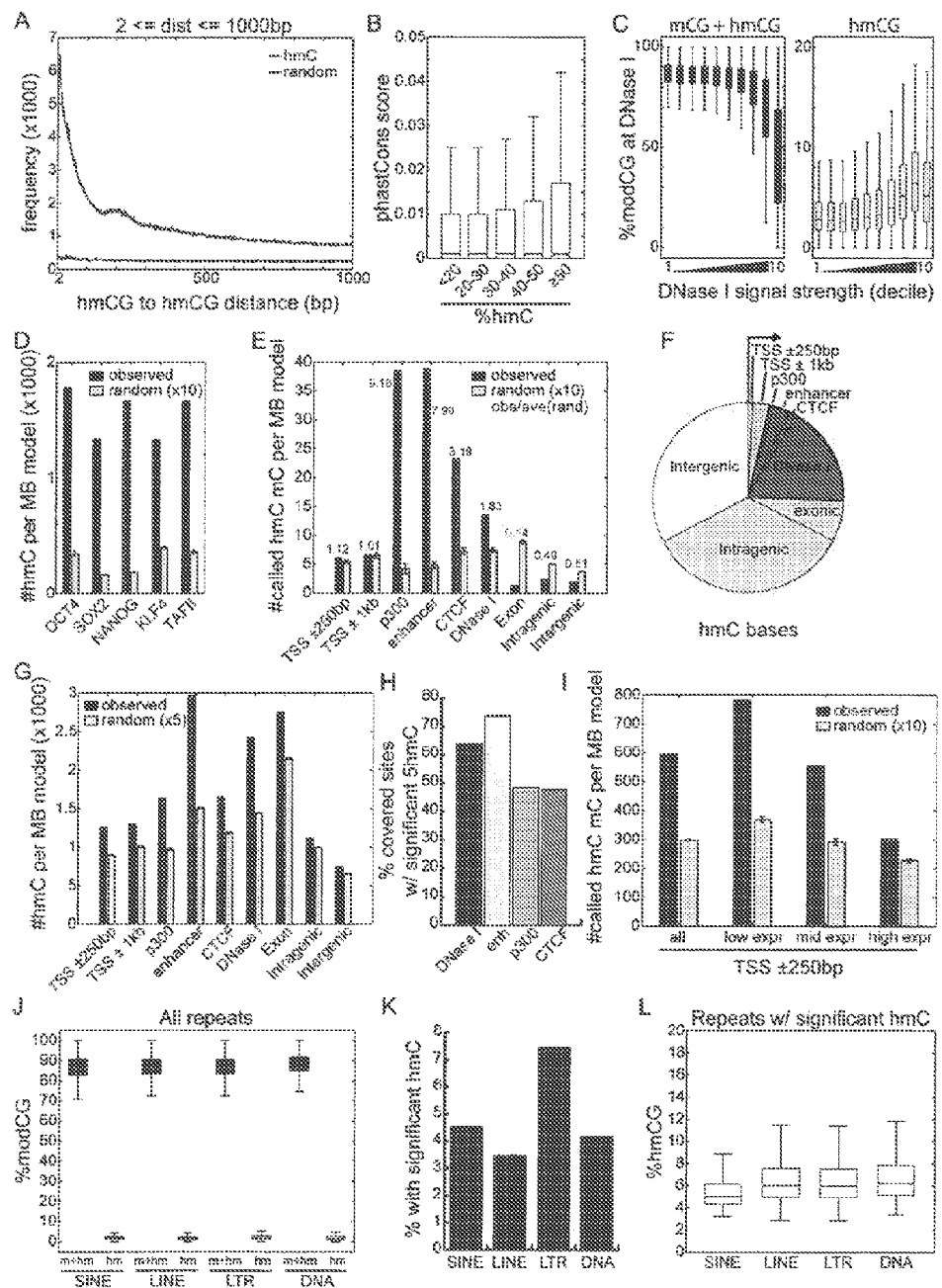
FIGS. 20A-20L (A) The distribution of pair-wise distances between all 5hmCs identified in H1 (red, top line), compared to the same number of randomly selected 5mCs (black, bottom line). (B) The distribution of base-level phastCons conservation scores (Siepel et al., 2005) for several tiers of 5hmC abundance. (C) Total methylation level measured by methylC-Seq (left) and the 5hmC abundance measured by TAB-Seq (right) for DNase I hypersensitive elements ranked by signal strength. (D) The relative enrichment of H1 5hmCs (black) and random sites (grey) at promoter-distal ChIP-Seq peaks, normalized to the total coverage of the element type. Random consists of 10 random samplings of 5mCs. (E) For the subset of H1 cytosines having a ratio of 5hmC to 5mC between 0.9 and 1.10, shown is the relative enrichment of sites (black) and random sites (grey) at genomic elements, normalized to the total coverage of the element type. Random consists of 10 random samplings of 5mCs. (F) Overlap of mouse ES cell 5hmCs with genomic elements. Promoter-distal regulatory elements (>5 kb from TSS) reflect those experimentally mapped in mouse ES cells from ChIP-Seq and DNase-Seq experiments. Each 5hmC base is counted once: the overlap of a genomic element excludes all previously overlapped cytosines counterclockwise to the arrow. Green: promoter-proximal; red: promoter-distal regulatory elements; grey: genic regions; white: intergenic regions. (G) The relative enrichment of mouse ES cell 5hmCs (black) and random 5mCs (grey) at genomic elements, normalized to the total coverage of the element type. Random consists of 5 random samplings of 5mCs (see Extended Experimental Procedures). (H) The percentage of distal regulatory elements significantly enriched with 5hmCG in mouse ES cells. (I) H1 promoters were divided into three equally sized groups based on the expression of corresponding genes. Shown is the relative enrichment of 5hmCs (black) and random sites (grey) at these promoters, normalized to the total coverage of each group. Random consists of 10 random samplings of 5mCs (see Extended Experimental Procedures). (J) Shown is the distribution of total methylation (5mC+5hmC) and 5hmC abundance at repetitive elements that do not overlap with regulatory elements (promoters, p300/CTCF binding sites, enhancers, DNase I hypersensitive sites). Elements with less than 50 C+T calls for either methylC-Seq or TAB-Seq were excluded. (K) The percentage of repetitive elements significantly enriched with 5hmCG in H1. (L) The absolute level of 5hmCG for several classes of repetitive elements significantly enriched with 5hmCG in H1 (p=0.01, binomial).

Previous studies using affinity-based approaches have demonstrated that 5hmC is enriched at promoters, enhancers, CTCF binding sites, exons, and gene bodies (Ficz et al., 2011; Pastor et al., 2011; Stroud et al., 2011; Szulwach et al., 2011a; Williams et al., 2011; Wu et al., 2011; Xu et al., 2011), suggesting an extensive role for this modification in gene regulation. Supporting a functional role of 5hmC, the inventors observe a trend of increasing sequence conservation for increasing abundance of 5hmC (FIG. 20B). However, the absolute abundance of 5hmC cannot be assessed from affinity-based detection methods, therefore precluding further quantitative analysis of 5hmC's role at each class of regulatory elements. In H1, almost half (46.4%) of the 5hmCs reside in distal regulatory elements mapped by ChIP-Seq and DNase-Seq (FIG. 19A). Assessing relative enrichment of 5hmC at each class of regulatory element by normalizing with genomic coverage, H1 distal regulatory elements including p300 binding sites (observed/expected=7.6), predicted enhancers (o/e=7.8), CTCF binding sites (o/e=5.1), and DNase I hypersensitive sites (o/e=3.4) are more enriched with 5hmC than other genic regions (FIG. 19B). Intriguingly, the subset of cytosines showing nearly equal levels of 5mC and 5hmC are more enriched in distal regulatory elements and less enriched at promoters and genic features (FIG. 20E), suggesting that active demethylation is strongest outside of genes. In support of this observation, promoter-distal ChIP-Seq peaks for OCT4, SOX2, NANOG, KLF4, and TAFII are also more enriched with 5hmC than genic features (FIG. 20D). Finally, the increasing DNase I hypersensitivity signal correlates well with increased 5hmC and decreased 5mC enrichment (FIG. 20C). These results are also supported by observations in mouse ESCs (FIG. 20E-G), though the inventors observe an increase in intragenic 5hmC occupancy, perhaps due to the role of increased Tet2 expression.

Examining only those genomic elements having significant 5hmC enrichment, it has been found that the absolute levels of 5hmC at all classes of distal regulatory elements are significantly higher than promoter-proximal elements (FIG. 19C). In contrast, gene bodies with significant levels of 5hmC show statistically lower levels of 5hmC. Furthermore, examining the estimated level of 5mC at these loci, an inverse relationship between 5mC and 5hmC was observed (FIG. 19C). Distal regulatory elements have the lowest levels of 5mC, with p300 and enhancers having median abundances of 42.2% and 53.7%, respectively. This suggests that highly demethylated elements such as p300 contain more cytosines in a non-5mC/5hmC form, implicating stronger demethylation at these regulatory elements.

In combination with the observations that: 1) between 44% and 74% of distal regulatory elements are significantly enriched with 5hmC in human and mouse ESCs (FIG. 19D, 20H); 2) the same class of elements are also enriched in mouse ESCs (FIG. 19E, 20G); and 3) the sequence-conserved distal-regulatory elements in H1 are conserved for 5hmC in mouse ESCs (FIG. 19F), the data suggests that the marking of functional regulatory elements with 5hmC is an evolutionarily conserved phenomenon with potential functional consequences. Together, these data show that 5hmC is most abundant at promoter-distal regulatory elements, and particularly enriched in distal regulatory elements.

Besides distal regulatory elements, it has been observed that significant enrichment of 5hmC at genes of all tiers, but lowly expressed genes are more enriched than highly expressed genes (FIG. 20I), consistent with previous studies (Pastor et al., 2011). Also, in contrast to the abundant 5hmC found at regulatory elements in H1, the vast majority of repetitive elements are highly enriched with 5mC, but not 5hmC (FIG. 20J). Depending on the type of repeat, between 3.5 and 7.5% of repetitive elements are significantly enriched with 5hmC, with LTRs being the highest (FIG. 20K). At these significant loci, the absolute abundance of 5hmC is on par with promoters, but less than distal-regulatory elements (FIG. 20L).

Figures 21A, 21B, 21C, 21D:
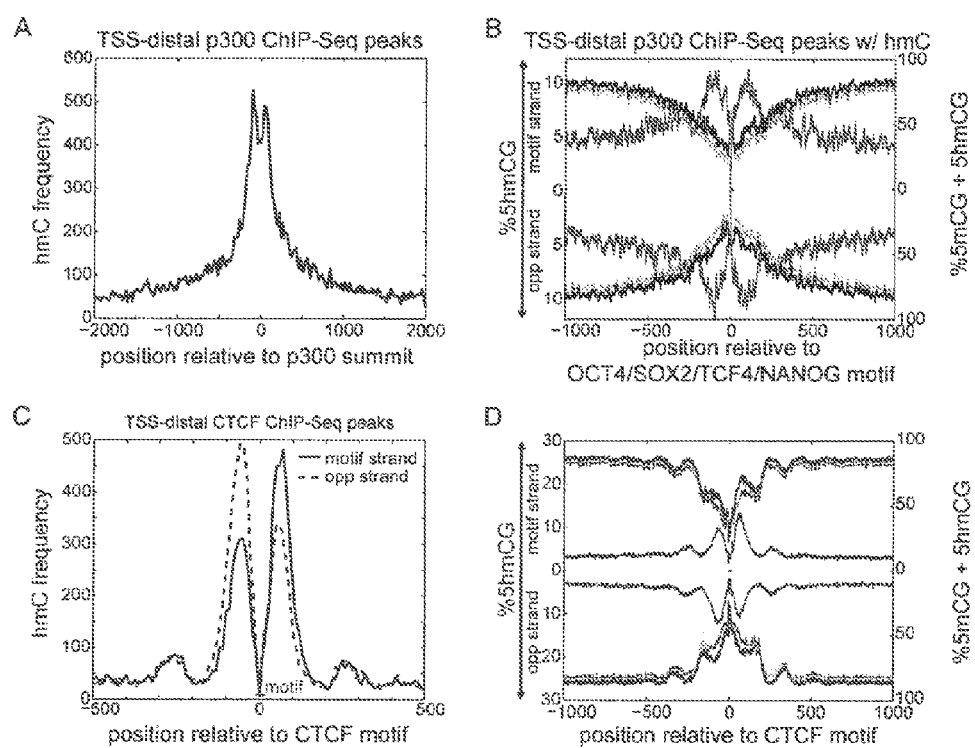
FIGS. 21A-21D Profiles of 5hmC at Distal Regulatory Elements. (A) Frequency of 5hmC around distal p300 binding sites. (B) Absolute levels of 5hmCG (red) and 5mCG+5hmCG (black) around the distal p300 binding sites containing an OCT4/SOX2/TCF4/NANOG motif (blue bar, center; consensus: ATTTGCATAACAATG (SEQ ID NO:4)). 5mC (green) was estimated as the rate from traditional bisulfite sequencing (5hmC+5mC) minus the measured 5hmC rate. The top half indicates enrichment on the strand containing the motif, with the bottom half indicating the opposite strand. (C) Frequency of 5hmC around distal CTCF binding sites, relative to the CTCF motif (blue bar, bottom). The different lines represent different strands, oriented with respect to the CTCF motif (consensus: ATAGTGCCACCTGGTGGCCA (SEQ ID NO:5)). Opp, opposite. (D) Absolute levels of 5hmCG, 5mCG, and 5mCG+5hmCG around distal CTCF binding sites anchored at the CTCF motif (blue bar, center). Colors as in (B).
Figures 22A, 22B, 22C:
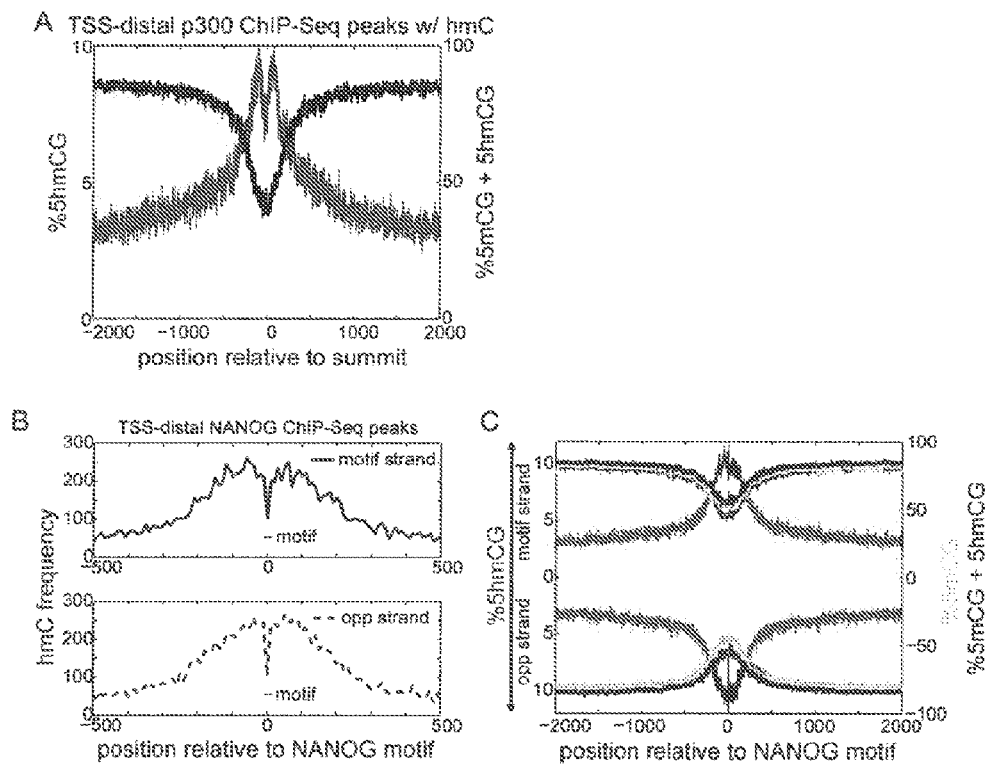
FIGS. 22A-22C (A) Absolute levels of 5hmCG (red) and 5mCG+5hmCG (black) around distal p300 binding sites. Peaks were identified by MACS (Zhang et al., 2008), and the p300 binding site was estimated as the MACS summit location. (B) Frequency of 5hmC around distal NANOG binding sites, relative to the NANOG motif (blue bar). The different lines represent the different strands, oriented with respect to the NANOG motif (consensus: GGCCATTAAC (SEQ ID NO:6)). Opp, opposite. (C) Absolute levels of 5hmCG (red) and 5mCG+5hmCG (black) around distal NANOG binding sites containing an NANOG motif (blue bar, center; consensus: GGCCATTAAC (SEQ ID NO:6)). 5mC (green) was estimated as the rate from traditional bisulfite sequencing rate (5hmC+5mC) minus the measured 5hmC rate. The top half indicates enrichment on the strand containing the motif, with the bottom half indicating the opposite strand.

Profiles of Hydroxymethylcytosine at Distal Regulatory Elements. 5mC is thought to confer specificity to gene regulation by influencing transcription factor binding or serving as a substrate of recognition for chromatin regulators (Bird, 2011; Chen and Riggs, 2011; Jaenisch and Bird, 2003; Quenneville et al., 2011). Similarly, it has been suggested that 5hmC offers a different platform upon which transcription factors may bind or 5mC specific binding proteins may be excluded (Hashimoto et al., 2012; Kriaucionis and Heintz, 2009; Valinluck et al., 2004; Yildirim et al., 2011). Since 5hmC is enriched near enhancers, one possibility is that this modified base is specifically recognized by transcription factors as a core base in binding motifs. But as sequence motifs are typically shorter than 20 bp, the resolution of affinity-based approaches is not sufficient to resolve whether 5hmC is actually present within or outside of the binding site. It has been observed that while 5hmC is abundant within 500 bp of distal p300 binding sites, there is a local depletion near the expected TF binding site (FIG. 21A, FIG. 22A). To determine whether this observation holds at an increased resolution, the inventors anchored p300 binding with the OCT4/SOX2/TCF4/NANOG consensus motif (Lister et al., 2009). Total DNA methylation (5mC+5hmC) decreases towards the motif, in agreement with a recent study (Stadler et al., 2011), while 5hmC displays a bimodal peak of enrichment centered at the motif with a maximum average abundance of 12.3% (FIG. 4B).

Similarly, by anchoring CTCF binding sites with the CTCF consensus motif, the inventors observed a bimodal enrichment profile of 5hmC abundance ~150 bp around the motif, with almost no 5hmC within the motif itself (FIG. 21C). Hydroxymethylation increases to a maximum abundance of 13.4%, coinciding with a dramatic depletion of 5mC from an average high of 86.2% to a low of 21.0% (FIG. 21D). The inventors also observe similar results for NANOG binding sites (FIGS. 22B-C). Together, these data suggest that 5hmC is typically not observed within potential binding sites of transcription factors, but rather are most enriched in regions immediately adjacent to sequence motifs. The reciprocal profiles of 5hmC and 5mC is consistent with a model of dynamic DNA methylation associated with DNA-binding transcription factors, and provides additional evidence supporting a role for 5hmC in the locally reduced levels of 5mC at distal regulatory elements (Stadler et al., 2011).

Figures 23A, 23B, 23C, 23D, 23E:
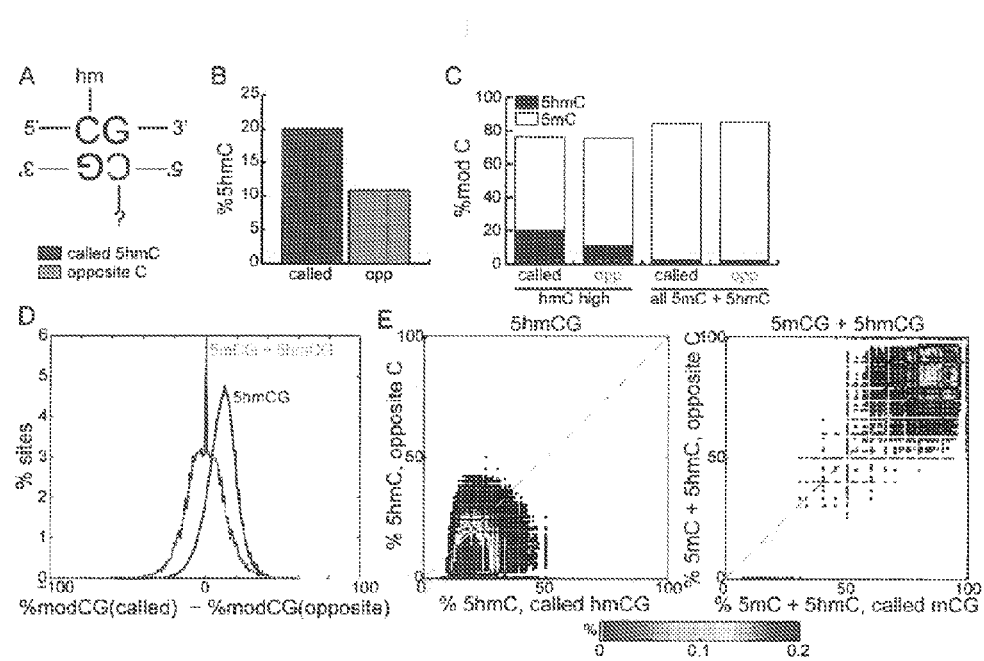
FIGS. 23A-23E Asymmetry around 5hmCG. (A) A schematic of nomenclature. The cytosine with 5hmC (red) designated as "called", while the cytosine on the opposite strand (green) is designated as "opposite". (B) The average 5hmC abundance of called 5hmCG residues (red) compared to the opposite cytosine residues (green). called: called cytosine; opp: opposite cytosine. (C) The average 5hmC (black) and 5mC (white) abundance at called and opposite cytosines, for called cytosines having 5hmC (left) or 5mC+5hmC (right). 5mC (white excluding black) was estimated as the rate from traditional bisulfite sequencing (5hmC+5mC) minus the measured 5hmC rate. Grey line: methylcytosine non-conversion rate. (D) The distribution of differences in 5hmCG (red) between called and opposite cytosines, in comparison to differences observed from traditional bisulfite sequencing (green, 5mCG+5hmCG). Called and opposite cytosines are each sequenced to at least depth 10. (E) For 5hmC-called sites, a heatmap of 5hmCG abundance at called and opposite cytosine pairs (left). For the 5mC-called sites from traditional bisulfite sequencing, a heatmap of 5mCG+5hmCG abundance at called and opposite cytosine pairs (right).

Asymmetric Hydroxymethylation at CG Sequences. Cytosine methylation in CG context is symmetric, and the maintenance methyltransferase DNMT1 ensures efficient propagation of symmetric 5mCG during cell division, thus providing one of the central modes of epigenetic inheritance (Bird, 2011; Chen and Riggs, 2011; Goll and Bestor, 2005; Jaenisch and Bird, 2003; Wigler et al., 1981). The observation that the bimodal distribution of 5hmC around CTCF is strand-asymmetric (FIGS. 21C-D) prompted the inventors to examine if hydroxymethylation is strand-biased in H1. While 91.8% of 5mCs are symmetrically modified, only 21.0% of 5hmCs are symmetric. However, since the abundance of 5hmC is rare at any given cytosine (median 19.2%, FIG. 17E), it is possible that sequencing depth was not sufficient to identify all 5hmCs, making this an underestimate. To address this issue, the pool of all called 5hmCs were compared with the pooled 5hmC content on the opposite cytosine (FIG. 23A). The average abundance of 5hmC is 20.0% at called 5hmCs, compared to 10.9% at the opposite cytosine, which corresponds to an 83.8% enrichment of 5hmC (FIG. 23B, p<1E-15, binomial). As a control, the base-line 5hmC content of all methylated cytosines in CG context is symmetric and comparable to the methylcytosine non-conversion rate (FIG. 23C). At promoters and within gene bodies, strand bias is not dependent on the orientation of the transcript (FIG. 24A) ($p_{promoter}$=0.0339, $p_{gene\ body}$=0.0719).

To confirm the asymmetry of 5hmCG, the difference in methylation state of called 5hmCs and the cytosines located at the opposite strands were examined. From traditional bisulfite sequencing, the median difference in total methylation (5mCG+5hmCG) between called and opposite cytosines is 0%. In contrast, TAB-Seq reveals a shifted distribution with a median of 10.9% less hydroxymethylation on the opposite cytosine (FIG. 23D, p<1E-15, Wilcoxon). Simultaneous examination of the absolute levels of hydroxymethylation on both called and opposite cytosines showed that the shift in hydroxymethylation state towards the called cytosine is evident, in contrast to DNA methylation levels that remain symmetric (FIG. 23E). The analysis of the spiked-in lambda DNA showed no strand nor sequence bias of the TAB-Seq method (FIG. 24B, FIG. 18D). This conclusion was further supported by analyzing the βGT-catalyzed glucosylation efficiency of a fully-hydroxymethylated model dsDNA, which was over 90% (FIG. 24C).

Figures 25A, 25B:
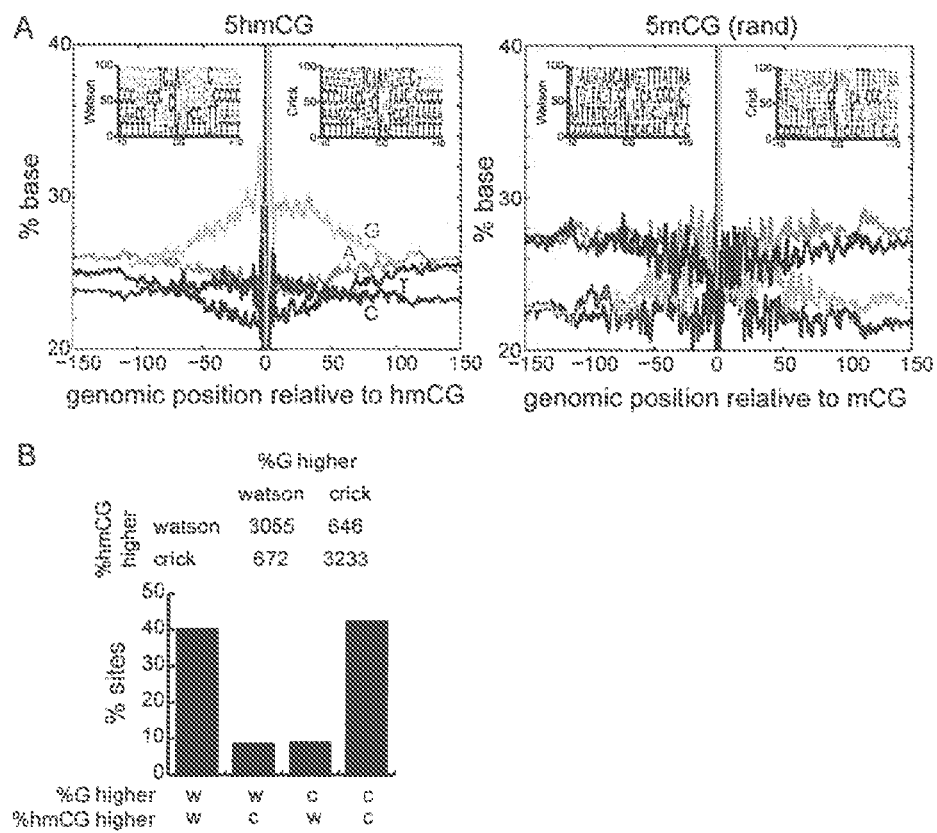
FIGS. 25A-25B Local Sequence Context around 5hmCG. (A) Sequence context ±150 bp around 5hmCG sites (left), compared to the same number of randomly chosen mCG sites (right). Shown sequences are on the same strand as 5hmC. Inset: sequence context ±10 bp around 5hmCG sites that are on the Watson or Crick strands. Positive coordinates indicate the 3' direction. (B) For cytosines showing significant difference in 5hmCG between Watson and Crick strands (p=0.01, Fisher's exact test), and for which the abundance of guanine ±50 bp around the site showing significant strand bias (p=0.01, Fisher's exact test), shown is the frequency at which these two events co-occur.

5hmC is Strand-Biased towards G-rich Sequences. The asymmetry of 5hmC in H1 suggests that, on a population average, one strand is more likely to be hydroxymethylated than the other strand. One possible explanation for this phenomenon is a sequence preference of hydroxymethylation for one strand compared to the other. To examine this systematically, the inventors aligned all 5hmCs in CG context and examined base composition (FIG. 25A). On the strand containing 5hmC, a modest increase in local guanine abundance with depletion of adenine and thymine content was observed. The human genome consists of ~20% each of guanine and cytosine and ~30% each of adenine and thymine. Within a window of 100 bp around 5hmCs, the local sequence content of guanine increases to an average of 29.9%, significantly higher than the 25.6% observed for randomly sampled methylated cytosines (FIG. 26A, $p<1E-15$, Wilcoxon). These observations are not a function of regulatory element class, as similar trends hold for subsets of 5hmC found at promoters, distal regulatory elements, and genic regions (FIG. 26C). Furthermore, similar trends are observed in mouse ESCs (FIG. 26D), and analysis of the spiked-in lambda DNA shows that this observation is not a systematic bias of the TAB-Seq method (FIG. 26B).

These observations suggest that hydroxymethylation of cytosine is biased towards the strand with a higher local density of guanine. To test this hypothesis, a predictive algorithm was developed: given that a strand-biased hydroxymethylation event exists at a particular CG (p-value=0.01, Fisher's exact test) and that one strand has local guanine content significantly different from the other strand (p-value=0.01, Fisher's exact test), the inventors predict the strand with higher guanine content to have the hydroxymethylation event. This model correctly predicts the hydroxymethylated strand with 82.7% accuracy, significantly better than the 50% expected by chance (FIG. 25B, $p<1E-15$, binomial), confirming that local sequence content plays a role in strand-specific hydroxymethylation. However, while both human and mouse ESCs exhibit a bias of 5hmCG to occur on the strand with more guanine content (FIGS. 26C-D), the effect is weaker in mouse ESCs (FIG. 26E-F), which is one potential reason that guanine content does not predict 5hmC in mouse ES cells. One possible explanation is the large difference in the expression levels of TET1 and TET2 in human and mouse ESCs.

Figures 27A, 27B, 27C, 27D, 27E, 27F:
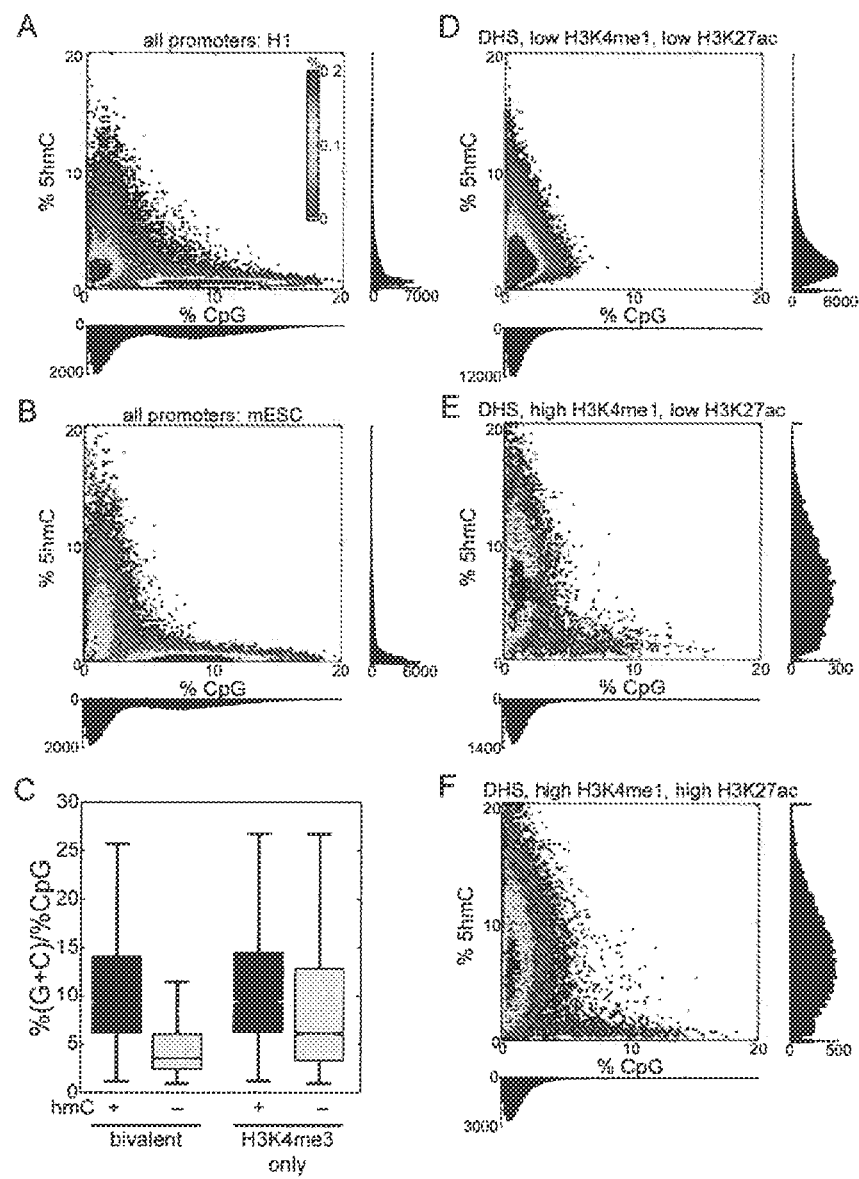
Figures 28A, 28B, 28C, 28D, 28E, 28F, 28G, 28H:
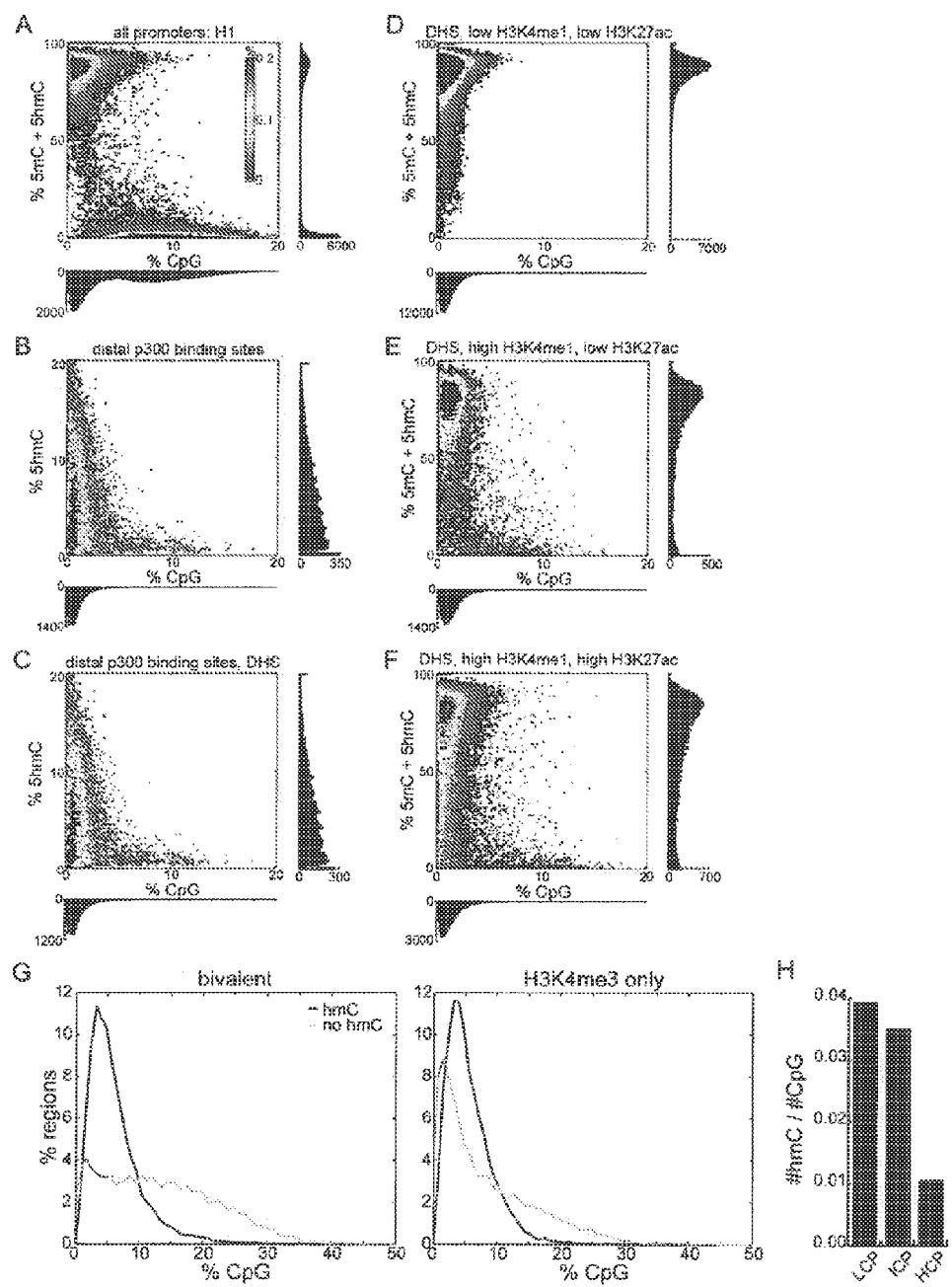

5hmC is Most Enriched near Low CpG Regions. Recent affinity-based studies in mouse ESCs have observed 5hmC to be frequently enriched at CpG island-containing promoters (Ficz et al., 2011; Pastor et al., 2011; Williams et al., 2011), and that the highest levels of 5hmC correspond to the highest density of CpGs (Ficz et al., 2011). In contrast, an affinity-based map of 5hmC produced in H1 found 5hmC-rich regions to be depleted of CpG dinucleotides (Szulwach et al., 2011a). These confounding results prompted the inventors to examine the relationship between absolute steady-state hydroxymethylation level and CpG content at promoters. The promoters with the highest levels of 5hmCG are almost exclusively of low CpG content (FIG. 27A), which are also the promoters most likely to have the highest 5mCG (FIG. 28A). In agreement with this observation, when promoters are divided by CpG content, the density of 5hmC is lowest at HCPs, while at LCPs and ICPs 5hmC is at least 3.3 times more abundant (FIG. 28H). To exclude the possibility of species-specific differences in 5hmCG localization, the inventors repeated the analysis in mouse ESCs, with similar results (FIG. 27B). In both human and mouse ESCs, CpG-rich promoters are almost devoid of steady-state hydroxymethylation. Moreover, these results apply to promoters containing H3K4me3 or bivalent chromatin modifications (FIG. 28G).

Together with the observation of an increased local density of guanine on the strand of hydroxymethylation, the inventors postulated that promoters with high GC content but low CpG density are more likely to be hydroxymethylated. Indeed, such bivalent ($p<1E-300$) and H3K4me3-only promoters ($p=7.8E-286$) are more enriched with 5hmC (FIG. 7C).

To determine if hydroxymethylation at distal regulatory elements is also biased towards low CpG density, three classes of DNase I hypersensitive sites (DHSs) were examined: 1) those lacking the enhancer histone modifications H3K4me1 and H3K27ac; 2) putative poised enhancers bearing only H3K4me1; and 3) putative active enhancers with both modifications (Hawkins et al., 2010; Myers et al., 2011). Poised and active enhancers exhibit the strongest enrichment of 5hmC (FIGS. 27D-F), which almost exclusively corresponds to low CpG density regions. Like promoters, the few distal DHSs with high CpG density are generally composed of low 5hmCG content. Similar results were also observed at distal p300 binding sites (FIGS. 28B-C). Together, these results suggest that the highest levels of 5hmC occur at CpG-low regions of the genome.

Comparing DNase I hypersensitive sites lacking the H3K4me1 and H3K27ac enhancer chromatin marks to poised enhancers having only H3K4me1, DNA methylation drops by 12.6% and 5hmC increases by 2.7-fold (FIG. 28D-F). In contrast, active enhancers having both H3K4me1 and H3K27ac have 8.3% less 5mCG than poised enhancers, but with only a 1.08-fold increase in 5hmC. These results suggest that while 5mCG is inversely related to both H3K4me1 and H3K27ac, 5hmC is proportional primarily to H3K4me1.

TAB-Seq strategy described herein is both precise and accurate. First, using synthetic DNA oligonucleotide models, excess recombinant mTet1 can efficiently oxidize 5mC to 5caC. Employing conventional sodium bisulfite treatment, 5caC can subsequently be deaminated to 5caU/U and read as thymine by Sanger sequencing. Next, by utilizing βGT-mediated transfer of glucose specifically to 5hmC, 5gmC cannot act as a substrate for the mTet1-mediated oxidation, thereby preserving 5hmC as cytosine when subjected to sodium bisulfite treatment. Therefore, coupling βGT-mediated protection of 5hmC with mTet 1-based oxidation of 5mC allows for the distinction of 5hmC from unmodified cytosine and 5mC by sequencing. The presence of 5fC and 5caC in the original genomic DNA will not interfere with TAB-Seq since these further oxidized cytosines behave like unmodified cytosine under bisulfite treatment (He et al., 2011). This method has also been ueitilized to examine previously reported 5hmC enriched loci (Szulwach et al., 2011b) and successfully identified genuine 5hmC sites. These results demonstrate the general utility of TAB-Seq to assess 5hmC in a loci-specific manner, much the same as the routine traditional bisulfite sequencing is currently used.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

PCT Appln. PCT/US2011/031370
Beck and Rakyan, *Trends Genet.*, 24:231-237, 2008.
Beck, *Nat. Biotechnol.*, 28:1026-1028, 2010.
Berman et al., *Nat. Genet.*, 44:40-46, 2012.
Bernstein et al., *Cell*, 128:669-681, 2007.
Bird, *J. Mol. Biol.*, 409:47-53, 2011.
Bird, *Genes Dev.*, 16:6-21, 2002.
Bock et al., *Nat. Biotechnol.*, 28:1106-1114, 2010.
Bock, *Epigenomics*, 1:99-110, 2009.
Boysen et al., *J. Chromatogr. B Analyt. Technol. Biomed. Life Sci.*, 878:375, 2010.
Chavez et al., *Genome Res.*, 20:1441-1450, 2010.
Chen and Riggs, *J. Biol. Chem.*, 286:18347-18353, 2011.
Clark et al., *Nucleic Acids Res.* 22:2990-2997, 1994.
Cokus et al., *Nature*, 452:215-219, 2008.
Cortellino et al., *Cell*, 146:67-79, 2011.
Dai and He, *Org. Lett.*, 13:3446-3449, 2011.
Dawlaty et al., *Cell. Stem Cell*, 9:166-175, 2011.
De Carvalho et al., *Trends Cell Biol.*, 20:609-617, 2010.
Deaton and Bird, *Genes Dev.*, 25:1010-1022, 2011.
Donnelly et al., *Protein Expr. Purif.*, 47(2):446-454, 2006.
Down et al., *Nat. Biotechnol.*, 26:779-785, 2008.
Esteller and Aberrant, *Annu. Rev. Pharmacol. Toxicol.*, 45:629-656, 2005.
Esteller, *Nat. Rev. Genet.*, 8:286-298, 2007.
Evans, *Austral. J. Chem.*, 60(6): 384-395, 2007.
Feinberg and Tycko, *Nat. Rev. Cancer,* 4:143-153, 2004.
Feinberg and Vogelstein, *Nature*, 301:89-92, 1983.
Ficz et al., *Nature*, 473:398-402, 2011.
Frauer et al., *PloS One*, 6:e21306, 2011.
Frommer et al.: *Proc. Natl. Acad Sci. USA*, 89:1827-1831, 1992.
Geier and Modrich, *J. Biol. Chem.*, 254:1408-1413, 1979.
Globisch et al., *PloS One*, 5:e15367, 2010.
Goll and Bestor, *Annu. Rev. Biochem.*, 74:481-514, 2005.
Gu et al., *Nature*, 477:606-610, 2011.
Guo et al., *Cell*, 145:423-434, 2011.
Harris et al., *Nat. Biotechnol.*, 28:1097-1105, 2010.
Hashimoto et al., *Nucleic Acids Res.*, 2012 (Ahead of Print)
Hawkins et al., *Cell. Stem Cell*, 6:479-491, 2010.
He et al., *Science*, 333:1303-1307, 2011.
Hein et al., *Pharmaceut. Res.*, 25(10):2216-2230, 2008.
Hon et al., *Genome Res.*, 22:246-258, 2012.
Hsu et al., *Bioinformatics*, 22:1036-1046, 2006.
Huang et al., *Nucleic Acids Res.*, 10:1579, 1982.
Huang et al., *PloS One* 5, e8888, 2010.
Inoue and Zhang, *Science*, 334:194, 2011.
Iqbal et al.: *Proc. Natl. Acad. Sci. USA*, 108:3642-3647, 2011.
Ito et al., *Nature*, 466:1129-1133, 2010.
Ito et al., *Science*, 333:1300-1303, 2011.
Jacinto et al., *Biotechniques*, 44:35, 37, 39 passim, 2008.
Jaenisch and Bird, *Nat. Genet.*, 33(Suppl):245-254, 2003.
Jin et al., *Nucleic Acids Res.*, 38:e125, 2010.
Jones and Baylin, *Nat. Rev. Genet.*, 3:415-428, 2002.
Josse and Kornberg, *Biol. Chem.*, 237:1968-1976, 1962.
Kent et al., *Genome Res.*, 12:996-1006, 2002.
Ko et al., *Nature*, 468:839-843, 2010.
Koh et al., *Cell. Stem Cell*, 8:200-213, 2011.
Kolb et al., *Angew. Chem. Int. Ed.*, 40:2004-2021, 2001.
Kriaucionis and Heintz, *Science*, 324:929-930, 2009.
Kukushkin et al., *Coord. Chem. Rev.*, 181:147, 1999.
Langmead et al., *Genome Biol.*, 10:R25, 2009.
Law and Jacobsen, *Nat. Rev. Genet.*, 11:204-220, 2010.
Li et al., *Bioinformatics*, 25:2078-2079, 2009.
Lister et al., *Cell*, 133:523-536, 2008.
Lister et al., *Nature*, 462:315-322, 2009.
Lister et al., *Nature*, 471:68-73, 2011.
Lorsbach et al., *Leukemia*, 17: 637-641, 2003.
Maiti and Drohat, *J. Biol. Chem.*, 286:35334-35338, 2011.
Margulies et al., *Nature*, 437:376-380, 2005.
Marinus and Morris, *J. Bacteriol.*, 114:1143-1150, 1973.
May and Hattman, *J. Bacteriol.*, 123:768-770, 1975.
Meissner et al., *Nature*, 454:766-770, 2008.
Meissner, *Nat. Biotechnol.*, 28:1079-1088, 2010.
Meyer et al., *Chem, Bio. Chem.*, 4:610-614, 2003.
Mishina and He, *J. Am. Chem. Soc.*, 125:8730-8731, 2003.
Moses and Moorhouse, *Chem. Soc. Rev.*, (36):1249-1262, 2007.
Munzel, et al., *Angew Chem. Int. Ed. Engl.*, 49:5375-5377, 2010.
Myers et al., *PLoS Biol.*, 9:e1001046., 2011.
Ono et al., *Cancer Res.*, 62:4075-4080, 2002.
Pastor et al., *Nature*, 473:394-397, 2011.
Pelizzola and Ecker, *FEBS Ltrs.*, 585:1994-2000, 2011.
Pfaffeneder et al., *Angew Chem. Int. Ed Engl.*, 50:7008-7012, 2011.
Quenneville et al., *Mol. Cell*, 44:361-372, 2011.
Robertson et al., *Nat. Protoc.*, 7:340-350, 2012.
Robertson et al., *Nucleic Acids Res.*, 39:e55, 2011.
Schuebel et al., *PLoS Genet.*, 3:1709-1723, 2007.
Siegfried and Cedar, *Curr. Biol.*, 7:305-307, 1997.
Siepel et al., *Genome Res.*, 15:1034-1050, 2005.
Song et al., *Nat. Biotechnol.*, 29:68-72, 2011.
Song et al., *Nat. Methods*, 9:75-77, 2012.
Stadler et al., *Nature*, 480:490-495, 2011.
Stroud et al., *Genome Biol.*, 12:R54, 2011.
Szulwach et al., *PLoS Genet.*, 7:e1002154, 2011a.
Szulwach et al., *Nat. Neurosci.*, 14:1607-1616, 2011b.
Szwagierczak et al., *Nucleic Acids Res.*, 38:e181, 2010.
Tahiliani et al., *Science*, 324:930-935, 2009.
Tanabe et al., *J. Am. Chem. Soc.*, 129:8034-8040, 2007.
Tornoe et al., *J. Organic Chem.*, 67(9):3057-3064, 2002.
Valinluck et al., *Nucleic Acids Res.*, 32:4100-4108, 2004.
Weber et al., *Nature Genetics*, 37:853-862, 2005.
Weisenberger et al., In *Comprehensive DNA Methylation Analysis on the Illumina® Infinium® Assay Platform*, Pub. No. 270-2008-003, Illumina, 2008.
Wigler et al., *Cell*, 24:33-40, 1981.
Williams et al., *Anal. Biochem.*, 114:73, 1981.
Williams et al., *Nature*, 473:343-348, 2011.
Wossidlo et al., *Nat. Commun.*, 2:241, 2011.
Wu and Zhang, *Genes Dev.*, 25:2436-2452, 2011.
Wu et al., *Genes Dev.*, 25:679-684, 2011.
Xu et al., *Mol. Cell*, 42:451-464, 2011.
Yildirim et al., *Cell*, 147:1498-1510, 2011.
Zeschnigk et al., *Hum. Mol. Genet.*, 6:387-395, 1997.
Zhang et al., *Nature Chem. Biol.*, 8:328-330, 2012.
Zhang et al., *Genome Biol.*, 9: R137, 2008.

What is claimed is:

1. A method for detecting 5-methylcytosine in a nucleic acid comprising converting 5-methylcytosine to 5-carboxylcytosine in the nucleic acid using enzymatic modification by methylcytosine dioxygenase; bisulfite sequencing the converted nucleic acid; and detecting 5-methylcytosine in the nucleic acid at positions where 5-carboxylcytosine is identified by reading a thymine in the converted nucleic acid as compared to a cytosine in the positions of a control sequence, wherein the control sequence is the sequence of the nucleic acid when bisulfite sequenced but not converted.

2. The method of claim 1, wherein the methylcytosine dioxygenase is TET1, TET2, or TET3, or a homologue thereof.

3. The method of claim 1, wherein the methylcytosine dioxygenase comprises amino acids 1367-2039 of SEQ ID NO: 1.

4. The method of claim 1, further comprising modifying 5-hydroxymethylcytosine with a first detectable label or a first detectable functional group prior to converting 5-methylcytosine to 5-carboxylcytosine.

5. The method of claim 4, further comprising detecting 5-hydroxymethylcytosine in the nucleic acid.

6. The method of claim 1, wherein the nucleic acid is genomic DNA.

7. A method for distinguishing 5-hydroxymethylcytosine from 5-methylcytosine in a nucleic acid molecule comprising:
   a) modifying 5-hydroxymethylcytosine in the nucleic acid molecule with a glucose or a modified glucose;
   b) treating the modified nucleic acid molecule with methylcytosine dioxygenase under conditions to convert 5-methylcytosine to 5-carboxylcytosine;
   c) then sequencing the treated nucleic acid using bisulfite; and
   d) distinguishing 5-hydroxymethylcytosine from 5-methylcytosine in the bisulfite sequence by reading a cytosine for 5-hydroxymethylcytosine and a thymine for 5-methylcytosine.

8. The method of claim 7, wherein the methylcytosine dioxygenase is TET1, TET2, or TET3, or a homologue thereof.

9. The method of claim 7, wherein the 5-hydroxymethylcytosine is modified by a process comprising incubating the nucleic acid molecule with β-glucosyltransferase and a glucose or modified glucose molecule.

10. The method of claim 7, wherein the nucleic acid molecule is genomic DNA.

* * * * *